(12) United States Patent
Terashita et al.

(10) Patent No.: US 7,833,761 B2
(45) Date of Patent: Nov. 16, 2010

(54) AMINO ACID PRODUCING MICROORGANISM AND A METHOD FOR PRODUCING AN AMINO ACID

(75) Inventors: Masaru Terashita, Kawasaki (JP); Yoshihiro Usuda, Kawasaki (JP); Kazuhiko Matsui, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/202,476

(22) Filed: Sep. 2, 2008

(65) Prior Publication Data

US 2009/0068712 A1    Mar. 12, 2009

(30) Foreign Application Priority Data

Sep. 4, 2007    (JP) .............................. 2007-228733

(51) Int. Cl.
*C12P 13/04* (2006.01)
*C12P 13/06* (2006.01)
*C12P 13/08* (2006.01)
*C12P 13/22* (2006.01)

(52) U.S. Cl. ...................... 435/106; 435/115; 435/108; 435/116; 435/189

(58) Field of Classification Search ........................ None
See application file for complete search history.

(56) References Cited

U.S. PATENT DOCUMENTS

| | | | |
|---|---|---|---|
| 5,661,012 A | 8/1997 | Sano et al. | |
| 5,827,698 A | 10/1998 | Kikuchi et al. | |
| 5,830,716 A | 11/1998 | Kojima et al. | |
| 5,932,453 A | 8/1999 | Kikuchi et al. | |
| 6,040,160 A | 3/2000 | Kojima et al. | |
| 6,911,332 B2 | 6/2005 | Usuda et al. | |
| 7,026,149 B2 | 4/2006 | Usuda et al. | |
| 7,029,893 B2 | 4/2006 | Usuda et al. | |
| 7,060,475 B2 | 6/2006 | Usuda et al. | |
| 7,090,998 B2 | 8/2006 | Ishikawa et al. | |
| 7,192,748 B2 | 3/2007 | Usuda et al. | |
| 7,220,570 B2 | 5/2007 | Usuda et al. | |
| 7,306,933 B2 | 12/2007 | Dien et al. | |
| 2002/0155556 A1 | 10/2002 | Imaizumi et al. | |
| 2002/0160461 A1 | 10/2002 | Nakai et al. | |
| 2004/0229305 A1 | 11/2004 | Usuda et al. | |
| 2004/0229321 A1 | 11/2004 | Savrasova et al. | |
| 2004/0265956 A1 | 12/2004 | Takikawa et al. | |
| 2005/0181488 A1 | 8/2005 | Akhverdian et al. | |
| 2005/0214911 A1 | 9/2005 | Marchenko et al. | |
| 2005/0233308 A1 | 10/2005 | Nishio et al. | |
| 2006/0019355 A1 | 1/2006 | Ueda et al. | |
| 2006/0019356 A1 | 1/2006 | Usuda et al. | |
| 2006/0030010 A1 | 2/2006 | Usuda et al. | |
| 2006/0030011 A1 | 2/2006 | Usuda et al. | |
| 2006/0088919 A1 | 4/2006 | Rybak et al. | |
| 2006/0141586 A1 | 6/2006 | Rybak et al. | |
| 2006/0234356 A1 | 10/2006 | Usuda et al. | |
| 2006/0234357 A1 | 10/2006 | Usuda et al. | |
| 2007/0212764 A1 | 9/2007 | Ptitsyn et al. | |
| 2007/0249017 A1 | 10/2007 | Usuda et al. | |

FOREIGN PATENT DOCUMENTS

| | | |
|---|---|---|
| EP | 1 253 195 A1 | 10/2002 |
| EP | 1 715 055 A2 | 10/2006 |
| EP | 1 715 055 A3 | 10/2006 |
| EP | 1 715 056 A1 | 10/2006 |
| JP | 2001-136991 A | 5/2001 |
| WO | WO02/14522 A1 | 2/2002 |
| WO | WO02/22829 A2 | 3/2002 |
| WO | WO2006/135075 A1 | 12/2006 |
| WO | WO2007/013695 A1 | 2/2007 |
| WO | WO2007/039532 A2 | 4/2007 |
| WO | WO2007/039532 A3 | 4/2007 |
| WO | WO2007/100009 A1 | 9/2007 |
| WO | WO2007/136133 A1 | 11/2007 |
| WO | WO2008/002053 A1 | 1/2008 |
| WO | WO2008/010565 A2 | 1/2008 |
| WO | WO2008/032757 A1 | 3/2008 |
| WO | WO2008/072761 A2 | 6/2008 |
| WO | WO2008/081959 A1 | 7/2008 |
| WO | WO2008/102861 A1 | 8/2008 |
| WO | WO2008/107277 A1 | 9/2008 |

OTHER PUBLICATIONS

Blaschkowski, H. P., et al., "Routes of Flavodoxin and Ferredoxin Reduction in *Escherichia coli* CoA-Acylating Pyruvate: Flavodoxin and NADPH: Flavodoxin Oxidoreductases Participating in the Activation of Pyruvate Formate-Lyase," Eur. J. Chem. 1982;123:563-569.

Ferredoxin oxidoreductase beta subunit [*Methanococcus maripaludis* S2]., [online], GenBank, Jan. 18, 2006, accession:NP_988624.

Hypothetical protein, MMP1502 [*Methanococcus maripaludis* S2]., [online], GenBank, Jan. 18, 2006, accession:NP_988622.

Hypothetical protein, pyruvate oxidoreductase-associated [*Methanococcus maripaludis* S2]., [online], GenBank, Jan. 18, 2006, accession:NP_988623.

Ikeda, T., et al., "Anabolic five subunit-type pyruvate:ferredoxin oxidoreductase from *Hydrogenobacter thermophilus* TK-6," Biochem. Biophys. Res. Commun. 2006;340:76-82.

(Continued)

*Primary Examiner*—Rebecca E. Prouty
(74) *Attorney, Agent, or Firm*—Shelly Guest Cermak; Cermak Nakajima LLP

(57) ABSTRACT

A microorganism is provided which has an ability to produce an L-amino acid such as L-lysine, L-tryptophan, L-phenylalanine, L-valine, L-leucine, L-isoleucine and L-serine, and has been modified to increase the activity of pyruvate synthase or pyruvate:NADP$^+$ oxidoreductase. This microorganism is cultured in a medium containing ethanol or an aliphatic acid as the carbon source to produce and accumulate the L-amino acid in the medium or cells, and the L-amino acid is collected from the medium or the cells.

12 Claims, 1 Drawing Sheet

OTHER PUBLICATIONS

Indolepyruvate ferredoxin oxidoreductase [*Methanococcus maripaludis* S2]., [online], GenBank, Jan. 18, 2006, accession:NP 988627, http://www.genome.adjp/dbget-.

KEGG (Kyoto Encyclopedia of Genes and Genomes) Entry No. b1378, bin/www_bget?eco+1378.

Lin, W., et al., "The importance of *porE* and *porF* in the anabolic pyruvate oxidoreductase of *Methanococcus maripaludis*," Arch. Microbiol. 2004;181:68-73.

Lin, W. C., et al., "The anabolic pyruvate oxidoreductase from *Methanococcus maripaludis*," Arch. Microbiol. 2003;179:444-456.

Probable pyruvate-flavodoxin oxidoreductase., [online], Jul. 10, 2007, accession:P52647, database PIR.

Pyruvate flavodoxin/ferrodoxin oxidoreductase [*Chlorobium tepidum* TLS]., [online], GenBank, Dec. 2, 2005, accession:NP_662511.

Pyruvate oxidoreductase (synthase) subunit alpha [*Methanococcus maripaludis* S2]., [online], GenBank, Jan. 18, 2006, accession:NP_988625.

Pyruvate oxidoreductase (synthase) subunit delta [*Methanococcus maripaludis* S2]., [online], GenBank, Jan. 18, 2006, accession:NP_988626.

Reed, J. L., et al., "An expanded genome-scale model of *Escherichia coli* K-I2 (*i*JR904 GSM/GPR)," Genome Biology 2003;4:R54.

Rotte, C., et al., "PyruvateL NADP+ Oxidoreductase from the Mitochondrion of *Euglena gracilis* and from the Apicomplexan *Cryptosporidium parvum*: A Biochemical Relic Linking Pyruvate Metabolism in Mitochondriate and Amitochondriate Protists," Mol. Bio. Evol. 2001:18(5):710-720.

International Search Report for PCT Patent App. No. PCT/JP2008/065834 (Oct. 7, 2008).

Mahadevan, R., et al., "Characterization of Metabolism in the Fe(III)-Reducing Organism *Geobacter sulfurreducens* by Constraint-Based Modeling," Applied Environmen. Microbiol. 2006;72(2):1558-1568.

SEQUENCE LISTING

<160> NUMBER OF SEQ ID NOS: 55

<210> SEQ ID NO 1
<211> LENGTH: 3558
<212> TYPE: DNA
<213> ORGANISM: Chlorobium tepidum
<220> FEATURE:
<221> NAME/KEY: CDS
<222> LOCATION: (1)..(3558)

<400> SEQUENCE: 1

```
atg acc cgg aca ttc aag aca atg gag ggg aat gaa gct ctt gct cat      48
Met Thr Arg Thr Phe Lys Thr Met Glu Gly Asn Glu Ala Leu Ala His
1               5                  10                  15 gtc gcc tat cgc act aat gaa gtc atc tcg ata tac ccg att acc ccg      96
Val Ala Tyr Arg Thr Asn Glu Val Ile Ser Ile Tyr Pro Ile Thr Pro
                20                  25                  30 gca tct ccg atg gga gag tac tcc gac gca tgg gcc gct gtc gat gta     144
Ala Ser Pro Met Gly Glu Tyr Ser Asp Ala Trp Ala Ala Val Asp Val
            35                  40                  45 aaa aat atc tgg ggt acc gtg cca ctc gtc aat gag atg cag agc gaa     192
Lys Asn Ile Trp Gly Thr Val Pro Leu Val Asn Glu Met Gln Ser Glu
        50                  55                  60 gcc ggt gcc gcc gcc gcc gtt cac ggc gcg ttg cag acc ggc gcg ctg     240
Ala Gly Ala Ala Ala Ala Val His Gly Ala Leu Gln Thr Gly Ala Leu
65                  70                  75                  80 acg acc acc ttc acg gcc tct cag ggt ctc tta ctg atg atc ccg aac     288
Thr Thr Thr Phe Thr Ala Ser Gln Gly Leu Leu Leu Met Ile Pro Asn
                85                  90                  95 atg tac aag atc gcc ggt gaa ctg acc ccc tgc gtg att cac gtg tca     336
Met Tyr Lys Ile Ala Gly Glu Leu Thr Pro Cys Val Ile His Val Ser
                100                 105                 110 gcc cgt tcg ctg gcc gcg cag gcg ctc tcg ata ttc tgc gac cac ggt     384
Ala Arg Ser Leu Ala Ala Gln Ala Leu Ser Ile Phe Cys Asp His Gly
            115                 120                 125 gac gtg atg tcg gtc agg ggc acc ggc ttc gcg ctc ctc gct tcc tgt     432
Asp Val Met Ser Val Arg Gly Thr Gly Phe Ala Leu Leu Ala Ser Cys
        130                 135                 140 tcg gta cag gag gta atg gac atg gcg ctg att tcg cag gcc gca acg     480
Ser Val Gln Glu Val Met Asp Met Ala Leu Ile Ser Gln Ala Ala Thr
145                 150                 155                 160 ctc gaa tcg cgc gtg cca ttc ctg cac ttc ttc gac ggc ttc cgc acg     528
Leu Glu Ser Arg Val Pro Phe Leu His Phe Phe Asp Gly Phe Arg Thr
                165                 170                 175
```

```
                                                    -continued
tcg cac gaa atc tcg aaa atc gag gtg ctc tcg gac gaa cag att cgc      576
Ser His Glu Ile Ser Lys Ile Glu Val Leu Ser Asp Glu Gln Ile Arg
        180                 185                 190 tcg atg atc aac gac gag ctg gtc ttc gca cac cgc atg cgc cgc atg      624
Ser Met Ile Asn Asp Glu Leu Val Phe Ala His Arg Met Arg Arg Met
    195                 200                 205 tcg cct gat gca ccg atc atc cgc ggt acc tcg cag aat ccg gac gtc      672
Ser Pro Asp Ala Pro Ile Ile Arg Gly Thr Ser Gln Asn Pro Asp Val
210                 215                 220 tat ttc cag gca cgc gag agc gtc aac aaa tat tat gag gcc tgc ccg      720
Tyr Phe Gln Ala Arg Glu Ser Val Asn Lys Tyr Tyr Glu Ala Cys Pro
225                 230                 235                 240 tca atc acc cag aag gcg atg gac cag ttc gcc aaa ctg act ggg cgc      768
Ser Ile Thr Gln Lys Ala Met Asp Gln Phe Ala Lys Leu Thr Gly Arg
        245                 250                 255 agc tat aaa ctt tac cag tac tac ggc gct ccg gat gcc gac cgt atc      816
Ser Tyr Lys Leu Tyr Gln Tyr Tyr Gly Ala Pro Asp Ala Asp Arg Ile
    260                 265                 270 atc atc atg atg ggg tca ggt gcc gag acc gct ctc gaa act gtc gaa      864
Ile Ile Met Met Gly Ser Gly Ala Glu Thr Ala Leu Glu Thr Val Glu
275                 280                 285 tac ctc aac aac cac ggc gaa aag gtc ggt ctg gtc aag gta cgc ctt      912
Tyr Leu Asn Asn His Gly Glu Lys Val Gly Leu Val Lys Val Arg Leu
        290                 295                 300 ttc agg cca ttc gac gtt gca acc ttc atc gca tcg cta cca tcg agc      960
Phe Arg Pro Phe Asp Val Ala Thr Phe Ile Ala Ser Leu Pro Ser Ser
305                 310                 315                 320 gtg aag agt atc gcg gtg ctc gac cgt gtc aag gaa cca ggc agc gct     1008
Val Lys Ser Ile Ala Val Leu Asp Arg Val Lys Glu Pro Gly Ser Ala
            325                 330                 335 ggc gaa ccg ctc tat ctc gat gta gtc aac gcc gta gcc gaa tcg tac     1056
Gly Glu Pro Leu Tyr Leu Asp Val Val Asn Ala Val Ala Glu Ser Tyr
        340                 345                 350 cag gaa ggc aaa tgc gct tcg atg cca agc gtt ttg ggt ggg cgc tat     1104
Gln Glu Gly Lys Cys Ala Ser Met Pro Ser Val Leu Gly Gly Arg Tyr
    355                 360                 365 ggc ctg tcg tcg aag gag ttc act ccg gcg atg gtc aag gcg atc ttc     1152
Gly Leu Ser Ser Lys Glu Phe Thr Pro Ala Met Val Lys Ala Ile Phe
370                 375                 380 gac aat atg aac gcg gaa tct cca aag aat cac ttc acc gtt ggc atc     1200
Asp Asn Met Asn Ala Glu Ser Pro Lys Asn His Phe Thr Val Gly Ile
385                 390                 395                 400 gac gat gac gta acc aag aag agc ctc gcc tac gac gag acc ttc tcg     1248
Asp Asp Asp Val Thr Lys Lys Ser Leu Ala Tyr Asp Glu Thr Phe Ser
            405                 410                 415 att gag ccg gac tcg gtc ttc cgc gcc ctc ttc tac ggc ctc ggt tca     1296
Ile Glu Pro Asp Ser Val Phe Arg Ala Leu Phe Tyr Gly Leu Gly Ser
        420                 425                 430 gac ggc acg gtc ggt gca aac aag aac tcg atc aag atc att ggc gaa     1344
Asp Gly Thr Val Gly Ala Asn Lys Asn Ser Ile Lys Ile Ile Gly Glu
    435                 440                 445 aac acc gac aac tac gcg cag ggc ttc ttc gtc tac gac tcc aag aaa     1392
Asn Thr Asp Asn Tyr Ala Gln Gly Phe Phe Val Tyr Asp Ser Lys Lys
450                 455                 460 gcc ggt tcg atc acg acc tcg cac ctg cgg ttc ggc ccg gag cag atc     1440
Ala Gly Ser Ile Thr Thr Ser His Leu Arg Phe Gly Pro Glu Gln Ile
465                 470                 475                 480 cgc tcg acc tac ctc atc acc gag gcg cag ttc gtc ggc tgc cac cac     1488
Arg Ser Thr Tyr Leu Ile Thr Glu Ala Gln Phe Val Gly Cys His His
            485                 490                 495
```

```
                                                      -continued tgg gtc ttt ctc gaa atg atc gac gtt gcc aag aac ctc aag cag ggt    1536
Trp Val Phe Leu Glu Met Ile Asp Val Ala Lys Asn Leu Lys Gln Gly
        500                 505                 510 ggt acg ctg ctc atc aac tcg gcc tat gcg ccg gat gtg gtg tgg agc    1584
Gly Thr Leu Leu Ile Asn Ser Ala Tyr Ala Pro Asp Val Val Trp Ser
    515                 520                 525 aag ctc ccg cgt ccg gtg cag cag cac ttg atc gac aag cag gcg aag    1632
Lys Leu Pro Arg Pro Val Gln Gln His Leu Ile Asp Lys Gln Ala Lys
530                 535                 540 ctc tac acc atc gat gcc tac aag gtc gcc cac gaa agc ggc atg ggt    1680
Leu Tyr Thr Ile Asp Ala Tyr Lys Val Ala His Glu Ser Gly Met Gly
545                 550                 555                 560 cag cgc atc aac act atc atg cag gcc tgt ttc ttc gcc att tcg ggc    1728
Gln Arg Ile Asn Thr Ile Met Gln Ala Cys Phe Phe Ala Ile Ser Gly
            565                 570                 575 gtg ctg ccg cgt gaa gag gca atc gaa aag atc aag gac gcg atc cgc    1776
Val Leu Pro Arg Glu Glu Ala Ile Glu Lys Ile Lys Asp Ala Ile Arg
        580                 585                 590 cac acc tac ggc aaa aag ggc gat gag gtc gtt cag cag aac atc aag    1824
His Thr Tyr Gly Lys Lys Gly Asp Glu Val Val Gln Gln Asn Ile Lys
    595                 600                 605 gca gtt gac aac acg ctt gcc aac ctg cat gaa gtg aaa atc ggc gct    1872
Ala Val Asp Asn Thr Leu Ala Asn Leu His Glu Val Lys Ile Gly Ala
610                 615                 620 gtg gca gac agc acc aag gag ctg cgc tcg ccc atc gtt ggc gac gcg    1920
Val Ala Asp Ser Thr Lys Glu Leu Arg Ser Pro Ile Val Gly Asp Ala
625                 630                 635                 640 cca gag ttc gtc tgt aac gtg ctg gca aag att att gcc ggc gag ggc    1968
Pro Glu Phe Val Cys Asn Val Leu Ala Lys Ile Ile Ala Gly Glu Gly
            645                 650                 655 gac tcg att ccg gtc agc aag ctg cct gcc gat gga acc tat ccg ctc    2016
Asp Ser Ile Pro Val Ser Lys Leu Pro Ala Asp Gly Thr Tyr Pro Leu
        660                 665                 670 ggc acc acg aag ttc gag aaa cgc aac ctc gcg cag gag att ccg gtc    2064
Gly Thr Thr Lys Phe Glu Lys Arg Asn Leu Ala Gln Glu Ile Pro Val
    675                 680                 685 tgg gct ccg gag ctg tgc atc gag tgt ggc aag tgc tcg atg gtc tgc    2112
Trp Ala Pro Glu Leu Cys Ile Glu Cys Gly Lys Cys Ser Met Val Cys
690                 695                 700 ccg cac gct gcc atc cgc atc aag gtt tac gag ccg aag cac ctc gaa    2160
Pro His Ala Ala Ile Arg Ile Lys Val Tyr Glu Pro Lys His Leu Glu
705                 710                 715                 720 aac gcc ccg gca acc ttc aag agc ctc gat gcg aaa gca aaa aac tgg    2208
Asn Ala Pro Ala Thr Phe Lys Ser Leu Asp Ala Lys Ala Lys Asn Trp
            725                 730                 735 gag ggc atg cgc tat acg gtt cag att gca ccg gaa gat tgt acc ggc    2256
Glu Gly Met Arg Tyr Thr Val Gln Ile Ala Pro Glu Asp Cys Thr Gly
        740                 745                 750 tgc caa ctc tgc gtc aac gcc tgc ccc gca aga gac aag cag gtt gaa    2304
Cys Gln Leu Cys Val Asn Ala Cys Pro Ala Arg Asp Lys Gln Val Glu
    755                 760                 765 ggc cgc aaa gcg ctc aac atg cac gag cag gct ccg ctg cgc gaa acc    2352
Gly Arg Lys Ala Leu Asn Met His Glu Gln Ala Pro Leu Arg Glu Thr
770                 775                 780 gaa tct gcc tgc tgg agc ttc ttc atc aat ctc ccg gaa ttc gac cgc    2400
Glu Ser Ala Cys Trp Ser Phe Phe Ile Asn Leu Pro Glu Phe Asp Arg
785                 790                 795                 800 aac aag atc aac cag cgc ctc atc aaa gag cag cag ctt cag cag cca    2448
Asn Lys Ile Asn Gln Arg Leu Ile Lys Glu Gln Gln Leu Gln Gln Pro
```

-continued

| | 805 | | | | 810 | | | | 815 | | | | |
|---|---|---|---|---|---|---|---|---|---|---|---|---|---|
| ctc | ttc | gag | ttc | tcg | ggc | gca | tgc | tcg | ggc | tgc | ggc | gaa acg cca tac | 2496 |
| Leu | Phe | Glu | Phe | Ser | Gly | Ala | Cys | Ser | Gly | Cys | Gly | Glu Thr Pro Tyr | |
| | | | 820 | | | | | 825 | | | | 830 | |

| gtc | aag | ctg | atg | act | cag | ctc | ttc | ggt | gat | cgc | ctc | gtt atc ggc aac | 2544 |
|---|---|---|---|---|---|---|---|---|---|---|---|---|---|
| Val | Lys | Leu | Met | Thr | Gln | Leu | Phe | Gly | Asp | Arg | Leu | Val Ile Gly Asn | |
| | | | 835 | | | | | 840 | | | | 845 | |

| gcc | acc | ggc | tgc | tcg | tcg | atc | tac | ggc | ggc | aac | ctg | ccg acc acg ccg | 2592 |
|---|---|---|---|---|---|---|---|---|---|---|---|---|---|
| Ala | Thr | Gly | Cys | Ser | Ser | Ile | Tyr | Gly | Gly | Asn | Leu | Pro Thr Thr Pro | |
| | 850 | | | | | 855 | | | | | 860 | | |

| tat | gca | gcc | aac | ccg | cag | ggc | ctt | ggg | cca | acg | tgg | tcg aac tcg ctt | 2640 |
|---|---|---|---|---|---|---|---|---|---|---|---|---|---|
| Tyr | Ala | Ala | Asn | Pro | Gln | Gly | Leu | Gly | Pro | Thr | Trp | Ser Asn Ser Leu | |
| 865 | | | | | 870 | | | | | 875 | | | 880 |

| ttc | gag | gac | acg | gca | gag | ttc | gcg | ctt | ggt | ttc | cgg | ata tcg atc gac | 2688 |
|---|---|---|---|---|---|---|---|---|---|---|---|---|---|
| Phe | Glu | Asp | Thr | Ala | Glu | Phe | Ala | Leu | Gly | Phe | Arg | Ile Ser Ile Asp | |
| | | | | 885 | | | | | 890 | | | | 895 |

| aag | cag | cag | caa | ttt | gcc | aaa | gag | ctg | gtc | aaa | aag | ctc gct ggt gac | 2736 |
|---|---|---|---|---|---|---|---|---|---|---|---|---|---|
| Lys | Gln | Gln | Gln | Phe | Ala | Lys | Glu | Leu | Val | Lys | Lys | Leu Ala Gly Asp | |
| | | | 900 | | | | | 905 | | | | 910 | |

| atc | ggt | gaa | aac | ctt | gcc | acc | gcc | att | ctc | aac | gcc | acg cag aac agt | 2784 |
|---|---|---|---|---|---|---|---|---|---|---|---|---|---|
| Ile | Gly | Glu | Asn | Leu | Ala | Thr | Ala | Ile | Leu | Asn | Ala | Thr Gln Asn Ser | |
| | | | 915 | | | | | 920 | | | | 925 | |

| gaa | ccg | gag | att | ttc | gag | cag | cgt | gag | cgc | gtg | gcc | gtg ctg aag gat | 2832 |
|---|---|---|---|---|---|---|---|---|---|---|---|---|---|
| Glu | Pro | Glu | Ile | Phe | Glu | Gln | Arg | Glu | Arg | Val | Ala | Val Leu Lys Asp | |
| | 930 | | | | | 935 | | | | | 940 | | |

| aag | ctc | cag | cag | atg | aaa | tcc | gac | gat | gcc | aag | aac | ctg ctt gct gtg | 2880 |
|---|---|---|---|---|---|---|---|---|---|---|---|---|---|
| Lys | Leu | Gln | Gln | Met | Lys | Ser | Asp | Asp | Ala | Lys | Asn | Leu Leu Ala Val | |
| 945 | | | | | 950 | | | | | 955 | | | 960 |

| gct | gac | atg | ctg | gtc | aag | aag | agc | gtg | tgg | gct | gtc | ggc ggc gac ggc | 2928 |
|---|---|---|---|---|---|---|---|---|---|---|---|---|---|
| Ala | Asp | Met | Leu | Val | Lys | Lys | Ser | Val | Trp | Ala | Val | Gly Gly Asp Gly | |
| | | | | 965 | | | | | 970 | | | | 975 |

| tgg | gcc | tac | gat | atc | ggt | tac | ggg | ggt | ctc | gac | cac | gtc acc gca tcg | 2976 |
|---|---|---|---|---|---|---|---|---|---|---|---|---|---|
| Trp | Ala | Tyr | Asp | Ile | Gly | Tyr | Gly | Gly | Leu | Asp | His | Val Thr Ala Ser | |
| | | | 980 | | | | | 985 | | | | 990 | |

| ggc | aag | aac | gtc | aac | atg | ctc | gtg | ctc | gac | acc | gag | gtc tat tcc aat | 3024 |
|---|---|---|---|---|---|---|---|---|---|---|---|---|---|
| Gly | Lys | Asn | Val | Asn | Met | Leu | Val | Leu | Asp | Thr | Glu | Val Tyr Ser Asn | |
| | | | 995 | | | | | 1000 | | | | 1005 | |

| acc | ggc | ggt | cag | gcc | tcc | aag | gct | acg | ccg | aaa | gcc | gcg atc gcc | 3069 |
|---|---|---|---|---|---|---|---|---|---|---|---|---|---|
| Thr | Gly | Gly | Gln | Ala | Ser | Lys | Ala | Thr | Pro | Lys | Ala | Ala Ile Ala | |
| | | | 1010 | | | | | 1015 | | | | 1020 | |

| aag | ttt | gcc | gct | gcg | ggg | cgc | atc | gct | acc | aag | aaa | gac ctt ggt | 3114 |
|---|---|---|---|---|---|---|---|---|---|---|---|---|---|
| Lys | Phe | Ala | Ala | Ala | Gly | Arg | Ile | Ala | Thr | Lys | Lys | Asp Leu Gly | |
| | 1025 | | | | | 1030 | | | | | 1035 | | |

| ctg | atc | tcg | atg | agc | tac | ggc | aat | gcc | tat | gtg | gcc | agt gtt gca | 3159 |
|---|---|---|---|---|---|---|---|---|---|---|---|---|---|
| Leu | Ile | Ser | Met | Ser | Tyr | Gly | Asn | Ala | Tyr | Val | Ala | Ser Val Ala | |
| | 1040 | | | | | 1045 | | | | | 1050 | | |

| ctt | ggc | gca | cgt | gac | gag | cag | aca | ctc | aga | gct | ttc | atc gaa gcc | 3204 |
|---|---|---|---|---|---|---|---|---|---|---|---|---|---|
| Leu | Gly | Ala | Arg | Asp | Glu | Gln | Thr | Leu | Arg | Ala | Phe | Ile Glu Ala | |
| | 1055 | | | | | 1060 | | | | | 1065 | | |

| gag | gcg | tac | gat | ggc | ccg | tcg | att | atc | atc | gcc | tac | tcg cac tgc | 3249 |
|---|---|---|---|---|---|---|---|---|---|---|---|---|---|
| Glu | Ala | Tyr | Asp | Gly | Pro | Ser | Ile | Ile | Ile | Ala | Tyr | Ser His Cys | |
| | 1070 | | | | | 1075 | | | | | 1080 | | |

| att | gca | cac | ggc | ttt | gac | ttg | tct | atg | ggt | ctg | gag | cac cag aaa | 3294 |
|---|---|---|---|---|---|---|---|---|---|---|---|---|---|
| Ile | Ala | His | Gly | Phe | Asp | Leu | Ser | Met | Gly | Leu | Glu | His Gln Lys | |
| | 1085 | | | | | 1090 | | | | | 1095 | | |

| gca | gcg | gtc | gat | tcc | ggc | cac | tgg | ctg | ctg | tat | cgc | tac aat ccc | 3339 |
|---|---|---|---|---|---|---|---|---|---|---|---|---|---|
| Ala | Ala | Val | Asp | Ser | Gly | His | Trp | Leu | Leu | Tyr | Arg | Tyr Asn Pro | |
| | 1100 | | | | | 1105 | | | | | 1110 | | |

| gac | aga | ctc | aag | gag | gga | ctg | aat | ccg | ctg | cag | ctc | gac tcc aaa | 3384 |

```
Asp Arg Leu Lys Glu Gly Leu Asn Pro Leu Gln Leu Asp Ser Lys
    1115                1120                1125 aag ccg aaa atg ccg gtc gcg gag ttc ctg aac atg gag aac cgc      3429
Lys Pro Lys Met Pro Val Ala Glu Phe Leu Asn Met Glu Asn Arg
    1130                1135                1140 ttc aga ata ctg aag aag acc cac ccc gat ctg gcc aag aag tac      3474
Phe Arg Ile Leu Lys Lys Thr His Pro Asp Leu Ala Lys Lys Tyr
    1145                1150                1155 ttc gag gca atc cag cac gag gtc aat gcc cgc tgg gca cac tac      3519
Phe Glu Ala Ile Gln His Glu Val Asn Ala Arg Trp Ala His Tyr
    1160                1165                1170 gaa cac ctc gcc aac cgt tcg att gaa ggc gaa gca taa               3558
Glu His Leu Ala Asn Arg Ser Ile Glu Gly Glu Ala
    1175                1180                1185

<210> SEQ ID NO 2
<211> LENGTH: 1185
<212> TYPE: PRT
<213> ORGANISM: Chlorobium tepidum

<400> SEQUENCE: 2

Met Thr Arg Thr Phe Lys Thr Met Glu Gly Asn Glu Ala Leu Ala His
1               5                   10                  15

Val Ala Tyr Arg Thr Asn Glu Val Ile Ser Ile Tyr Pro Ile Thr Pro
                20                  25                  30

Ala Ser Pro Met Gly Glu Tyr Ser Asp Ala Trp Ala Ala Val Asp Val
            35                  40                  45

Lys Asn Ile Trp Gly Thr Val Pro Leu Val Asn Glu Met Gln Ser Glu
        50                  55                  60

Ala Gly Ala Ala Ala Val His Gly Ala Leu Gln Thr Gly Ala Leu
65                  70                  75                  80

Thr Thr Thr Phe Thr Ala Ser Gln Gly Leu Leu Leu Met Ile Pro Asn
                85                  90                  95

Met Tyr Lys Ile Ala Gly Glu Leu Thr Pro Cys Val Ile His Val Ser
                100                 105                 110

Ala Arg Ser Leu Ala Ala Gln Ala Leu Ser Ile Phe Cys Asp His Gly
            115                 120                 125

Asp Val Met Ser Val Arg Gly Thr Gly Phe Ala Leu Leu Ala Ser Cys
        130                 135                 140

Ser Val Gln Glu Val Met Asp Met Ala Leu Ile Ser Gln Ala Ala Thr
145                 150                 155                 160

Leu Glu Ser Arg Val Pro Phe Leu His Phe Asp Gly Phe Arg Thr
                165                 170                 175

Ser His Glu Ile Ser Lys Ile Glu Val Leu Ser Asp Glu Gln Ile Arg
            180                 185                 190

Ser Met Ile Asn Asp Glu Leu Val Phe Ala His Arg Met Arg Arg Met
        195                 200                 205

Ser Pro Asp Ala Pro Ile Ile Arg Gly Thr Ser Gln Asn Pro Asp Val
    210                 215                 220

Tyr Phe Gln Ala Arg Glu Ser Val Asn Lys Tyr Tyr Glu Ala Cys Pro
225                 230                 235                 240

Ser Ile Thr Gln Lys Ala Met Asp Gln Phe Ala Lys Leu Thr Gly Arg
                245                 250                 255

Ser Tyr Lys Leu Tyr Gln Tyr Tyr Gly Ala Pro Asp Ala Asp Arg Ile
            260                 265                 270

Ile Ile Met Met Gly Ser Gly Ala Glu Thr Ala Leu Glu Thr Val Glu
```

-continued

```
                275                 280                 285
Tyr Leu Asn Asn His Gly Glu Lys Val Gly Leu Val Lys Val Arg Leu
            290                 295                 300
Phe Arg Pro Phe Asp Val Ala Thr Phe Ile Ala Ser Leu Pro Ser Ser
305                 310                 315                 320
Val Lys Ser Ile Ala Val Leu Asp Arg Val Lys Glu Pro Gly Ser Ala
                325                 330                 335
Gly Glu Pro Leu Tyr Leu Asp Val Val Asn Ala Val Ala Glu Ser Tyr
            340                 345                 350
Gln Glu Gly Lys Cys Ala Ser Met Pro Ser Val Leu Gly Gly Arg Tyr
            355                 360                 365
Gly Leu Ser Ser Lys Glu Phe Thr Pro Ala Met Val Lys Ala Ile Phe
            370                 375                 380
Asp Asn Met Asn Ala Glu Ser Pro Lys Asn His Phe Thr Val Gly Ile
385                 390                 395                 400
Asp Asp Asp Val Thr Lys Lys Ser Leu Ala Tyr Asp Glu Thr Phe Ser
                405                 410                 415
Ile Glu Pro Asp Ser Val Phe Arg Ala Leu Phe Tyr Gly Leu Gly Ser
                420                 425                 430
Asp Gly Thr Val Gly Ala Asn Lys Asn Ser Ile Lys Ile Ile Gly Glu
            435                 440                 445
Asn Thr Asp Asn Tyr Ala Gln Gly Phe Phe Val Tyr Asp Ser Lys Lys
            450                 455                 460
Ala Gly Ser Ile Thr Thr Ser His Leu Arg Phe Gly Pro Glu Gln Ile
465                 470                 475                 480
Arg Ser Thr Tyr Leu Ile Thr Glu Ala Gln Phe Val Gly Cys His His
                485                 490                 495
Trp Val Phe Leu Glu Met Ile Asp Val Ala Lys Asn Leu Lys Gln Gly
                500                 505                 510
Gly Thr Leu Leu Ile Asn Ser Ala Tyr Ala Pro Asp Val Val Trp Ser
            515                 520                 525
Lys Leu Pro Arg Pro Val Gln Gln His Leu Ile Asp Lys Gln Ala Lys
530                 535                 540
Leu Tyr Thr Ile Asp Ala Tyr Lys Val Ala His Glu Ser Gly Met Gly
545                 550                 555                 560
Gln Arg Ile Asn Thr Ile Met Gln Ala Cys Phe Phe Ala Ile Ser Gly
                565                 570                 575
Val Leu Pro Arg Glu Glu Ala Ile Glu Lys Ile Lys Asp Ala Ile Arg
                580                 585                 590
His Thr Tyr Gly Lys Lys Gly Asp Glu Val Val Gln Gln Asn Ile Lys
            595                 600                 605
Ala Val Asp Asn Thr Leu Ala Asn Leu His Glu Val Lys Ile Gly Ala
            610                 615                 620
Val Ala Asp Ser Thr Lys Glu Leu Arg Ser Pro Ile Val Gly Asp Ala
625                 630                 635                 640
Pro Glu Phe Val Cys Asn Val Leu Ala Lys Ile Ile Ala Gly Glu Gly
                645                 650                 655
Asp Ser Ile Pro Val Ser Lys Leu Pro Ala Asp Gly Thr Tyr Pro Leu
            660                 665                 670
Gly Thr Thr Lys Phe Glu Lys Arg Asn Leu Ala Gln Glu Ile Pro Val
            675                 680                 685
Trp Ala Pro Glu Leu Cys Ile Glu Cys Gly Lys Cys Ser Met Val Cys
690                 695                 700
```

-continued

```
Pro His Ala Ala Ile Arg Ile Lys Val Tyr Glu Pro Lys His Leu Glu
705                 710                 715                 720

Asn Ala Pro Ala Thr Phe Lys Ser Leu Asp Ala Lys Ala Lys Asn Trp
                725                 730                 735

Glu Gly Met Arg Tyr Thr Val Gln Ile Ala Pro Glu Asp Cys Thr Gly
                740                 745                 750

Cys Gln Leu Cys Val Asn Ala Cys Pro Ala Arg Asp Lys Gln Val Glu
                755                 760                 765

Gly Arg Lys Ala Leu Asn Met His Glu Gln Ala Pro Leu Arg Glu Thr
770                 775                 780

Glu Ser Ala Cys Trp Ser Phe Phe Ile Asn Leu Pro Glu Phe Asp Arg
785                 790                 795                 800

Asn Lys Ile Asn Gln Arg Leu Ile Lys Glu Gln Gln Leu Gln Gln Pro
                805                 810                 815

Leu Phe Glu Phe Ser Gly Ala Cys Ser Gly Cys Gly Glu Thr Pro Tyr
                820                 825                 830

Val Lys Leu Met Thr Gln Leu Phe Gly Asp Arg Leu Val Ile Gly Asn
                835                 840                 845

Ala Thr Gly Cys Ser Ser Ile Tyr Gly Gly Asn Leu Pro Thr Thr Pro
850                 855                 860

Tyr Ala Ala Asn Pro Gln Gly Leu Gly Pro Thr Trp Ser Asn Ser Leu
865                 870                 875                 880

Phe Glu Asp Thr Ala Glu Phe Ala Leu Gly Phe Arg Ile Ser Ile Asp
                885                 890                 895

Lys Gln Gln Gln Phe Ala Lys Glu Leu Val Lys Lys Leu Ala Gly Asp
                900                 905                 910

Ile Gly Glu Asn Leu Ala Thr Ala Ile Leu Asn Ala Thr Gln Asn Ser
                915                 920                 925

Glu Pro Glu Ile Phe Glu Gln Arg Glu Arg Val Ala Val Leu Lys Asp
                930                 935                 940

Lys Leu Gln Gln Met Lys Ser Asp Asp Ala Lys Asn Leu Leu Ala Val
945                 950                 955                 960

Ala Asp Met Leu Val Lys Lys Ser Val Trp Ala Val Gly Gly Asp Gly
                965                 970                 975

Trp Ala Tyr Asp Ile Gly Tyr Gly Gly Leu Asp His Val Thr Ala Ser
                980                 985                 990

Gly Lys Asn Val Asn Met Leu Val  Leu Asp Thr Glu Val  Tyr Ser Asn
                995                 1000                1005

Thr Gly  Gly Gln Ala Ser Lys  Ala Thr Pro Lys Ala  Ala Ile Ala
    1010                 1015                1020

Lys Phe  Ala Ala Ala Gly Arg   Ile Ala Thr Lys Lys   Asp Leu Gly
    1025                 1030                 1035

Leu Ile  Ser Met Ser Tyr Gly  Asn Ala Tyr Val Ala  Ser Val Ala
    1040                 1045                 1050

Leu Gly  Ala Arg Asp Glu Gln   Thr Leu Arg Ala Phe   Ile Glu Ala
    1055                 1060                 1065

Glu Ala  Tyr Asp Gly Pro Ser   Ile Ile Ile Ala Tyr   Ser His Cys
    1070                 1075                 1080

Ile Ala  His Gly Phe Asp Leu  Ser Met Gly Leu Glu   His Gln Lys
    1085                 1090                 1095

Ala Ala  Val Asp Ser Gly His  Trp Leu Leu Tyr Arg   Tyr Asn Pro
    1100                 1105                 1110
```

-continued

```
Asp Arg Leu Lys Glu Gly Leu Asn Pro Leu Gln Leu Asp Ser Lys
    1115                1120                1125

Lys Pro Lys Met Pro Val Ala Glu Phe Leu Asn Met Glu Asn Arg
    1130                1135                1140

Phe Arg Ile Leu Lys Lys Thr His Pro Asp Leu Ala Lys Lys Tyr
    1145                1150                1155

Phe Glu Ala Ile Gln His Glu Val Asn Ala Arg Trp Ala His Tyr
    1160                1165                1170

Glu His Leu Ala Asn Arg Ser Ile Glu Gly Glu Ala
    1175                1180                1185

<210> SEQ ID NO 3
<211> LENGTH: 3525
<212> TYPE: DNA
<213> ORGANISM: Escherichia coli
<220> FEATURE:
<221> NAME/KEY: CDS
<222> LOCATION: (1)..(3525)

<400> SEQUENCE: 3
```

| | | |
|---|---|---|
| atg att act att gac ggt aat ggc gcg gtt gct tcg gtc gca ttt cgc<br>Met Ile Thr Ile Asp Gly Asn Gly Ala Val Ala Ser Val Ala Phe Arg<br>1               5                   10                  15 | 48 |
| acc agt gaa gtt atc gcc atc tac cct att acc ccc agt tcc acg atg<br>Thr Ser Glu Val Ile Ala Ile Tyr Pro Ile Thr Pro Ser Ser Thr Met<br>            20                  25                  30 | 96 |
| gca gaa cag gct gat gcc tgg gcc gga aac ggc tta aag aac gtt tgg<br>Ala Glu Gln Ala Asp Ala Trp Ala Gly Asn Gly Leu Lys Asn Val Trp<br>        35                  40                  45 | 144 |
| gga gac aca cca cgc gtg gtt gaa atg cag tcg gaa gcg ggt gct atc<br>Gly Asp Thr Pro Arg Val Val Glu Met Gln Ser Glu Ala Gly Ala Ile<br>    50                  55                  60 | 192 |
| gct acc gtg cat ggc gct ttg cag acg ggt gcc ctt tca aca tcg ttt<br>Ala Thr Val His Gly Ala Leu Gln Thr Gly Ala Leu Ser Thr Ser Phe<br>65                  70                  75                  80 | 240 |
| acg tca tcg cag ggt ttg ctg ctg atg atc ccg acg ctg tac aaa ctg<br>Thr Ser Ser Gln Gly Leu Leu Leu Met Ile Pro Thr Leu Tyr Lys Leu<br>                85                  90                  95 | 288 |
| gca ggc gaa cta aca ccg ttt gtc ctg cat gta gcg gca cgt acc gtt<br>Ala Gly Glu Leu Thr Pro Phe Val Leu His Val Ala Ala Arg Thr Val<br>            100                 105                 110 | 336 |
| gcc aca cat gca ctc tct att ttt ggc gat cat tcc gac gtt atg gcg<br>Ala Thr His Ala Leu Ser Ile Phe Gly Asp His Ser Asp Val Met Ala<br>        115                 120                 125 | 384 |
| gtg cgc cag acg ggt tgc gcg atg ttg tgt gca gca aac gtc cag gaa<br>Val Arg Gln Thr Gly Cys Ala Met Leu Cys Ala Ala Asn Val Gln Glu<br>    130                 135                 140 | 432 |
| gcg caa gac ttt gct ctc att tcg caa atc gcg acg ctg aaa agc cgc<br>Ala Gln Asp Phe Ala Leu Ile Ser Gln Ile Ala Thr Leu Lys Ser Arg<br>145                 150                 155                 160 | 480 |
| gtg cca ttt att cat ttc ttt gat ggt ttc cgc acg tcc cac gaa atc<br>Val Pro Phe Ile His Phe Phe Asp Gly Phe Arg Thr Ser His Glu Ile<br>                165                 170                 175 | 528 |
| aat aaa att gtc ccg ctg gcc gat gac acg att ctt gat ctc atg ccg<br>Asn Lys Ile Val Pro Leu Ala Asp Asp Thr Ile Leu Asp Leu Met Pro<br>            180                 185                 190 | 576 |
| cag gtc gaa att gat gct cat cgc gcc cgg gca ctc aac ccg gaa cat<br>Gln Val Glu Ile Asp Ala His Arg Ala Arg Ala Leu Asn Pro Glu His<br>        195                 200                 205 | 624 |
| ccg gtg atc cgc ggt acg tcc gcc aat cct gac act tat ttc cag tct<br> | 672 |

```
                Pro Val Ile Arg Gly Thr Ser Ala Asn Pro Asp Thr Tyr Phe Gln Ser
                    210                 215                 220 cgc gaa gcc acc aac cca tgg tac aac gcg gtc tat gac cat gtt gaa        720
Arg Glu Ala Thr Asn Pro Trp Tyr Asn Ala Val Tyr Asp His Val Glu
225                 230                 235                 240 cag gcg atg aat gat ttc tct gcc gcg aca ggt cgt cag tat cag ccg        768
Gln Ala Met Asn Asp Phe Ser Ala Ala Thr Gly Arg Gln Tyr Gln Pro
                245                 250                 255 ttt gaa tat tac ggg cat ccg caa gcg gaa cgg gtg att atc ctg atg        816
Phe Glu Tyr Tyr Gly His Pro Gln Ala Glu Arg Val Ile Ile Leu Met
                260                 265                 270 ggc tct gcc att ggc acc tgt gaa gaa gtg gtt gat gaa ttg cta acc        864
Gly Ser Ala Ile Gly Thr Cys Glu Glu Val Val Asp Glu Leu Leu Thr
            275                 280                 285 cgt ggc gaa aaa gtt ggc gtg ctg aaa gtt cgc ctg tac cgc ccc ttc        912
Arg Gly Glu Lys Val Gly Val Leu Lys Val Arg Leu Tyr Arg Pro Phe
        290                 295                 300 tcc gct aaa cat tta ctg caa gct ctg ccg gga tcc gta cgc agc gtg        960
Ser Ala Lys His Leu Leu Gln Ala Leu Pro Gly Ser Val Arg Ser Val
305                 310                 315                 320 gcg gta ctg gac aga acc aaa gaa ccc ggt gcc cag gca gaa ccg ctc       1008
Ala Val Leu Asp Arg Thr Lys Glu Pro Gly Ala Gln Ala Glu Pro Leu
                325                 330                 335 tat ctg gat gta atg acc gca ctg gca gaa gcc ttt aat aat ggc gag       1056
Tyr Leu Asp Val Met Thr Ala Leu Ala Glu Ala Phe Asn Asn Gly Glu
                340                 345                 350 cgc gaa act ctg ccc cgt gtc att ggt ggg cgc tat ggt ctt tca tcc       1104
Arg Glu Thr Leu Pro Arg Val Ile Gly Gly Arg Tyr Gly Leu Ser Ser
                355                 360                 365 aaa gaa ttt ggc cca gac tgt gta ctg gcg gta ttt gcc gag ctc aac       1152
Lys Glu Phe Gly Pro Asp Cys Val Leu Ala Val Phe Ala Glu Leu Asn
370                 375                 380 gcg gct aaa ccg aaa gcg cgc ttt acg gtt ggt att tac gat gat gtg       1200
Ala Ala Lys Pro Lys Ala Arg Phe Thr Val Gly Ile Tyr Asp Asp Val
385                 390                 395                 400 acc aat ctg tca ctg ccg ttg ccg gaa aac acc ctg cca aac tcg gcg       1248
Thr Asn Leu Ser Leu Pro Leu Pro Glu Asn Thr Leu Pro Asn Ser Ala
                405                 410                 415 aaa ctg gaa gcc ttg ttt tat ggc ctt ggt agt gat ggc agc gtt tcc       1296
Lys Leu Glu Ala Leu Phe Tyr Gly Leu Gly Ser Asp Gly Ser Val Ser
                420                 425                 430 gcg acc aaa aac aat atc aag att atc ggt aat tcc acg ccg tgg tac       1344
Ala Thr Lys Asn Asn Ile Lys Ile Ile Gly Asn Ser Thr Pro Trp Tyr
            435                 440                 445 gca cag ggc tat ttt gtt tac gac tcc aaa aag gcg ggc ggc ctg acg       1392
Ala Gln Gly Tyr Phe Val Tyr Asp Ser Lys Lys Ala Gly Gly Leu Thr
        450                 455                 460 gtt tct cac ctt cga gtg agc gaa cag ccg att cgt tcc gct tat ctc       1440
Val Ser His Leu Arg Val Ser Glu Gln Pro Ile Arg Ser Ala Tyr Leu
465                 470                 475                 480 att tcc cag gct gat ttt gtt ggc tgc cac cag ttg cag ttt atc gat       1488
Ile Ser Gln Ala Asp Phe Val Gly Cys His Gln Leu Gln Phe Ile Asp
                485                 490                 495 aaa tat cag atg gct gag cgt tta aaa cct ggc ggc att ttc ctg ctc       1536
Lys Tyr Gln Met Ala Glu Arg Leu Lys Pro Gly Gly Ile Phe Leu Leu
                500                 505                 510 aac acg ccg tac agc gca gat gaa gtg tgg tcg cgc ttg ccg caa gaa       1584
Asn Thr Pro Tyr Ser Ala Asp Glu Val Trp Ser Arg Leu Pro Gln Glu
                515                 520                 525
```

-continued

| | | | | | | | | | | | | | | | |
|---|---|---|---|---|---|---|---|---|---|---|---|---|---|---|---|
| gtt | cag | gcc | gtg | tta | aac | cag | aaa | aaa | gcg | cgc | ttc | tat | gtg | att | aac | 1632 |
| Val | Gln | Ala | Val | Leu | Asn | Gln | Lys | Lys | Ala | Arg | Phe | Tyr | Val | Ile | Asn |
| | 530 | | | | 535 | | | | | 540 | | | | | | gcg gca aaa atc gcc cgc gaa tgt ggc ctg gcg gcc cgt att aat acc   1680
Ala Ala Lys Ile Ala Arg Glu Cys Gly Leu Ala Ala Arg Ile Asn Thr
545                 550                 555                 560 gtc atg cag atg gct ttt ttc cat ctg acg caa att ctg cct ggc gat   1728
Val Met Gln Met Ala Phe Phe His Leu Thr Gln Ile Leu Pro Gly Asp
                565                 570                 575 agc gcc ctc gca gaa ttg cag ggt gcg att gcc aaa agt tac agt agc   1776
Ser Ala Leu Ala Glu Leu Gln Gly Ala Ile Ala Lys Ser Tyr Ser Ser
            580                 585                 590 aaa ggc cag gat ctg gtg gaa cgc aac tgg cag gct ctg gcg ctg gcg   1824
Lys Gly Gln Asp Leu Val Glu Arg Asn Trp Gln Ala Leu Ala Leu Ala
        595                 600                 605 cgt gaa tcc gta gaa gaa gtt ccg ttg caa ccg gta aat ccg cac agc   1872
Arg Glu Ser Val Glu Glu Val Pro Leu Gln Pro Val Asn Pro His Ser
610                 615                 620 gcc aat cga ccg cca gtg gtt tcc gat gcc gcc cct gat ttc gtg aaa   1920
Ala Asn Arg Pro Pro Val Val Ser Asp Ala Ala Pro Asp Phe Val Lys
625                 630                 635                 640 acc gta acc gct gcg atg ctc gcc ggg ctt ggt gac gcc ctc ccc gtt   1968
Thr Val Thr Ala Ala Met Leu Ala Gly Leu Gly Asp Ala Leu Pro Val
                645                 650                 655 tcg gcg ctg ccg cca gac ggc acc tgg ccg atg ggc act acg cgc tgg   2016
Ser Ala Leu Pro Pro Asp Gly Thr Trp Pro Met Gly Thr Thr Arg Trp
            660                 665                 670 gaa aaa cgc aat atc gcc gaa gag atc ccc atc tgg aaa gag gaa ctc   2064
Glu Lys Arg Asn Ile Ala Glu Glu Ile Pro Ile Trp Lys Glu Glu Leu
        675                 680                 685 tgt acc caa tgt aac cac tgc gtt gcc gct tgc cca cac tca gct att   2112
Cys Thr Gln Cys Asn His Cys Val Ala Ala Cys Pro His Ser Ala Ile
690                 695                 700 cgc gca aaa gtg gtg ccg cct gaa gcg atg gaa aac gcc cct gcc agc   2160
Arg Ala Lys Val Val Pro Pro Glu Ala Met Glu Asn Ala Pro Ala Ser
705                 710                 715                 720 ctg cat tcg ctg gat gtg aaa tcg cgt gat atg cgc ggg cag aaa tat   2208
Leu His Ser Leu Asp Val Lys Ser Arg Asp Met Arg Gly Gln Lys Tyr
                725                 730                 735 gtc ttg cag gtg gca ccg gaa gat tgc acc ggt tgt aac ctg tgc gtc   2256
Val Leu Gln Val Ala Pro Glu Asp Cys Thr Gly Cys Asn Leu Cys Val
            740                 745                 750 gaa gtt tgc ccg gcg aaa gac cgt cag aat cca gag att aaa gcc atc   2304
Glu Val Cys Pro Ala Lys Asp Arg Gln Asn Pro Glu Ile Lys Ala Ile
        755                 760                 765 aat atg atg tct cgc ctg gaa cat gtc gaa gaa gag aaa atc aat tac   2352
Asn Met Met Ser Arg Leu Glu His Val Glu Glu Glu Lys Ile Asn Tyr
770                 775                 780 gat ttc ttc ctc aac ctg cca gaa atc gac cgt agc aaa ctg gaa cgt   2400
Asp Phe Phe Leu Asn Leu Pro Glu Ile Asp Arg Ser Lys Leu Glu Arg
785                 790                 795                 800 att gat att cgt aca tcg cag ctg att aca ccg ctg ttt gaa tat tca   2448
Ile Asp Ile Arg Thr Ser Gln Leu Ile Thr Pro Leu Phe Glu Tyr Ser
                805                 810                 815 ggt gct tgc tcc ggt tgt ggc gag acg ccg tat att aaa tta ctg act   2496
Gly Ala Cys Ser Gly Cys Gly Glu Thr Pro Tyr Ile Lys Leu Leu Thr
            820                 825                 830 cag ctc tat ggc gac cgg atg ttg atc gct aac gcc act ggc tgt tct   2544
Gln Leu Tyr Gly Asp Arg Met Leu Ile Ala Asn Ala Thr Gly Cys Ser
        835                 840                 845

-continued

| | |
|---|---|
| tca att tat ggc ggt aac ctg ccc tct aca ccg tat acc acc gat gcc<br>Ser Ile Tyr Gly Gly Asn Leu Pro Ser Thr Pro Tyr Thr Thr Asp Ala<br>850                           855                       860 | 2592 |
| aac ggt cgt ggg ccg gca tgg gcg aac tct cta ttt gaa gat aat gcc<br>Asn Gly Arg Gly Pro Ala Trp Ala Asn Ser Leu Phe Glu Asp Asn Ala<br>865                         870                     875                     880 | 2640 |
| gaa ttt ggc ctt ggt ttc cgc ctg acg gtc gat caa cac cgt gtc cgc<br>Glu Phe Gly Leu Gly Phe Arg Leu Thr Val Asp Gln His Arg Val Arg<br>                    885                     890                     895 | 2688 |
| gtg ctg cgt ctg ctg gat caa ttt gcc gat aaa atc ccg gcg gaa tta<br>Val Leu Arg Leu Leu Asp Gln Phe Ala Asp Lys Ile Pro Ala Glu Leu<br>900                         905                       910 | 2736 |
| ctg acg gcg ttg aaa tca gac gcc acg cca gag gtt cgt cgt gaa cag<br>Leu Thr Ala Leu Lys Ser Asp Ala Thr Pro Glu Val Arg Arg Glu Gln<br>               915                     920                     925 | 2784 |
| gtt gca gct tta cgc cag caa ctc aac gat gtt gcc gaa gca cat gaa<br>Val Ala Ala Leu Arg Gln Gln Leu Asn Asp Val Ala Glu Ala His Glu<br>930                         935                       940 | 2832 |
| ctg cta cgt gat gca gat gca ctg gtg gaa aaa tca atc tgg ctg att<br>Leu Leu Arg Asp Ala Asp Ala Leu Val Glu Lys Ser Ile Trp Leu Ile<br>945                         950                     955                     960 | 2880 |
| ggt ggt gat ggc tgg gct tac gat atc ggc ttt ggc ggt ctg gat cat<br>Gly Gly Asp Gly Trp Ala Tyr Asp Ile Gly Phe Gly Gly Leu Asp His<br>                    965                     970                     975 | 2928 |
| gta ttg agt ttg acg gaa aac gtc aac att ctg gtg ctg gat acg caa<br>Val Leu Ser Leu Thr Glu Asn Val Asn Ile Leu Val Leu Asp Thr Gln<br>               980                     985                     990 | 2976 |
| tgc tat tcc aac acc ggt ggt cag gcg tcg aaa gcg aca ccg ctg ggt<br>Cys Tyr Ser Asn Thr Gly Gly Gln Ala Ser Lys Ala Thr Pro Leu Gly<br>               995                    1000                  1005 | 3024 |
| gca gta act aaa ttt ggc gag cac ggc aaa cgt aaa gcg cgt aaa gat<br>Ala Val Thr Lys Phe Gly Glu His Gly Lys Arg Lys Ala Arg Lys Asp<br>    1010                    1015                    1020 | 3072 |
| ctt ggc gtc agt atg atg atg tac ggt cat gtt tat gtg gcg cag att<br>Leu Gly Val Ser Met Met Met Tyr Gly His Val Tyr Val Ala Gln Ile<br>1025                       1030                    1035                    1040 | 3120 |
| tct ctc ggc gcg cag ctg aac cag acg gtg aaa gcg att cag gaa gcg<br>Ser Leu Gly Ala Gln Leu Asn Gln Thr Val Lys Ala Ile Gln Glu Ala<br>                  1045                    1050                    1055 | 3168 |
| gaa gcg tat ccg ggg cca tcg ctg atc att gct tat agc ccg tgt gaa<br>Glu Ala Tyr Pro Gly Pro Ser Leu Ile Ile Ala Tyr Ser Pro Cys Glu<br>             1060                    1065                    1070 | 3216 |
| gag cat ggt tac gat ctg gca ctc agc cac gac cag atg cgc caa ctc<br>Glu His Gly Tyr Asp Leu Ala Leu Ser His Asp Gln Met Arg Gln Leu<br>          1075                    1080                    1085 | 3264 |
| aca gct acc ggc ttc tgg ccg cta tat cgc ttt gat ccg cgt cgt gcc<br>Thr Ala Thr Gly Phe Trp Pro Leu Tyr Arg Phe Asp Pro Arg Arg Ala<br>        1090                    1095                    1100 | 3312 |
| gat gaa ggc aaa ctg ccg ctg gcc ttg gat tca cgc ccg tca gaa<br>Asp Glu Gly Lys Leu Pro Leu Ala Leu Asp Ser Arg Pro Pro Ser Glu<br>1105                     1110                    1115                    1120 | 3360 |
| gca ccg gaa gaa acg tta ctt cac gag caa cgt ttc cgt cgg ctg aat<br>Ala Pro Glu Glu Thr Leu Leu His Glu Gln Arg Phe Arg Arg Leu Asn<br>                  1125                    1130                    1135 | 3408 |
| tcg cag cag cca gaa gtg gca gaa cag tta tgg aaa gat gct gca gct<br>Ser Gln Gln Pro Glu Val Ala Glu Gln Leu Trp Lys Asp Ala Ala Ala<br>             1140                    1145                    1150 | 3456 |
| gat ttg caa aaa cgc tat gac ttc ctg gca caa atg gcc gga aaa gcg<br>Asp Leu Gln Lys Arg Tyr Asp Phe Leu Ala Gln Met Ala Gly Lys Ala | 3504 |

-continued

```
       1155              1160              1165
gaa aaa agc aac acc gat taa                                       3525
Glu Lys Ser Asn Thr Asp
    1170
```

<210> SEQ ID NO 4
<211> LENGTH: 1174
<212> TYPE: PRT
<213> ORGANISM: Escherichia coli

<400> SEQUENCE: 4

```
Met Ile Thr Ile Asp Gly Asn Gly Ala Val Ser Val Ala Phe Arg
1               5                   10                  15

Thr Ser Glu Val Ile Ala Ile Tyr Pro Ile Thr Pro Ser Ser Thr Met
                20                  25                  30

Ala Glu Gln Ala Asp Ala Trp Ala Gly Asn Gly Leu Lys Asn Val Trp
            35                  40                  45

Gly Asp Thr Pro Arg Val Val Glu Met Gln Ser Glu Ala Gly Ala Ile
    50                  55                  60

Ala Thr Val His Gly Ala Leu Gln Thr Gly Ala Leu Ser Thr Ser Phe
65                  70                  75                  80

Thr Ser Ser Gln Gly Leu Leu Leu Met Ile Pro Thr Leu Tyr Lys Leu
                85                  90                  95

Ala Gly Glu Leu Thr Pro Phe Val Leu His Val Ala Ala Arg Thr Val
            100                 105                 110

Ala Thr His Ala Leu Ser Ile Phe Gly Asp His Ser Asp Val Met Ala
        115                 120                 125

Val Arg Gln Thr Gly Cys Ala Met Leu Cys Ala Ala Asn Val Gln Glu
    130                 135                 140

Ala Gln Asp Phe Ala Leu Ile Ser Gln Ile Ala Thr Leu Lys Ser Arg
145                 150                 155                 160

Val Pro Phe Ile His Phe Phe Asp Gly Phe Arg Thr Ser His Glu Ile
                165                 170                 175

Asn Lys Ile Val Pro Leu Ala Asp Asp Thr Ile Leu Asp Leu Met Pro
            180                 185                 190

Gln Val Glu Ile Asp Ala His Arg Ala Arg Ala Leu Asn Pro Glu His
        195                 200                 205

Pro Val Ile Arg Gly Thr Ser Ala Asn Pro Asp Thr Tyr Phe Gln Ser
    210                 215                 220

Arg Glu Ala Thr Asn Pro Trp Tyr Asn Ala Val Tyr Asp His Val Glu
225                 230                 235                 240

Gln Ala Met Asn Asp Phe Ser Ala Ala Thr Gly Arg Gln Tyr Gln Pro
                245                 250                 255

Phe Glu Tyr Tyr Gly His Pro Gln Ala Glu Arg Val Ile Ile Leu Met
            260                 265                 270

Gly Ser Ala Ile Gly Thr Cys Glu Glu Val Val Asp Glu Leu Leu Thr
        275                 280                 285

Arg Gly Glu Lys Val Gly Val Leu Lys Val Arg Leu Tyr Arg Pro Phe
    290                 295                 300

Ser Ala Lys His Leu Leu Gln Ala Leu Pro Gly Ser Val Arg Ser Val
305                 310                 315                 320

Ala Val Leu Asp Arg Thr Lys Glu Pro Gly Ala Gln Ala Glu Pro Leu
                325                 330                 335

Tyr Leu Asp Val Met Thr Ala Leu Ala Glu Ala Phe Asn Asn Gly Glu
            340                 345                 350
```

```
Arg Glu Thr Leu Pro Arg Val Ile Gly Gly Arg Tyr Gly Leu Ser Ser
            355                 360                 365

Lys Glu Phe Gly Pro Asp Cys Val Leu Ala Val Phe Ala Glu Leu Asn
    370                 375                 380

Ala Ala Lys Pro Lys Ala Arg Phe Thr Val Gly Ile Tyr Asp Asp Val
385                 390                 395                 400

Thr Asn Leu Ser Leu Pro Leu Pro Glu Asn Thr Leu Pro Asn Ser Ala
            405                 410                 415

Lys Leu Glu Ala Leu Phe Tyr Gly Leu Gly Ser Asp Gly Ser Val Ser
            420                 425                 430

Ala Thr Lys Asn Asn Ile Lys Ile Ile Gly Asn Ser Thr Pro Trp Tyr
            435                 440                 445

Ala Gln Gly Tyr Phe Val Tyr Asp Ser Lys Lys Ala Gly Gly Leu Thr
            450                 455                 460

Val Ser His Leu Arg Val Ser Glu Gln Pro Ile Arg Ser Ala Tyr Leu
465                 470                 475                 480

Ile Ser Gln Ala Asp Phe Val Gly Cys His Gln Leu Gln Phe Ile Asp
            485                 490                 495

Lys Tyr Gln Met Ala Glu Arg Leu Lys Pro Gly Gly Ile Phe Leu Leu
            500                 505                 510

Asn Thr Pro Tyr Ser Ala Asp Glu Val Trp Ser Arg Leu Pro Gln Glu
            515                 520                 525

Val Gln Ala Val Leu Asn Gln Lys Lys Ala Arg Phe Tyr Val Ile Asn
530                 535                 540

Ala Ala Lys Ile Ala Arg Glu Cys Gly Leu Ala Ala Arg Ile Asn Thr
545                 550                 555                 560

Val Met Gln Met Ala Phe Phe His Leu Thr Gln Ile Leu Pro Gly Asp
            565                 570                 575

Ser Ala Leu Ala Glu Leu Gln Gly Ala Ile Ala Lys Ser Tyr Ser Ser
            580                 585                 590

Lys Gly Gln Asp Leu Val Glu Arg Asn Trp Gln Ala Leu Ala Leu Ala
            595                 600                 605

Arg Glu Ser Val Glu Glu Val Pro Leu Gln Pro Val Asn Pro His Ser
    610                 615                 620

Ala Asn Arg Pro Pro Val Val Ser Asp Ala Ala Pro Asp Phe Val Lys
625                 630                 635                 640

Thr Val Thr Ala Ala Met Leu Ala Gly Leu Gly Asp Ala Leu Pro Val
            645                 650                 655

Ser Ala Leu Pro Pro Asp Gly Thr Trp Pro Met Gly Thr Thr Arg Trp
            660                 665                 670

Glu Lys Arg Asn Ile Ala Glu Ile Pro Ile Trp Lys Glu Glu Leu
            675                 680                 685

Cys Thr Gln Cys Asn His Cys Val Ala Ala Cys Pro His Ser Ala Ile
            690                 695                 700

Arg Ala Lys Val Val Pro Pro Glu Ala Met Glu Asn Ala Pro Ala Ser
705                 710                 715                 720

Leu His Ser Leu Asp Val Lys Ser Arg Asp Met Arg Gly Gln Lys Tyr
            725                 730                 735

Val Leu Gln Val Ala Pro Glu Asp Cys Thr Gly Cys Asn Leu Cys Val
            740                 745                 750

Glu Val Cys Pro Ala Lys Asp Arg Gln Asn Pro Glu Ile Lys Ala Ile
            755                 760                 765
```

-continued

```
Asn Met Met Ser Arg Leu Glu His Val Glu Glu Lys Ile Asn Tyr
    770                 775                 780

Asp Phe Phe Leu Asn Leu Pro Glu Ile Asp Arg Ser Lys Leu Glu Arg
785                 790                 795                 800

Ile Asp Ile Arg Thr Ser Gln Leu Ile Thr Pro Leu Phe Glu Tyr Ser
                    805                 810                 815

Gly Ala Cys Ser Gly Cys Gly Thr Pro Tyr Ile Lys Leu Leu Thr
                820                 825                 830

Gln Leu Tyr Gly Asp Arg Met Leu Ile Ala Asn Ala Thr Gly Cys Ser
            835                 840                 845

Ser Ile Tyr Gly Gly Asn Leu Pro Ser Thr Pro Tyr Thr Thr Asp Ala
    850                 855                 860

Asn Gly Arg Gly Pro Ala Trp Ala Asn Ser Leu Phe Glu Asp Asn Ala
865                 870                 875                 880

Glu Phe Gly Leu Gly Phe Arg Leu Thr Val Asp Gln His Arg Val Arg
                    885                 890                 895

Val Leu Arg Leu Leu Asp Gln Phe Ala Asp Lys Ile Pro Ala Glu Leu
                900                 905                 910

Leu Thr Ala Leu Lys Ser Asp Ala Thr Pro Glu Val Arg Arg Glu Gln
            915                 920                 925

Val Ala Ala Leu Arg Gln Gln Leu Asn Asp Val Ala Glu Ala His Glu
    930                 935                 940

Leu Leu Arg Asp Ala Asp Ala Leu Val Glu Lys Ser Ile Trp Leu Ile
945                 950                 955                 960

Gly Gly Asp Gly Trp Ala Tyr Asp Ile Gly Phe Gly Gly Leu Asp His
                    965                 970                 975

Val Leu Ser Leu Thr Glu Asn Val Asn Ile Leu Val Leu Asp Thr Gln
                980                 985                 990

Cys Tyr Ser Asn Thr Gly Gly Gln Ala Ser Lys Ala Thr Pro Leu Gly
            995                 1000                1005

Ala Val Thr Lys Phe Gly Glu His Gly Lys Arg Lys Ala Arg Lys
    1010                1015                1020

Asp Leu Gly Val Ser Met Met Met Tyr Gly His Val Tyr Val Ala
    1025                1030                1035

Gln Ile Ser Leu Gly Ala Gln Leu Asn Gln Thr Val Lys Ala Ile
    1040                1045                1050

Gln Glu Ala Glu Ala Tyr Pro Gly Pro Ser Leu Ile Ile Ala Tyr
    1055                1060                1065

Ser Pro Cys Glu Glu His Gly Tyr Asp Leu Ala Leu Ser His Asp
    1070                1075                1080

Gln Met Arg Gln Leu Thr Ala Thr Gly Phe Trp Pro Leu Tyr Arg
    1085                1090                1095

Phe Asp Pro Arg Arg Ala Asp Glu Gly Lys Leu Pro Leu Ala Leu
    1100                1105                1110

Asp Ser Arg Pro Pro Ser Glu Ala Pro Glu Glu Thr Leu Leu His
    1115                1120                1125

Glu Gln Arg Phe Arg Arg Leu Asn Ser Gln Gln Pro Glu Val Ala
    1130                1135                1140

Glu Gln Leu Trp Lys Asp Ala Ala Asp Leu Gln Lys Arg Tyr
    1145                1150                1155

Asp Phe Leu Ala Gln Met Ala Gly Lys Ala Glu Lys Ser Asn Thr
    1160                1165                1170

Asp
```

```
<210> SEQ ID NO 5
<211> LENGTH: 5412
<212> TYPE: DNA
<213> ORGANISM: Euglena gracilis
<220> FEATURE:
<221> NAME/KEY: CDS
<222> LOCATION: (1)..(5412)

<400> SEQUENCE: 5 atg aag cag tct gtc cgc cca att att tcc aat gta ctg cgc aag gag      48
Met Lys Gln Ser Val Arg Pro Ile Ile Ser Asn Val Leu Arg Lys Glu
1               5                  10                  15 gtt gct ctg tac tca aca atc att gga caa gac aag ggg aag gaa cca      96
Val Ala Leu Tyr Ser Thr Ile Ile Gly Gln Asp Lys Gly Lys Glu Pro
            20                  25                  30 act ggt cga aca tac acc agt ggc cca aaa ccg gca tct cac att gaa     144
Thr Gly Arg Thr Tyr Thr Ser Gly Pro Lys Pro Ala Ser His Ile Glu
        35                  40                  45 gtt ccc cat cat gtg act gtg cct gcc act gac cgc acc ccg aat ccc     192
Val Pro His His Val Thr Val Pro Ala Thr Asp Arg Thr Pro Asn Pro
50                  55                  60 gat gct caa ttc ttt cag tct gta gat ggg tca caa gcc acc agt cac     240
Asp Ala Gln Phe Phe Gln Ser Val Asp Gly Ser Gln Ala Thr Ser His
65                  70                  75                  80 gtt gcg tac gct ctg tct gac aca gcg ttc att tac cca att aca ccc     288
Val Ala Tyr Ala Leu Ser Asp Thr Ala Phe Ile Tyr Pro Ile Thr Pro
                85                  90                  95 agt tct gtg atg ggc gag ctg gct gat gtt tgg atg gct caa ggg agg     336
Ser Ser Val Met Gly Glu Leu Ala Asp Val Trp Met Ala Gln Gly Arg
            100                 105                 110 aag aac gcc ttt ggt cag gtt gtg gat gtc cgt gag atg caa tct gag     384
Lys Asn Ala Phe Gly Gln Val Val Asp Val Arg Glu Met Gln Ser Glu
        115                 120                 125 gct gga gcc gca ggc gcc ctg cat ggg gca ctg gct gct gga gct att     432
Ala Gly Ala Ala Gly Ala Leu His Gly Ala Leu Ala Ala Gly Ala Ile
    130                 135                 140 gct aca acc ttc act gcc tct caa ggg ttg ttg ttg atg att ccc aac     480
Ala Thr Thr Phe Thr Ala Ser Gln Gly Leu Leu Leu Met Ile Pro Asn
145                 150                 155                 160 atg tat aag att gca ggt gag ctg atg ccc tct gtc atc cac gtt gca     528
Met Tyr Lys Ile Ala Gly Glu Leu Met Pro Ser Val Ile His Val Ala
                165                 170                 175 gcc cga gag ctt gca ggc cac gct ctg tcc att ttt gga gga cac gct     576
Ala Arg Glu Leu Ala Gly His Ala Leu Ser Ile Phe Gly Gly His Ala
            180                 185                 190 gat gtc atg gct gtc cgc caa aca gga tgg gct atg ctg tgc tcc cac     624
Asp Val Met Ala Val Arg Gln Thr Gly Trp Ala Met Leu Cys Ser His
        195                 200                 205 aca gtg cag cag tct cac gac atg gct ctc atc tcc cac gtg gcc acc     672
Thr Val Gln Gln Ser His Asp Met Ala Leu Ile Ser His Val Ala Thr
    210                 215                 220 ctc aag tcc agc atc ccc ttc gtt cac ttc ttt gat ggt ttc cgc aca     720
Leu Lys Ser Ser Ile Pro Phe Val His Phe Phe Asp Gly Phe Arg Thr
225                 230                 235                 240 agc cac gaa gtg aac aaa atc aaa atg ctg cct tat gca gaa ctg aag     768
Ser His Glu Val Asn Lys Ile Lys Met Leu Pro Tyr Ala Glu Leu Lys
                245                 250                 255 aaa ctg gtg cct cct ggc acc atg gaa cag cac tgg gct cgt tcg ctg     816
Lys Leu Val Pro Pro Gly Thr Met Glu Gln His Trp Ala Arg Ser Leu
            260                 265                 270
```

```
aac ccc atg cac ccc acc atc cga gga aca aac cag tct gca gac atc        864
Asn Pro Met His Pro Thr Ile Arg Gly Thr Asn Gln Ser Ala Asp Ile
    275                 280                 285 tac ttc cag aat atg gaa agt gca aac cag tac tac act gat ctg gcc        912
Tyr Phe Gln Asn Met Glu Ser Ala Asn Gln Tyr Tyr Thr Asp Leu Ala
290                 295                 300 gag gtc gtt cag gag aca atg gac gaa gtt gca cca tac atc ggt cgc        960
Glu Val Val Gln Glu Thr Met Asp Glu Val Ala Pro Tyr Ile Gly Arg
305                 310                 315                 320 cac tac aag atc ttt gag tat gtt ggt gca cca gat gca gaa gaa gtg       1008
His Tyr Lys Ile Phe Glu Tyr Val Gly Ala Pro Asp Ala Glu Glu Val
                325                 330                 335 aca gtg ctc atg ggt tct ggt gca acc aca gtc aac gag gca gtg gac       1056
Thr Val Leu Met Gly Ser Gly Ala Thr Thr Val Asn Glu Ala Val Asp
    340                 345                 350 ctt ctt gtg aag cgt gga aag aag gtt ggt gca gtc ttg gtg cac ctc       1104
Leu Leu Val Lys Arg Gly Lys Lys Val Gly Ala Val Leu Val His Leu
355                 360                 365 tac cga cca tgg tca aca aag gca ttt gaa aag gtc ctg ccc aag aca       1152
Tyr Arg Pro Trp Ser Thr Lys Ala Phe Glu Lys Val Leu Pro Lys Thr
370                 375                 380 gtg aag cgc att gct gct ctg gat cgc tgc aag gag gtg act gca ctg       1200
Val Lys Arg Ile Ala Ala Leu Asp Arg Cys Lys Glu Val Thr Ala Leu
385                 390                 395                 400 ggt gag cct ctg tat ctg gat gtg tcg gca act ctg aat ttg ttc ccg       1248
Gly Glu Pro Leu Tyr Leu Asp Val Ser Ala Thr Leu Asn Leu Phe Pro
                405                 410                 415 gaa cgc cag aat gtg aaa gtc att gga gga cgt tac gga ttg ggc tca       1296
Glu Arg Gln Asn Val Lys Val Ile Gly Gly Arg Tyr Gly Leu Gly Ser
    420                 425                 430 aag gat ttc atc ccg gag cat gcc ctg gca att tac gcc aac ttg gcc       1344
Lys Asp Phe Ile Pro Glu His Ala Leu Ala Ile Tyr Ala Asn Leu Ala
435                 440                 445 agc gag aac ccc att caa aga ttc act gtg ggt atc aca gat gat gtc       1392
Ser Glu Asn Pro Ile Gln Arg Phe Thr Val Gly Ile Thr Asp Asp Val
450                 455                 460 act ggc aca tcc gtt cct ttc gtc aac gag cgt gtt gac acg ttg ccc       1440
Thr Gly Thr Ser Val Pro Phe Val Asn Glu Arg Val Asp Thr Leu Pro
465                 470                 475                 480 gag ggc acc cgc cag tgt gtc ttc tgg gga att ggt tca gat gga aca       1488
Glu Gly Thr Arg Gln Cys Val Phe Trp Gly Ile Gly Ser Asp Gly Thr
                485                 490                 495 gtg gga gcc aat cgc tct gcc gtg aga atc att gga gac aac agc gat       1536
Val Gly Ala Asn Arg Ser Ala Val Arg Ile Ile Gly Asp Asn Ser Asp
    500                 505                 510 ttg atg gtt cag gcc tac ttc caa ttt gat gct ttc aag tca ggt ggt       1584
Leu Met Val Gln Ala Tyr Phe Gln Phe Asp Ala Phe Lys Ser Gly Gly
515                 520                 525 gtc act tcc tcg cat ctc cgt ttt gga cca aag ccc atc aca gcg caa       1632
Val Thr Ser Ser His Leu Arg Phe Gly Pro Lys Pro Ile Thr Ala Gln
530                 535                 540 tac ctt gtt acc aat gct gac tac atc gcg tgc cac ttc cag gag tat       1680
Tyr Leu Val Thr Asn Ala Asp Tyr Ile Ala Cys His Phe Gln Glu Tyr
545                 550                 555                 560 gtc aag cgc ttt gac atg ctt gat gcc atc cgt gag ggg ggc acc ttt       1728
Val Lys Arg Phe Asp Met Leu Asp Ala Ile Arg Glu Gly Gly Thr Phe
                565                 570                 575 gtt ctc aat tct cgg tgg acc acg gag gac atg gag aag gag att ccg       1776
Val Leu Asn Ser Arg Trp Thr Thr Glu Asp Met Glu Lys Glu Ile Pro
```

-continued

|  |  |  |  |  |  |  |  |  |  |  |  |  |  |  |  |
|---|---|---|---|---|---|---|---|---|---|---|---|---|---|---|---|
|  |  | 580 |  |  |  |  | 585 |  |  |  |  | 590 |  |  |  |
| gct | gac | ttc | cgg | cgc | aag | ctg | gca | cag | aag | aag | gtc | cgc | ttc | tac | aat | 1824 |
| Ala | Asp | Phe | Arg | Arg | Lys | Leu | Ala | Gln | Lys | Lys | Val | Arg | Phe | Tyr | Asn |  |
|  |  | 595 |  |  |  |  | 600 |  |  |  |  | 605 |  |  |  |  |
| gtg | gat | gct | cga | aag | atc | tgt | gac | agt | ttt | ggt | ctt | ggg | aag | cgc | atc | 1872 |
| Val | Asp | Ala | Arg | Lys | Ile | Cys | Asp | Ser | Phe | Gly | Leu | Gly | Lys | Arg | Ile |  |
|  | 610 |  |  |  |  | 615 |  |  |  |  | 620 |  |  |  |  |  |
| aat | atg | ctg | atg | cag | gct | tgt | ttc | ttc | aag | ctg | tct | ggg | gtg | ctc | cca | 1920 |
| Asn | Met | Leu | Met | Gln | Ala | Cys | Phe | Phe | Lys | Leu | Ser | Gly | Val | Leu | Pro |  |
| 625 |  |  |  |  | 630 |  |  |  |  | 635 |  |  |  |  | 640 |  |
| ctg | gcc | gaa | gct | cag | cgg | ctg | ctg | aac | gag | tcc | att | gtg | cat | gag | tat | 1968 |
| Leu | Ala | Glu | Ala | Gln | Arg | Leu | Leu | Asn | Glu | Ser | Ile | Val | His | Glu | Tyr |  |
|  |  |  |  | 645 |  |  |  |  | 650 |  |  |  |  | 655 |  |  |
| gga | aag | aag | ggt | ggc | aag | gtg | gtg | gag | atg | aac | caa | gca | gtg | gtg | aat | 2016 |
| Gly | Lys | Lys | Gly | Gly | Lys | Val | Val | Glu | Met | Asn | Gln | Ala | Val | Val | Asn |  |
|  |  |  | 660 |  |  |  |  | 665 |  |  |  |  | 670 |  |  |  |
| gct | gtc | ttt | gct | ggt | gac | ctg | ccc | cag | gaa | gtt | caa | gtc | cct | gcc | gcc | 2064 |
| Ala | Val | Phe | Ala | Gly | Asp | Leu | Pro | Gln | Glu | Val | Gln | Val | Pro | Ala | Ala |  |
|  |  | 675 |  |  |  |  | 680 |  |  |  |  | 685 |  |  |  |  |
| tgg | gca | aac | gca | gtt | gat | aca | tcc | acc | cgt | acc | ccc | acc | ggg | att | gag | 2112 |
| Trp | Ala | Asn | Ala | Val | Asp | Thr | Ser | Thr | Arg | Thr | Pro | Thr | Gly | Ile | Glu |  |
|  | 690 |  |  |  |  | 695 |  |  |  |  | 700 |  |  |  |  |  |
| ttt | gtt | gac | aag | atc | atg | cgc | ccg | ctg | atg | gat | ttc | aag | ggt | gac | cag | 2160 |
| Phe | Val | Asp | Lys | Ile | Met | Arg | Pro | Leu | Met | Asp | Phe | Lys | Gly | Asp | Gln |  |
| 705 |  |  |  |  | 710 |  |  |  |  | 715 |  |  |  |  | 720 |  |
| ctc | cca | gtc | agt | gtg | atg | act | cct | ggt | gga | acc | ttc | cct | gtc | ggg | aca | 2208 |
| Leu | Pro | Val | Ser | Val | Met | Thr | Pro | Gly | Gly | Thr | Phe | Pro | Val | Gly | Thr |  |
|  |  |  |  | 725 |  |  |  |  | 730 |  |  |  |  | 735 |  |  |
| aca | cag | tat | gcc | aag | cgt | gca | att | gct | gct | ttc | att | ccc | cag | tgg | att | 2256 |
| Thr | Gln | Tyr | Ala | Lys | Arg | Ala | Ile | Ala | Ala | Phe | Ile | Pro | Gln | Trp | Ile |  |
|  |  |  | 740 |  |  |  |  | 745 |  |  |  |  | 750 |  |  |  |
| cct | gcc | aac | tgc | aca | cag | tgc | aac | tat | tgt | tcg | tat | gtt | tgc | ccc | cac | 2304 |
| Pro | Ala | Asn | Cys | Thr | Gln | Cys | Asn | Tyr | Cys | Ser | Tyr | Val | Cys | Pro | His |  |
|  |  | 755 |  |  |  |  | 760 |  |  |  |  | 765 |  |  |  |  |
| gcc | acc | atc | cga | cct | ttc | gtg | ctg | aca | gac | cag | gag | gtg | cag | ctg | gcc | 2352 |
| Ala | Thr | Ile | Arg | Pro | Phe | Val | Leu | Thr | Asp | Gln | Glu | Val | Gln | Leu | Ala |  |
|  | 770 |  |  |  |  | 775 |  |  |  |  | 780 |  |  |  |  |  |
| ccg | gag | agc | ttt | gtg | aca | cgc | aag | gcg | aag | ggt | gat | tac | cag | ggg | atg | 2400 |
| Pro | Glu | Ser | Phe | Val | Thr | Arg | Lys | Ala | Lys | Gly | Asp | Tyr | Gln | Gly | Met |  |
| 785 |  |  |  |  | 790 |  |  |  |  | 795 |  |  |  |  | 800 |  |
| aat | ttc | cgc | atc | caa | gtt | gct | cct | gag | gat | tgc | act | ggc | tgc | cag | gtg | 2448 |
| Asn | Phe | Arg | Ile | Gln | Val | Ala | Pro | Glu | Asp | Cys | Thr | Gly | Cys | Gln | Val |  |
|  |  |  |  | 805 |  |  |  |  | 810 |  |  |  |  | 815 |  |  |
| tgc | gtg | gag | acg | tgc | ccc | gat | gat | gcc | ctg | gag | atg | acc | gac | gct | ttc | 2496 |
| Cys | Val | Glu | Thr | Cys | Pro | Asp | Asp | Ala | Leu | Glu | Met | Thr | Asp | Ala | Phe |  |
|  |  |  | 820 |  |  |  |  | 825 |  |  |  |  | 830 |  |  |  |
| acc | gcc | acc | cct | gtg | caa | cgc | acc | aac | tgg | gag | ttc | gcc | atc | aag | gtg | 2544 |
| Thr | Ala | Thr | Pro | Val | Gln | Arg | Thr | Asn | Trp | Glu | Phe | Ala | Ile | Lys | Val |  |
|  |  | 835 |  |  |  |  | 840 |  |  |  |  | 845 |  |  |  |  |
| ccc | aac | cgc | ggc | acc | atg | acg | gac | cgc | tac | tcc | ctg | aag | ggc | agc | cag | 2592 |
| Pro | Asn | Arg | Gly | Thr | Met | Thr | Asp | Arg | Tyr | Ser | Leu | Lys | Gly | Ser | Gln |  |
|  | 850 |  |  |  |  | 855 |  |  |  |  | 860 |  |  |  |  |  |
| ttc | cag | cag | ccc | ctc | ctg | gag | ttc | tcc | ggg | gcc | tgc | gag | ggc | tgc | ggc | 2640 |
| Phe | Gln | Gln | Pro | Leu | Leu | Glu | Phe | Ser | Gly | Ala | Cys | Glu | Gly | Cys | Gly |  |
| 865 |  |  |  |  | 870 |  |  |  |  | 875 |  |  |  |  | 880 |  |
| gag | acc | cca | tat | gtc | aag | ctg | ctc | acc | cag | ctc | ttc | ggc | gag | cgg | acg | 2688 |
| Glu | Thr | Pro | Tyr | Val | Lys | Leu | Leu | Thr | Gln | Leu | Phe | Gly | Glu | Arg | Thr |  |
|  |  |  |  | 885 |  |  |  |  | 890 |  |  |  |  | 895 |  |  |
| gtc | atc | gcc | aac | gcc | acc | ggc | tgc | agt | tcc | atc | tgg | ggt | ggc | act | gcc | 2736 |

```
Val Ile Ala Asn Ala Thr Gly Cys Ser Ser Ile Trp Gly Gly Thr Ala
            900                 905                 910 ggc ctg gcg ccg tac acc acc aac gcc aag ggc cag ggc ccg gcc tgg    2784
Gly Leu Ala Pro Tyr Thr Thr Asn Ala Lys Gly Gln Gly Pro Ala Trp
        915                 920                 925 ggc aac agc ctg ttc gag gac aac gcc gag ttc ggc ttt ggc att gca    2832
Gly Asn Ser Leu Phe Glu Asp Asn Ala Glu Phe Gly Phe Gly Ile Ala
    930                 935                 940 gtg gcc aac gcc cag aag agg tcc cgc gtg agg gac tgc atc ctg cag    2880
Val Ala Asn Ala Gln Lys Arg Ser Arg Val Arg Asp Cys Ile Leu Gln
945                 950                 955                 960 gca gtg gag aag aag gtc gcc gat gag ggt ttg acc aca ttg ttg gcg    2928
Ala Val Glu Lys Lys Val Ala Asp Glu Gly Leu Thr Thr Leu Leu Ala
                965                 970                 975 caa tgg ctg cag gat tgg aac aca gga gac aag acc ttg aag tac caa    2976
Gln Trp Leu Gln Asp Trp Asn Thr Gly Asp Lys Thr Leu Lys Tyr Gln
            980                 985                 990 gac cag atc att gca ggg ctg gca cag cag cgc agc aag gat ccc ctt    3024
Asp Gln Ile Ile Ala Gly Leu Ala Gln Gln Arg Ser Lys Asp Pro Leu
        995                 1000                1005 ctg gag cag atc tat ggc atg aag gac atg ctg cct aac atc agc cag    3072
Leu Glu Gln Ile Tyr Gly Met Lys Asp Met Leu Pro Asn Ile Ser Gln
    1010                1015                1020 tgg atc att ggt ggt gat ggc tgg gcc aac gac att ggt ttc ggt ggg    3120
Trp Ile Ile Gly Gly Asp Gly Trp Ala Asn Asp Ile Gly Phe Gly Gly
1025                1030                1035                1040 ctg gac cac gtg ctg gcc tct ggg cag aac ctc aac gtc ctg gtg ctg    3168
Leu Asp His Val Leu Ala Ser Gly Gln Asn Leu Asn Val Leu Val Leu
                1045                1050                1055 gac acc gag atg tac agc aac acc ggt ggg cag gcc tcc aag tcc acc    3216
Asp Thr Glu Met Tyr Ser Asn Thr Gly Gly Gln Ala Ser Lys Ser Thr
            1060                1065                1070 cac atg gcc tct gtg gcc aag ttt gcc ctg gga ggg aag cgc acc aac    3264
His Met Ala Ser Val Ala Lys Phe Ala Leu Gly Gly Lys Arg Thr Asn
        1075                1080                1085 aag aag aac ttg acg gag atg gca atg agc tat ggc aac gtc tat gtg    3312
Lys Lys Asn Leu Thr Glu Met Ala Met Ser Tyr Gly Asn Val Tyr Val
    1090                1095                1100 gcc acc gtc tcc cat ggc aac atg gcc cag tgc gtc aag gcg ttt gtg    3360
Ala Thr Val Ser His Gly Asn Met Ala Gln Cys Val Lys Ala Phe Val
1105                1110                1115                1120 gag gct gag tct tat gat gga cct tcg ctc att gtt ggc tat gcg cca    3408
Glu Ala Glu Ser Tyr Asp Gly Pro Ser Leu Ile Val Gly Tyr Ala Pro
                1125                1130                1135 tgc atc gag cat ggt ctg cgt gct ggt atg gca agg atg gtt caa gag    3456
Cys Ile Glu His Gly Leu Arg Ala Gly Met Ala Arg Met Val Gln Glu
            1140                1145                1150 tct gag gct gcc atc gcc acg gga tac tgg ccc ctg tac cgc ttt gac    3504
Ser Glu Ala Ala Ile Ala Thr Gly Tyr Trp Pro Leu Tyr Arg Phe Asp
        1155                1160                1165 ccc cgc ctg gcg acc gag ggc aag aac ccc ttc cag ctg gac tcc aag    3552
Pro Arg Leu Ala Thr Glu Gly Lys Asn Pro Phe Gln Leu Asp Ser Lys
    1170                1175                1180 cgc atc aag ggc aac ctg cag gag tac ctg gac cgc cag aac cgg tat    3600
Arg Ile Lys Gly Asn Leu Gln Glu Tyr Leu Asp Arg Gln Asn Arg Tyr
1185                1190                1195                1200 gtc aac ctg aag aag aac aac ccg aag ggt gcg gat ctg ctg aag tct    3648
Val Asn Leu Lys Lys Asn Asn Pro Lys Gly Ala Asp Leu Leu Lys Ser
                1205                1210                1215
```

| | |
|---|---|
| cag atg gcc gac aac atc acc gcc cgg ttc aac cgc tac cga cgc atg<br>Gln Met Ala Asp Asn Ile Thr Ala Arg Phe Asn Arg Tyr Arg Arg Met<br>                1220                      1225                      1230 | 3696 |
| ttg gag ggc ccc aat aca aaa gcc gcc gcc ccc agc ggc aac cat gtg<br>Leu Glu Gly Pro Asn Thr Lys Ala Ala Ala Pro Ser Gly Asn His Val<br>        1235                      1240                      1245 | 3744 |
| acc atc ctg tac ggc tcc gaa act ggc aac agt gag ggt ctg gca aag<br>Thr Ile Leu Tyr Gly Ser Glu Thr Gly Asn Ser Glu Gly Leu Ala Lys<br>1250                      1255                      1260 | 3792 |
| gag ctg gcc acc gac ttc gag cgc cgg gag tac tcc gtc gca gtg cag<br>Glu Leu Ala Thr Asp Phe Glu Arg Arg Glu Tyr Ser Val Ala Val Gln<br>1265                  1270                      1275                      1280 | 3840 |
| gct ttg gat gac atc gac gtt gct gac ttg gag aac atg ggc ttc gtg<br>Ala Leu Asp Asp Ile Asp Val Ala Asp Leu Glu Asn Met Gly Phe Val<br>                            1285                      1290                      1295 | 3888 |
| gtc att gcg gtg tcc acc tgt ggg cag gga cag ttc ccc cgc aac agc<br>Val Ile Ala Val Ser Thr Cys Gly Gln Gly Gln Phe Pro Arg Asn Ser<br>        1300                      1305                      1310 | 3936 |
| cag ctg ttc tgg cgg gag ctg cag cgg gac aag cct gag ggc tgg ctg<br>Gln Leu Phe Trp Arg Glu Leu Gln Arg Asp Lys Pro Glu Gly Trp Leu<br>                1315                      1320                      1325 | 3984 |
| aag aac ttg aag tac act gtc ttc ggg ctg ggc gac agc aca tac tac<br>Lys Asn Leu Lys Tyr Thr Val Phe Gly Leu Gly Asp Ser Thr Tyr Tyr<br>        1330                      1335                      1340 | 4032 |
| ttc tac tgc cac acc gcc aag cag atc gac gct cgc ctg gcc gcc ttg<br>Phe Tyr Cys His Thr Ala Lys Gln Ile Asp Ala Arg Leu Ala Ala Leu<br>1345                      1350                      1355                      1360 | 4080 |
| ggc gct cag cgg gtg gtg ccc att ggc ttc ggc gac gat ggg gat gag<br>Gly Ala Gln Arg Val Val Pro Ile Gly Phe Gly Asp Asp Gly Asp Glu<br>                1365                      1370                      1375 | 4128 |
| gac atg ttc cac acc ggc ttc aac aac tgg atc ccc agt gtg tgg aat<br>Asp Met Phe His Thr Gly Phe Asn Asn Trp Ile Pro Ser Val Trp Asn<br>        1380                      1385                      1390 | 4176 |
| gag ctc aag acc aag act ccg gag gaa gcg ctg ttc acc ccg agc atc<br>Glu Leu Lys Thr Lys Thr Pro Glu Glu Ala Leu Phe Thr Pro Ser Ile<br>                1395                      1400                      1405 | 4224 |
| gcc gtg cag ctc acc ccc aac gcc acc ccg cag gat ttc cat ttc gcc<br>Ala Val Gln Leu Thr Pro Asn Ala Thr Pro Gln Asp Phe His Phe Ala<br>1410                      1415                      1420 | 4272 |
| aag tcc acc cca gtg ctg tcc atc acc ggt gcc gaa cgc atc acg ccg<br>Lys Ser Thr Pro Val Leu Ser Ile Thr Gly Ala Glu Arg Ile Thr Pro<br>1425                      1430                      1435                      1440 | 4320 |
| gca gac cac acc cgc aac ttc gtc act atc cga tgg aag acc gat ttg<br>Ala Asp His Thr Arg Asn Phe Val Thr Ile Arg Trp Lys Thr Asp Leu<br>                            1445                      1450                      1455 | 4368 |
| tcg tac cag gtg ggt gac tct ctt ggt gtc ttc cct gag aac acc cgg<br>Ser Tyr Gln Val Gly Asp Ser Leu Gly Val Phe Pro Glu Asn Thr Arg<br>        1460                      1465                      1470 | 4416 |
| tca gtg gtg gag gag ttc ctg cag tat tac ggc ttg aac ccc aag gac<br>Ser Val Val Glu Glu Phe Leu Gln Tyr Tyr Gly Leu Asn Pro Lys Asp<br>                1475                      1480                      1485 | 4464 |
| gtc atc acc atc gaa aac aag ggc agc cgg gag ttg ccc cac tgc atg<br>Val Ile Thr Ile Glu Asn Lys Gly Ser Arg Glu Leu Pro His Cys Met<br>        1490                      1495                      1500 | 4512 |
| gct gtt ggg gat ctc ttc acg aag gtg ttg gac atc ttg ggc aaa ccc<br>Ala Val Gly Asp Leu Phe Thr Lys Val Leu Asp Ile Leu Gly Lys Pro<br>1505                      1510                      1515                      1520 | 4560 |
| aac aac cgg ttc tac aag acc ctt tct tac ttt gca gtg gac aag gcc<br>Asn Asn Arg Phe Tyr Lys Thr Leu Ser Tyr Phe Ala Val Asp Lys Ala<br>                1525                      1530                      1535 | 4608 |

```
gag aag gag cgc ttg ttg aag atc gcc gag atg ggg ccg gag tac agc      4656
Glu Lys Glu Arg Leu Leu Lys Ile Ala Glu Met Gly Pro Glu Tyr Ser
            1540                1545                1550 aac atc ctg tct gag acg tac cac tac gcg gac atc ttc cac atg ttc      4704
Asn Ile Leu Ser Glu Thr Tyr His Tyr Ala Asp Ile Phe His Met Phe
        1555                1560                1565 ccg tcc gcc cgg ccc acg ctg cag tac ctc atc gag atg atc ccc aac      4752
Pro Ser Ala Arg Pro Thr Leu Gln Tyr Leu Ile Glu Met Ile Pro Asn
    1570                1575                1580 atc aag ccc cgg tac tac tcc atc tcc tcc gcc ccc atc cac acc cct      4800
Ile Lys Pro Arg Tyr Tyr Ser Ile Ser Ser Ala Pro Ile His Thr Pro
1585                1590                1595                1600 ggc gag gtc cac agc ctg gtg ctc atc gac acc tgg atc acg ctg tcc      4848
Gly Glu Val His Ser Leu Val Leu Ile Asp Thr Trp Ile Thr Leu Ser
                1605                1610                1615 ggc aag cac cgc acg ggg ctg acc tgc acc atg ctg gag cac ctg cag      4896
Gly Lys His Arg Thr Gly Leu Thr Cys Thr Met Leu Glu His Leu Gln
            1620                1625                1630 gcg ggc cag gtg gtg gat ggc tgc atc cac ccc acg gcg atg gag ttc      4944
Ala Gly Gln Val Val Asp Gly Cys Ile His Pro Thr Ala Met Glu Phe
        1635                1640                1645 ccc gac cac gag aag ccg gtg gtg atg tgc gcc atg ggc agt ggc ctg      4992
Pro Asp His Glu Lys Pro Val Val Met Cys Ala Met Gly Ser Gly Leu
    1650                1655                1660 gca ccg ttc gtt gct ttc ctg cgc gac ggc tcc acg ctg cgg aag cag      5040
Ala Pro Phe Val Ala Phe Leu Arg Asp Gly Ser Thr Leu Arg Lys Gln
1665                1670                1675                1680 ggc aag aag acc ggg aac atg gca ttg tac ttc ggc aac agg tat gag      5088
Gly Lys Lys Thr Gly Asn Met Ala Leu Tyr Phe Gly Asn Arg Tyr Glu
                1685                1690                1695 aag acg gag ttc ctg atg aag gag gag ctg aag ggt cac atc aac gat      5136
Lys Thr Glu Phe Leu Met Lys Glu Glu Leu Lys Gly His Ile Asn Asp
            1700                1705                1710 ggt ttg ctg aca ctt cga tgc gct ttc agc cga gat gac ccc aag aag      5184
Gly Leu Leu Thr Leu Arg Cys Ala Phe Ser Arg Asp Asp Pro Lys Lys
        1715                1720                1725 aag gtg tat gtg cag gac ctt atc aag atg gac gaa aag atg atg tac      5232
Lys Val Tyr Val Gln Asp Leu Ile Lys Met Asp Glu Lys Met Met Tyr
    1730                1735                1740 gat tac ctc gtg gtg cag aag ggt tct atg tat tgc tgt gga tcc cgc      5280
Asp Tyr Leu Val Val Gln Lys Gly Ser Met Tyr Cys Cys Gly Ser Arg
1745                1750                1755                1760 agt ttc atc aag cct gtc cag gag tca ttg aaa cat tgc ttc atg aaa      5328
Ser Phe Ile Lys Pro Val Gln Glu Ser Leu Lys His Cys Phe Met Lys
                1765                1770                1775 gct ggt ggg ctg act gca gag caa gct gag aac gag gtc atc gat atg      5376
Ala Gly Gly Leu Thr Ala Glu Gln Ala Glu Asn Glu Val Ile Asp Met
            1780                1785                1790 ttc acg acc ggg cgg tac aat atc gag gca tgg taa                      5412
Phe Thr Thr Gly Arg Tyr Asn Ile Glu Ala Trp
        1795                1800

<210> SEQ ID NO 6
<211> LENGTH: 1803
<212> TYPE: PRT
<213> ORGANISM: Euglena gracilis

<400> SEQUENCE: 6

Met Lys Gln Ser Val Arg Pro Ile Ile Ser Asn Val Leu Arg Lys Glu
1               5                   10                  15
```

-continued

```
Val Ala Leu Tyr Ser Thr Ile Ile Gly Gln Asp Lys Gly Lys Glu Pro
             20                  25                  30

Thr Gly Arg Thr Tyr Thr Ser Gly Pro Lys Pro Ala Ser His Ile Glu
         35                  40                  45

Val Pro His His Val Thr Val Pro Ala Thr Asp Arg Thr Pro Asn Pro
     50                  55                  60

Asp Ala Gln Phe Phe Gln Ser Val Asp Gly Ser Gln Ala Thr Ser His
 65                  70                  75                  80

Val Ala Tyr Ala Leu Ser Asp Thr Ala Phe Ile Tyr Pro Ile Thr Pro
                 85                  90                  95

Ser Ser Val Met Gly Glu Leu Ala Asp Val Trp Met Ala Gln Gly Arg
            100                 105                 110

Lys Asn Ala Phe Gly Gln Val Asp Val Arg Glu Met Gln Ser Glu
        115                 120                 125

Ala Gly Ala Ala Gly Ala Leu His Gly Ala Leu Ala Ala Gly Ala Ile
    130                 135                 140

Ala Thr Thr Phe Thr Ala Ser Gln Gly Leu Leu Leu Met Ile Pro Asn
145                 150                 155                 160

Met Tyr Lys Ile Ala Gly Glu Leu Met Pro Ser Val Ile His Val Ala
                165                 170                 175

Ala Arg Glu Leu Ala Gly His Ala Leu Ser Ile Phe Gly Gly His Ala
            180                 185                 190

Asp Val Met Ala Val Arg Gln Thr Gly Trp Ala Met Leu Cys Ser His
        195                 200                 205

Thr Val Gln Gln Ser His Asp Met Ala Leu Ile Ser His Val Ala Thr
    210                 215                 220

Leu Lys Ser Ser Ile Pro Phe Val His Phe Phe Asp Gly Phe Arg Thr
225                 230                 235                 240

Ser His Glu Val Asn Lys Ile Lys Met Leu Pro Tyr Ala Glu Leu Lys
                245                 250                 255

Lys Leu Val Pro Pro Gly Thr Met Glu Gln His Trp Ala Arg Ser Leu
            260                 265                 270

Asn Pro Met His Pro Thr Ile Arg Gly Thr Asn Gln Ser Ala Asp Ile
        275                 280                 285

Tyr Phe Gln Asn Met Glu Ser Ala Asn Gln Tyr Tyr Thr Asp Leu Ala
    290                 295                 300

Glu Val Val Gln Glu Thr Met Asp Glu Val Ala Pro Tyr Ile Gly Arg
305                 310                 315                 320

His Tyr Lys Ile Phe Glu Tyr Val Gly Ala Pro Asp Ala Glu Glu Val
                325                 330                 335

Thr Val Leu Met Gly Ser Gly Ala Thr Thr Val Asn Glu Ala Val Asp
            340                 345                 350

Leu Leu Val Lys Arg Gly Lys Lys Val Gly Ala Val Leu Val His Leu
        355                 360                 365

Tyr Arg Pro Trp Ser Thr Lys Ala Phe Glu Lys Val Leu Pro Lys Thr
    370                 375                 380

Val Lys Arg Ile Ala Ala Leu Asp Arg Cys Lys Glu Val Thr Ala Leu
385                 390                 395                 400

Gly Glu Pro Leu Tyr Leu Asp Val Ser Ala Thr Leu Asn Leu Phe Pro
                405                 410                 415

Glu Arg Gln Asn Val Lys Val Ile Gly Gly Arg Tyr Gly Leu Gly Ser
            420                 425                 430
```

-continued

```
Lys Asp Phe Ile Pro Glu His Ala Leu Ala Ile Tyr Ala Asn Leu Ala
        435                 440                 445

Ser Glu Asn Pro Ile Gln Arg Phe Thr Val Gly Ile Thr Asp Asp Val
    450                 455                 460

Thr Gly Thr Ser Val Pro Phe Val Asn Glu Arg Val Asp Thr Leu Pro
465                 470                 475                 480

Glu Gly Thr Arg Gln Cys Val Phe Trp Gly Ile Gly Ser Asp Gly Thr
            485                 490                 495

Val Gly Ala Asn Arg Ser Ala Val Arg Ile Ile Gly Asp Asn Ser Asp
            500                 505                 510

Leu Met Val Gln Ala Tyr Phe Gln Phe Asp Ala Phe Lys Ser Gly Gly
        515                 520                 525

Val Thr Ser Ser His Leu Arg Phe Gly Pro Lys Pro Ile Thr Ala Gln
    530                 535                 540

Tyr Leu Val Thr Asn Ala Asp Tyr Ile Ala Cys His Phe Gln Glu Tyr
545                 550                 555                 560

Val Lys Arg Phe Asp Met Leu Asp Ala Ile Arg Glu Gly Gly Thr Phe
            565                 570                 575

Val Leu Asn Ser Arg Trp Thr Thr Glu Asp Met Glu Lys Glu Ile Pro
            580                 585                 590

Ala Asp Phe Arg Arg Lys Leu Ala Gln Lys Lys Val Arg Phe Tyr Asn
        595                 600                 605

Val Asp Ala Arg Lys Ile Cys Asp Ser Phe Gly Leu Gly Lys Arg Ile
    610                 615                 620

Asn Met Leu Met Gln Ala Cys Phe Phe Lys Leu Ser Gly Val Leu Pro
625                 630                 635                 640

Leu Ala Glu Ala Gln Arg Leu Leu Asn Glu Ser Ile Val His Glu Tyr
            645                 650                 655

Gly Lys Lys Gly Gly Lys Val Val Glu Met Asn Gln Ala Val Val Asn
            660                 665                 670

Ala Val Phe Ala Gly Asp Leu Pro Gln Glu Val Gln Val Pro Ala Ala
        675                 680                 685

Trp Ala Asn Ala Val Asp Thr Ser Thr Arg Thr Pro Thr Gly Ile Glu
    690                 695                 700

Phe Val Asp Lys Ile Met Arg Pro Leu Met Asp Phe Lys Gly Asp Gln
705                 710                 715                 720

Leu Pro Val Ser Val Met Thr Pro Gly Gly Thr Phe Pro Val Gly Thr
            725                 730                 735

Thr Gln Tyr Ala Lys Arg Ala Ile Ala Ala Phe Ile Pro Gln Trp Ile
            740                 745                 750

Pro Ala Asn Cys Thr Gln Cys Asn Tyr Cys Ser Tyr Val Cys Pro His
        755                 760                 765

Ala Thr Ile Arg Pro Phe Val Leu Thr Asp Gln Glu Val Gln Leu Ala
    770                 775                 780

Pro Glu Ser Phe Val Thr Arg Lys Ala Lys Gly Asp Tyr Gln Gly Met
785                 790                 795                 800

Asn Phe Arg Ile Gln Val Ala Pro Glu Asp Cys Thr Gly Cys Gln Val
            805                 810                 815

Cys Val Glu Thr Cys Pro Asp Asp Ala Leu Glu Met Thr Asp Ala Phe
            820                 825                 830

Thr Ala Thr Pro Val Gln Arg Thr Asn Trp Glu Phe Ala Ile Lys Val
        835                 840                 845

Pro Asn Arg Gly Thr Met Thr Asp Arg Tyr Ser Leu Lys Gly Ser Gln
```

-continued

```
            850                 855                 860
Phe Gln Gln Pro Leu Leu Glu Phe Ser Gly Ala Cys Glu Gly Cys Gly
865                 870                 875                 880

Glu Thr Pro Tyr Val Lys Leu Leu Thr Gln Leu Phe Gly Glu Arg Thr
                885                 890                 895

Val Ile Ala Asn Ala Thr Gly Cys Ser Ser Ile Trp Gly Gly Thr Ala
                900                 905                 910

Gly Leu Ala Pro Tyr Thr Thr Asn Ala Lys Gly Gln Gly Pro Ala Trp
            915                 920                 925

Gly Asn Ser Leu Phe Glu Asp Asn Ala Glu Phe Gly Phe Gly Ile Ala
            930                 935                 940

Val Ala Asn Ala Gln Lys Arg Ser Arg Val Arg Asp Cys Ile Leu Gln
945                 950                 955                 960

Ala Val Glu Lys Lys Val Ala Asp Glu Gly Leu Thr Thr Leu Leu Ala
                965                 970                 975

Gln Trp Leu Gln Asp Trp Asn Thr Gly Asp Lys Thr Leu Lys Tyr Gln
                980                 985                 990

Asp Gln Ile Ile Ala Gly Leu Ala Gln Arg Ser Lys Asp Pro Leu
            995                 1000                1005

Leu Glu Gln Ile Tyr Gly Met Lys Asp Met Leu Pro Asn Ile Ser Gln
            1010                1015                1020

Trp Ile Ile Gly Gly Asp Gly Trp Ala Asn Asp Ile Gly Phe Gly Gly
1025                1030                1035                1040

Leu Asp His Val Leu Ala Ser Gly Gln Asn Leu Asn Val Leu Val Leu
                1045                1050                1055

Asp Thr Glu Met Tyr Ser Asn Thr Gly Gly Gln Ala Ser Lys Ser Thr
                1060                1065                1070

His Met Ala Ser Val Ala Lys Phe Ala Leu Gly Gly Lys Arg Thr Asn
            1075                1080                1085

Lys Lys Asn Leu Thr Glu Met Ala Met Ser Tyr Gly Asn Val Tyr Val
            1090                1095                1100

Ala Thr Val Ser His Gly Asn Met Ala Gln Cys Val Lys Ala Phe Val
1105                1110                1115                1120

Glu Ala Glu Ser Tyr Asp Gly Pro Ser Leu Ile Val Gly Tyr Ala Pro
                1125                1130                1135

Cys Ile Glu His Gly Leu Arg Ala Gly Met Ala Arg Met Val Gln Glu
                1140                1145                1150

Ser Glu Ala Ala Ile Ala Thr Gly Tyr Trp Pro Leu Tyr Arg Phe Asp
            1155                1160                1165

Pro Arg Leu Ala Thr Glu Gly Lys Asn Pro Phe Gln Leu Asp Ser Lys
            1170                1175                1180

Arg Ile Lys Gly Asn Leu Gln Glu Tyr Leu Asp Arg Gln Asn Arg Tyr
1185                1190                1195                1200

Val Asn Leu Lys Lys Asn Asn Pro Lys Gly Ala Asp Leu Leu Lys Ser
                1205                1210                1215

Gln Met Ala Asp Asn Ile Thr Ala Arg Phe Asn Arg Tyr Arg Arg Met
                1220                1225                1230

Leu Glu Gly Pro Asn Thr Lys Ala Ala Ala Pro Ser Gly Asn His Val
            1235                1240                1245

Thr Ile Leu Tyr Gly Ser Glu Thr Gly Asn Ser Glu Gly Leu Ala Lys
            1250                1255                1260

Glu Leu Ala Thr Asp Phe Glu Arg Arg Glu Tyr Ser Val Ala Val Gln
1265                1270                1275                1280
```

-continued

Ala Leu Asp Asp Ile Asp Val Ala Asp Leu Glu Asn Met Gly Phe Val
            1285                1290                1295

Val Ile Ala Val Ser Thr Cys Gly Gln Gly Gln Phe Pro Arg Asn Ser
        1300                1305                1310

Gln Leu Phe Trp Arg Glu Leu Gln Arg Asp Lys Pro Glu Gly Trp Leu
        1315                1320                1325

Lys Asn Leu Lys Tyr Thr Val Phe Gly Leu Gly Asp Ser Thr Tyr Tyr
        1330                1335                1340

Phe Tyr Cys His Thr Ala Lys Gln Ile Asp Ala Arg Leu Ala Ala Leu
1345                1350                1355                1360

Gly Ala Gln Arg Val Val Pro Ile Gly Phe Gly Asp Asp Gly Asp Glu
            1365                1370                1375

Asp Met Phe His Thr Gly Phe Asn Asn Trp Ile Pro Ser Val Trp Asn
            1380                1385                1390

Glu Leu Lys Thr Lys Thr Pro Glu Glu Ala Leu Phe Thr Pro Ser Ile
            1395                1400                1405

Ala Val Gln Leu Thr Pro Asn Ala Thr Pro Gln Asp Phe His Phe Ala
            1410                1415                1420

Lys Ser Thr Pro Val Leu Ser Ile Thr Gly Ala Glu Arg Ile Thr Pro
1425                1430                1435                1440

Ala Asp His Thr Arg Asn Phe Val Thr Ile Arg Trp Lys Thr Asp Leu
            1445                1450                1455

Ser Tyr Gln Val Gly Asp Ser Leu Gly Val Phe Pro Glu Asn Thr Arg
            1460                1465                1470

Ser Val Val Glu Glu Phe Leu Gln Tyr Tyr Gly Leu Asn Pro Lys Asp
            1475                1480                1485

Val Ile Thr Ile Glu Asn Lys Gly Ser Arg Glu Leu Pro His Cys Met
            1490                1495                1500

Ala Val Gly Asp Leu Phe Thr Lys Val Leu Asp Ile Leu Gly Lys Pro
1505                1510                1515                1520

Asn Asn Arg Phe Tyr Lys Thr Leu Ser Tyr Phe Ala Val Asp Lys Ala
            1525                1530                1535

Glu Lys Glu Arg Leu Leu Lys Ile Ala Glu Met Gly Pro Glu Tyr Ser
            1540                1545                1550

Asn Ile Leu Ser Glu Thr Tyr His Tyr Ala Asp Ile Phe His Met Phe
            1555                1560                1565

Pro Ser Ala Arg Pro Thr Leu Gln Tyr Leu Ile Glu Met Ile Pro Asn
1570                1575                1580

Ile Lys Pro Arg Tyr Tyr Ser Ile Ser Ser Ala Pro Ile His Thr Pro
1585                1590                1595                1600

Gly Glu Val His Ser Leu Val Leu Ile Asp Thr Trp Ile Thr Leu Ser
            1605                1610                1615

Gly Lys His Arg Thr Gly Leu Cys Thr Met Leu Glu His Leu Gln
            1620                1625                1630

Ala Gly Gln Val Val Asp Gly Cys Ile His Pro Thr Ala Met Glu Phe
            1635                1640                1645

Pro Asp His Glu Lys Pro Val Val Met Cys Ala Met Gly Ser Gly Leu
            1650                1655                1660

Ala Pro Phe Val Ala Phe Leu Arg Asp Gly Ser Thr Leu Arg Lys Gln
1665                1670                1675                1680

Gly Lys Lys Thr Gly Asn Met Ala Leu Tyr Phe Gly Asn Arg Tyr Glu
            1685                1690                1695

-continued

```
Lys Thr Glu Phe Leu Met Lys Glu Glu Leu Lys Gly His Ile Asn Asp
            1700                1705                1710

Gly Leu Leu Thr Leu Arg Cys Ala Phe Ser Arg Asp Pro Lys Lys
        1715                1720                1725

Lys Val Tyr Val Gln Asp Leu Ile Lys Met Asp Glu Lys Met Met Tyr
    1730                1735                1740

Asp Tyr Leu Val Val Gln Lys Gly Ser Met Tyr Cys Cys Gly Ser Arg
1745                1750                1755                1760

Ser Phe Ile Lys Pro Val Gln Glu Ser Leu Lys His Cys Phe Met Lys
                1765                1770                1775

Ala Gly Gly Leu Thr Ala Glu Gln Ala Glu Asn Glu Val Ile Asp Met
            1780                1785                1790

Phe Thr Thr Gly Arg Tyr Asn Ile Glu Ala Trp
        1795                1800

<210> SEQ ID NO 7
<211> LENGTH: 747
<212> TYPE: DNA
<213> ORGANISM: Escherichia coli
<220> FEATURE:
<221> NAME/KEY: CDS
<222> LOCATION: (1)..(747)

<400> SEQUENCE: 7 atg gct gat tgg gta aca ggc aaa gtc act aaa gtg cag aac tgg acc      48
Met Ala Asp Trp Val Thr Gly Lys Val Thr Lys Val Gln Asn Trp Thr
1               5                   10                  15 gac gcc ctg ttt agt ctc acc gtt cac gcc ccc gtg ctt ccg ttt acc      96
Asp Ala Leu Phe Ser Leu Thr Val His Ala Pro Val Leu Pro Phe Thr
                20                  25                  30 gcc ggg caa ttt acc aag ctt ggc ctt gaa atc gac ggc gaa cgc gtc     144
Ala Gly Gln Phe Thr Lys Leu Gly Leu Glu Ile Asp Gly Glu Arg Val
            35                  40                  45 cag cgc gcc tac tcc tat gta aac tcg ccc gat aat ccc gat ctg gag     192
Gln Arg Ala Tyr Ser Tyr Val Asn Ser Pro Asp Asn Pro Asp Leu Glu
        50                  55                  60 ttt tac ctg gtc acc gtc ccc gat ggc aaa tta agc cca cga ctg gcg     240
Phe Tyr Leu Val Thr Val Pro Asp Gly Lys Leu Ser Pro Arg Leu Ala
65                  70                  75                  80 gca ctg aaa cca ggc gat gaa gtg cag gtg gtt agc gaa gcg gca gga     288
Ala Leu Lys Pro Gly Asp Glu Val Gln Val Val Ser Glu Ala Ala Gly
                85                  90                  95 ttc ttt gtg ctc gat gaa gtg ccg cac tgc gaa acg cta tgg atg ctg     336
Phe Phe Val Leu Asp Glu Val Pro His Cys Glu Thr Leu Trp Met Leu
                100                 105                 110 gca acc ggt aca gcg att ggc cct tat tta tcg att ctg caa cta ggt     384
Ala Thr Gly Thr Ala Ile Gly Pro Tyr Leu Ser Ile Leu Gln Leu Gly
            115                 120                 125 aaa gat tta gat cgc ttc aaa aat ctg gtc ctg gtg cac gcc gca cgt     432
Lys Asp Leu Asp Arg Phe Lys Asn Leu Val Leu Val His Ala Ala Arg
        130                 135                 140 tat gcc gcc gac tta agc tat ttg cca ctg atg cag gaa ctg gaa aaa     480
Tyr Ala Ala Asp Leu Ser Tyr Leu Pro Leu Met Gln Glu Leu Glu Lys
145                 150                 155                 160 cgc tac gaa gga aaa ctg cgc att cag acg gtg gtc agt cgg gaa acg     528
Arg Tyr Glu Gly Lys Leu Arg Ile Gln Thr Val Val Ser Arg Glu Thr
                165                 170                 175 gca gcg ggg tcg ctc acc gga cgg ata ccg gca tta att gaa agt ggg     576
Ala Ala Gly Ser Leu Thr Gly Arg Ile Pro Ala Leu Ile Glu Ser Gly
            180                 185                 190
```

```
gaa ctg gaa agc acg att ggc ctg ccg atg aat aaa gaa acc agc cat      624
Glu Leu Glu Ser Thr Ile Gly Leu Pro Met Asn Lys Glu Thr Ser His
            195                 200                 205 gtg atg ctg tgc ggc aat cca cag atg gtg cgc gat aca caa cag ttg      672
Val Met Leu Cys Gly Asn Pro Gln Met Val Arg Asp Thr Gln Gln Leu
    210                 215                 220 ctg aaa gag acc cgg cag atg acg aaa cat tta cgt cgc cga ccg ggc      720
Leu Lys Glu Thr Arg Gln Met Thr Lys His Leu Arg Arg Arg Pro Gly
225                 230                 235                 240 cat atg aca gcg gag cat tac tgg taa                                  747
His Met Thr Ala Glu His Tyr Trp
                245

<210> SEQ ID NO 8
<211> LENGTH: 248
<212> TYPE: PRT
<213> ORGANISM: Escherichia coli

<400> SEQUENCE: 8

Met Ala Asp Trp Val Thr Gly Lys Val Thr Lys Val Gln Asn Trp Thr
1               5                   10                  15

Asp Ala Leu Phe Ser Leu Thr Val His Ala Pro Val Leu Pro Phe Thr
            20                  25                  30

Ala Gly Gln Phe Thr Lys Leu Gly Leu Glu Ile Asp Gly Glu Arg Val
        35                  40                  45

Gln Arg Ala Tyr Ser Tyr Val Asn Ser Pro Asp Asn Pro Asp Leu Glu
    50                  55                  60

Phe Tyr Leu Val Thr Val Pro Asp Gly Lys Leu Ser Pro Arg Leu Ala
65                  70                  75                  80

Ala Leu Lys Pro Gly Asp Glu Val Gln Val Ser Glu Ala Ala Gly
                85                  90                  95

Phe Phe Val Leu Asp Glu Val Pro His Cys Glu Thr Leu Trp Met Leu
            100                 105                 110

Ala Thr Gly Thr Ala Ile Gly Pro Tyr Leu Ser Ile Leu Gln Leu Gly
        115                 120                 125

Lys Asp Leu Asp Arg Phe Lys Asn Leu Val Leu Val His Ala Ala Arg
130                 135                 140

Tyr Ala Ala Asp Leu Ser Tyr Leu Pro Leu Met Gln Glu Leu Glu Lys
145                 150                 155                 160

Arg Tyr Glu Gly Lys Leu Arg Ile Gln Thr Val Val Ser Arg Glu Thr
                165                 170                 175

Ala Ala Gly Ser Leu Thr Gly Arg Ile Pro Ala Leu Ile Glu Ser Gly
            180                 185                 190

Glu Leu Glu Ser Thr Ile Gly Leu Pro Met Asn Lys Glu Thr Ser His
        195                 200                 205

Val Met Leu Cys Gly Asn Pro Gln Met Val Arg Asp Thr Gln Gln Leu
    210                 215                 220

Leu Lys Glu Thr Arg Gln Met Thr Lys His Leu Arg Arg Arg Pro Gly
225                 230                 235                 240

His Met Thr Ala Glu His Tyr Trp
                245

<210> SEQ ID NO 9
<211> LENGTH: 336
<212> TYPE: DNA
<213> ORGANISM: Escherichia coli
<220> FEATURE:
```

-continued

```
<221> NAME/KEY: CDS
<222> LOCATION: (1)..(336)

<400> SEQUENCE: 9 atg cca aag att gtt att ttg cct cat cag gat ctc tgc cct gat ggc        48
Met Pro Lys Ile Val Ile Leu Pro His Gln Asp Leu Cys Pro Asp Gly
1               5                   10                  15 gct gtt ctg gaa gct aat agc ggt gaa acc att ctc gac gca gct ctg        96
Ala Val Leu Glu Ala Asn Ser Gly Glu Thr Ile Leu Asp Ala Ala Leu
            20                  25                  30 cgt aac ggt atc gag att gaa cac gcc tgt gaa aaa tcc tgt gct tgc       144
Arg Asn Gly Ile Glu Ile Glu His Ala Cys Glu Lys Ser Cys Ala Cys
        35                  40                  45 acc acc tgc cac tgc atc gtt cgt gaa ggt ttt gac tca ctg ccg gaa       192
Thr Thr Cys His Cys Ile Val Arg Glu Gly Phe Asp Ser Leu Pro Glu
    50                  55                  60 agc tca gag cag gaa gac gac atg ctg gac aaa gcc tgg gga ctg gag       240
Ser Ser Glu Gln Glu Asp Asp Met Leu Asp Lys Ala Trp Gly Leu Glu
65                  70                  75                  80 ccg gaa agc cgt tta agc tgc cag gcg cgc gtt acc gac gaa gat tta       288
Pro Glu Ser Arg Leu Ser Cys Gln Ala Arg Val Thr Asp Glu Asp Leu
                85                  90                  95 gta gtc gaa atc ccg cgt tac act atc aac cat gcg cgt gag cat taa       336
Val Val Glu Ile Pro Arg Tyr Thr Ile Asn His Ala Arg Glu His
            100                 105                 110

<210> SEQ ID NO 10
<211> LENGTH: 111
<212> TYPE: PRT
<213> ORGANISM: Escherichia coli

<400> SEQUENCE: 10

Met Pro Lys Ile Val Ile Leu Pro His Gln Asp Leu Cys Pro Asp Gly
1               5                   10                  15

Ala Val Leu Glu Ala Asn Ser Gly Glu Thr Ile Leu Asp Ala Ala Leu
            20                  25                  30

Arg Asn Gly Ile Glu Ile Glu His Ala Cys Glu Lys Ser Cys Ala Cys
        35                  40                  45

Thr Thr Cys His Cys Ile Val Arg Glu Gly Phe Asp Ser Leu Pro Glu
    50                  55                  60

Ser Ser Glu Gln Glu Asp Asp Met Leu Asp Lys Ala Trp Gly Leu Glu
65                  70                  75                  80

Pro Glu Ser Arg Leu Ser Cys Gln Ala Arg Val Thr Asp Glu Asp Leu
                85                  90                  95

Val Val Glu Ile Pro Arg Tyr Thr Ile Asn His Ala Arg Glu His
            100                 105                 110

<210> SEQ ID NO 11
<211> LENGTH: 261
<212> TYPE: DNA
<213> ORGANISM: Escherichia coli
<220> FEATURE:
<221> NAME/KEY: CDS
<222> LOCATION: (1)..(261)

<400> SEQUENCE: 11 atg gcg ttg tta atc act aaa aaa tgc atc aat tgt gat atg tgt gaa        48
Met Ala Leu Leu Ile Thr Lys Lys Cys Ile Asn Cys Asp Met Cys Glu
1               5                   10                  15 ccc gaa tgc ccg aat gag gcg att tca atg gga gat cat atc tac gag        96
Pro Glu Cys Pro Asn Glu Ala Ile Ser Met Gly Asp His Ile Tyr Glu
```

```
                 20                  25                  30
att aac agc gat aag tgt acc gaa tgc gta ggg cac tac gag aca cca    144
Ile Asn Ser Asp Lys Cys Thr Glu Cys Val Gly His Tyr Glu Thr Pro
             35                  40                  45 acc tgc cag aag gtg tgc ccg atc ccc aat act att gtg aaa gat ccg    192
Thr Cys Gln Lys Val Cys Pro Ile Pro Asn Thr Ile Val Lys Asp Pro
 50                  55                  60 gcg cat gtc gag aca gaa gaa cag ttg tgg gat aaa ttt gtg ctg atg    240
Ala His Val Glu Thr Glu Glu Gln Leu Trp Asp Lys Phe Val Leu Met
 65                  70                  75                  80 cac cac gcg gat aaa att taa                                        261
His His Ala Asp Lys Ile
                85

<210> SEQ ID NO 12
<211> LENGTH: 86
<212> TYPE: PRT
<213> ORGANISM: Escherichia coli

<400> SEQUENCE: 12

Met Ala Leu Leu Ile Thr Lys Lys Cys Ile Asn Cys Asp Met Cys Glu
 1               5                  10                  15

Pro Glu Cys Pro Asn Glu Ala Ile Ser Met Gly Asp His Ile Tyr Glu
                 20                  25                  30

Ile Asn Ser Asp Lys Cys Thr Glu Cys Val Gly His Tyr Glu Thr Pro
             35                  40                  45

Thr Cys Gln Lys Val Cys Pro Ile Pro Asn Thr Ile Val Lys Asp Pro
 50                  55                  60

Ala His Val Glu Thr Glu Glu Gln Leu Trp Asp Lys Phe Val Leu Met
 65                  70                  75                  80

His His Ala Asp Lys Ile
                85

<210> SEQ ID NO 13
<211> LENGTH: 531
<212> TYPE: DNA
<213> ORGANISM: Escherichia coli
<220> FEATURE:
<221> NAME/KEY: CDS
<222> LOCATION: (1)..(531)

<400> SEQUENCE: 13 atg gct atc act ggc atc ttt ttc ggc agc gac acc ggt aat acc gaa     48
Met Ala Ile Thr Gly Ile Phe Phe Gly Ser Asp Thr Gly Asn Thr Glu
 1               5                  10                  15 aat atc gca aaa atg att caa aaa cag ctt ggt aaa gac gtt gcc gat     96
Asn Ile Ala Lys Met Ile Gln Lys Gln Leu Gly Lys Asp Val Ala Asp
                 20                  25                  30 gtc cat gac att gca aaa agc agc aaa gaa gat ctg gaa gct tat gac    144
Val His Asp Ile Ala Lys Ser Ser Lys Glu Asp Leu Glu Ala Tyr Asp
             35                  40                  45 att ctg ctg ctg ggc atc cca acc tgg tat tac ggc gaa gcg cag tgt    192
Ile Leu Leu Leu Gly Ile Pro Thr Trp Tyr Tyr Gly Glu Ala Gln Cys
 50                  55                  60 gac tgg gat gac ttc ttc ccg act ctc gaa gag att gat ttc aac ggc    240
Asp Trp Asp Asp Phe Phe Pro Thr Leu Glu Glu Ile Asp Phe Asn Gly
 65                  70                  75                  80 aaa ctg gtt gcg ctg ttt ggt tgt ggt gac cag gaa gat tac gcc gaa    288
Lys Leu Val Ala Leu Phe Gly Cys Gly Asp Gln Glu Asp Tyr Ala Glu
                 85                  90                  95
```

```
tat ttc tgc gac gca ttg ggc acc atc cgc gac atc att gaa ccg cgc      336
Tyr Phe Cys Asp Ala Leu Gly Thr Ile Arg Asp Ile Ile Glu Pro Arg
            100                 105                 110 ggt gca acc atc gtt ggt cac tgg cca act gcg ggc tat cat ttc gaa      384
Gly Ala Thr Ile Val Gly His Trp Pro Thr Ala Gly Tyr His Phe Glu
        115                 120                 125 gca tca aaa ggt ctg gca gat gac gac cac ttt gtc ggt ctg gct atc      432
Ala Ser Lys Gly Leu Ala Asp Asp Asp His Phe Val Gly Leu Ala Ile
    130                 135                 140 gac gaa gac cgt cag ccg gaa ctg acc gct gaa cgt gta gaa aaa tgg      480
Asp Glu Asp Arg Gln Pro Glu Leu Thr Ala Glu Arg Val Glu Lys Trp
145                 150                 155                 160 gtt aaa cag att tct gaa gag ttg cat ctc gac gaa att ctc aat gcc      528
Val Lys Gln Ile Ser Glu Glu Leu His Leu Asp Glu Ile Leu Asn Ala
                165                 170                 175 tga                                                                   531
```

<210> SEQ ID NO 14
<211> LENGTH: 176
<212> TYPE: PRT
<213> ORGANISM: Escherichia coli

<400> SEQUENCE: 14

Met Ala Ile Thr Gly Ile Phe Phe Gly Ser Asp Thr Gly Asn Thr Glu
1               5                   10                  15

Asn Ile Ala Lys Met Ile Gln Lys Gln Leu Gly Lys Asp Val Ala Asp
            20                  25                  30

Val His Asp Ile Ala Lys Ser Ser Lys Glu Asp Leu Glu Ala Tyr Asp
        35                  40                  45

Ile Leu Leu Leu Gly Ile Pro Thr Trp Tyr Tyr Gly Glu Ala Gln Cys
    50                  55                  60

Asp Trp Asp Asp Phe Phe Pro Thr Leu Glu Glu Ile Asp Phe Asn Gly
65                  70                  75                  80

Lys Leu Val Ala Leu Phe Gly Cys Gly Asp Gln Glu Asp Tyr Ala Glu
                85                  90                  95

Tyr Phe Cys Asp Ala Leu Gly Thr Ile Arg Asp Ile Ile Glu Pro Arg
            100                 105                 110

Gly Ala Thr Ile Val Gly His Trp Pro Thr Ala Gly Tyr His Phe Glu
        115                 120                 125

Ala Ser Lys Gly Leu Ala Asp Asp Asp His Phe Val Gly Leu Ala Ile
    130                 135                 140

Asp Glu Asp Arg Gln Pro Glu Leu Thr Ala Glu Arg Val Glu Lys Trp
145                 150                 155                 160

Val Lys Gln Ile Ser Glu Glu Leu His Leu Asp Glu Ile Leu Asn Ala
                165                 170                 175

<210> SEQ ID NO 15
<211> LENGTH: 522
<212> TYPE: DNA
<213> ORGANISM: Escherichia coli
<220> FEATURE:
<221> NAME/KEY: CDS
<222> LOCATION: (1)..(522)

<400> SEQUENCE: 15

```
atg aat atg ggt ctt ttt tac ggt tcc agc acc tgt tac acc gaa atg       48
Met Asn Met Gly Leu Phe Tyr Gly Ser Ser Thr Cys Tyr Thr Glu Met
1               5                   10                  15 gcg gca gaa aaa atc cgc gat att atc ggc cca gaa ctg gtg acc tta       96
```

```
                                              -continued

Ala Ala Glu Lys Ile Arg Asp Ile Ile Gly Pro Glu Leu Val Thr Leu
            20                  25                  30 cat aac ctc aag gac gac tcc ccg aaa tta atg gag cag tac gat gtg      144
His Asn Leu Lys Asp Asp Ser Pro Lys Leu Met Glu Gln Tyr Asp Val
            35                  40                  45 ctc att ctg ggt atc ccg acc tgg gat ttt ggt gaa atc cag gaa gac      192
Leu Ile Leu Gly Ile Pro Thr Trp Asp Phe Gly Glu Ile Gln Glu Asp
 50                  55                  60 tgg gaa gcc gtc tgg gat cag ctc gac gac ctg aac ctt gaa ggt aaa      240
Trp Glu Ala Val Trp Asp Gln Leu Asp Asp Leu Asn Leu Glu Gly Lys
 65                  70                  75                  80 att gtt gcg ctg tat ggg ctt ggc gat caa ctg gga tac ggc gag tgg      288
Ile Val Ala Leu Tyr Gly Leu Gly Asp Gln Leu Gly Tyr Gly Glu Trp
                85                  90                  95 ttc ctc gat gcg ctc ggt atg ctg cat gac aaa ctc tcg acc aaa ggc      336
Phe Leu Asp Ala Leu Gly Met Leu His Asp Lys Leu Ser Thr Lys Gly
            100                 105                 110 gtg aag ttc gtc ggc tac tgg cca acg gaa gga tat gaa ttt acc agc      384
Val Lys Phe Val Gly Tyr Trp Pro Thr Glu Gly Tyr Glu Phe Thr Ser
            115                 120                 125 ccg aaa ccg gtg att gct gac ggg caa ctg ttc gtg ggt ctg gcg ctg      432
Pro Lys Pro Val Ile Ala Asp Gly Gln Leu Phe Val Gly Leu Ala Leu
130                 135                 140 gat gaa act aac cag tat gac ctt agc gac gag cgt att cag agc tgg      480
Asp Glu Thr Asn Gln Tyr Asp Leu Ser Asp Glu Arg Ile Gln Ser Trp
145                 150                 155                 160 tgc gag caa atc ctc aac gaa atg gca gag cat tac gcc tga              522
Cys Glu Gln Ile Leu Asn Glu Met Ala Glu His Tyr Ala
                165                 170

<210> SEQ ID NO 16
<211> LENGTH: 173
<212> TYPE: PRT
<213> ORGANISM: Escherichia coli

<400> SEQUENCE: 16

Met Asn Met Gly Leu Phe Tyr Gly Ser Ser Thr Cys Tyr Thr Glu Met
 1               5                  10                  15

Ala Ala Glu Lys Ile Arg Asp Ile Ile Gly Pro Glu Leu Val Thr Leu
            20                  25                  30

His Asn Leu Lys Asp Asp Ser Pro Lys Leu Met Glu Gln Tyr Asp Val
            35                  40                  45

Leu Ile Leu Gly Ile Pro Thr Trp Asp Phe Gly Glu Ile Gln Glu Asp
 50                  55                  60

Trp Glu Ala Val Trp Asp Gln Leu Asp Asp Leu Asn Leu Glu Gly Lys
 65                  70                  75                  80

Ile Val Ala Leu Tyr Gly Leu Gly Asp Gln Leu Gly Tyr Gly Glu Trp
                85                  90                  95

Phe Leu Asp Ala Leu Gly Met Leu His Asp Lys Leu Ser Thr Lys Gly
            100                 105                 110

Val Lys Phe Val Gly Tyr Trp Pro Thr Glu Gly Tyr Glu Phe Thr Ser
            115                 120                 125

Pro Lys Pro Val Ile Ala Asp Gly Gln Leu Phe Val Gly Leu Ala Leu
130                 135                 140

Asp Glu Thr Asn Gln Tyr Asp Leu Ser Asp Glu Arg Ile Gln Ser Trp
145                 150                 155                 160

Cys Glu Gln Ile Leu Asn Glu Met Ala Glu His Tyr Ala
                165                 170
```

<210> SEQ ID NO 17
<211> LENGTH: 522
<212> TYPE: DNA
<213> ORGANISM: Chlorobium tepidum
<220> FEATURE:
<221> NAME/KEY: CDS
<222> LOCATION: (1)..(522)

<400> SEQUENCE: 17

| atg | aat | atg | ggt | ctt | ttt | tac | ggt | tcc | agc | acc | tgt | tac | acc | gaa | atg | 48 |
| Met | Asn | Met | Gly | Leu | Phe | Tyr | Gly | Ser | Ser | Thr | Cys | Tyr | Thr | Glu | Met | |
| 1 | | | | 5 | | | | | 10 | | | | | 15 | | |

| gcg | gca | gaa | aaa | atc | cgc | gat | att | atc | ggc | cca | gaa | ctg | gtg | acc | tta | 96 |
| Ala | Ala | Glu | Lys | Ile | Arg | Asp | Ile | Ile | Gly | Pro | Glu | Leu | Val | Thr | Leu | |
| | | | 20 | | | | | 25 | | | | | 30 | | | |

| cat | aac | ctc | aag | gac | gac | tcc | ccg | aaa | tta | atg | gag | cag | tac | gat | gtg | 144 |
| His | Asn | Leu | Lys | Asp | Asp | Ser | Pro | Lys | Leu | Met | Glu | Gln | Tyr | Asp | Val | |
| | | | | 35 | | | | | 40 | | | | | 45 | | |

| ctc | att | ctg | ggt | atc | ccg | acc | tgg | gat | ttt | ggt | gaa | atc | cag | gaa | gac | 192 |
| Leu | Ile | Leu | Gly | Ile | Pro | Thr | Trp | Asp | Phe | Gly | Glu | Ile | Gln | Glu | Asp | |
| | 50 | | | | | 55 | | | | | 60 | | | | | |

| tgg | gaa | gcc | gtc | tgg | gat | cag | ctc | gac | gac | ctg | aac | ctt | gaa | ggt | aaa | 240 |
| Trp | Glu | Ala | Val | Trp | Asp | Gln | Leu | Asp | Asp | Leu | Asn | Leu | Glu | Gly | Lys | |
| 65 | | | | | 70 | | | | | 75 | | | | | 80 | |

| att | gtt | gcg | ctg | tat | ggg | ctt | ggc | gat | caa | ctg | gga | tac | ggc | gag | tgg | 288 |
| Ile | Val | Ala | Leu | Tyr | Gly | Leu | Gly | Asp | Gln | Leu | Gly | Tyr | Gly | Glu | Trp | |
| | | | | 85 | | | | | 90 | | | | | 95 | | |

| ttc | ctc | gat | gcg | ctc | ggt | atg | ctg | cat | gac | aaa | ctc | tcg | acc | aaa | ggc | 336 |
| Phe | Leu | Asp | Ala | Leu | Gly | Met | Leu | His | Asp | Lys | Leu | Ser | Thr | Lys | Gly | |
| | | | 100 | | | | | 105 | | | | | 110 | | | |

| gtg | aag | ttc | gtc | ggc | tac | tgg | cca | acg | gaa | gga | tat | gaa | ttt | acc | agc | 384 |
| Val | Lys | Phe | Val | Gly | Tyr | Trp | Pro | Thr | Glu | Gly | Tyr | Glu | Phe | Thr | Ser | |
| | | | 115 | | | | | 120 | | | | | 125 | | | |

| ccg | aaa | ccg | gtg | att | gct | gac | ggg | caa | ctg | ttc | gtg | ggt | ctg | gcg | ctg | 432 |
| Pro | Lys | Pro | Val | Ile | Ala | Asp | Gly | Gln | Leu | Phe | Val | Gly | Leu | Ala | Leu | |
| | | 130 | | | | | 135 | | | | | 140 | | | | |

| gat | gaa | act | aac | cag | tat | gac | ctt | agc | gac | gag | cgt | att | cag | agc | tgg | 480 |
| Asp | Glu | Thr | Asn | Gln | Tyr | Asp | Leu | Ser | Asp | Glu | Arg | Ile | Gln | Ser | Trp | |
| 145 | | | | | 150 | | | | | 155 | | | | | 160 | |

| tgc | gag | caa | atc | ctc | aac | gaa | atg | gca | gag | cat | tac | gcc | tga | | | 522 |
| Cys | Glu | Gln | Ile | Leu | Asn | Glu | Met | Ala | Glu | His | Tyr | Ala | | | | |
| | | | | 165 | | | | | 170 | | | | | | | |

<210> SEQ ID NO 18
<211> LENGTH: 173
<212> TYPE: PRT
<213> ORGANISM: Chlorobium tepidum

<400> SEQUENCE: 18

| Met | Asn | Met | Gly | Leu | Phe | Tyr | Gly | Ser | Ser | Thr | Cys | Tyr | Thr | Glu | Met |
| 1 | | | | 5 | | | | | 10 | | | | | 15 | |

| Ala | Ala | Glu | Lys | Ile | Arg | Asp | Ile | Ile | Gly | Pro | Glu | Leu | Val | Thr | Leu |
| | | | 20 | | | | | 25 | | | | | 30 | | |

| His | Asn | Leu | Lys | Asp | Asp | Ser | Pro | Lys | Leu | Met | Glu | Gln | Tyr | Asp | Val |
| | | | | 35 | | | | | 40 | | | | | 45 | |

| Leu | Ile | Leu | Gly | Ile | Pro | Thr | Trp | Asp | Phe | Gly | Glu | Ile | Gln | Glu | Asp |
| | 50 | | | | | 55 | | | | | 60 | | | | |

| Trp | Glu | Ala | Val | Trp | Asp | Gln | Leu | Asp | Asp | Leu | Asn | Leu | Glu | Gly | Lys |
| 65 | | | | | 70 | | | | | 75 | | | | | 80 | |

```
Ile Val Ala Leu Tyr Gly Leu Gly Asp Gln Leu Gly Tyr Gly Glu Trp
                85                  90                  95

Phe Leu Asp Ala Leu Gly Met Leu His Asp Lys Leu Ser Thr Lys Gly
            100                 105                 110

Val Lys Phe Val Gly Tyr Trp Pro Thr Glu Gly Tyr Glu Phe Thr Ser
        115                 120                 125

Pro Lys Pro Val Ile Ala Asp Gly Gln Leu Phe Val Gly Leu Ala Leu
    130                 135                 140

Asp Glu Thr Asn Gln Tyr Asp Leu Ser Asp Glu Arg Ile Gln Ser Trp
145                 150                 155                 160

Cys Glu Gln Ile Leu Asn Glu Met Ala Glu His Tyr Ala
                165                 170

<210> SEQ ID NO 19
<211> LENGTH: 189
<212> TYPE: DNA
<213> ORGANISM: Chlorobium tepidum
<220> FEATURE:
<221> NAME/KEY: CDS
<222> LOCATION: (1)..(189)

<400> SEQUENCE: 19 atg gca ctg tat atc acc gaa gaa tgc acc tac tgc ggt gct tgc gaa      48
Met Ala Leu Tyr Ile Thr Glu Glu Cys Thr Tyr Cys Gly Ala Cys Glu
1               5                   10                  15 ccc gaa tgc ccg acc aac gct atc tcc gct ggc agc gag atc tac gtt      96
Pro Glu Cys Pro Thr Asn Ala Ile Ser Ala Gly Ser Glu Ile Tyr Val
            20                  25                  30 atc gat gcc gca tcc tgc aac gag tgc gcc ggt ttt gct gac tct cct     144
Ile Asp Ala Ala Ser Cys Asn Glu Cys Ala Gly Phe Ala Asp Ser Pro
        35                  40                  45 gct tgc gtt gct gtc tgc ccg gca gag tgc atc gtt cag ggc tga         189
Ala Cys Val Ala Val Cys Pro Ala Glu Cys Ile Val Gln Gly
    50                  55                  60

<210> SEQ ID NO 20
<211> LENGTH: 62
<212> TYPE: PRT
<213> ORGANISM: Chlorobium tepidum

<400> SEQUENCE: 20

Met Ala Leu Tyr Ile Thr Glu Glu Cys Thr Tyr Cys Gly Ala Cys Glu
1               5                   10                  15

Pro Glu Cys Pro Thr Asn Ala Ile Ser Ala Gly Ser Glu Ile Tyr Val
            20                  25                  30

Ile Asp Ala Ala Ser Cys Asn Glu Cys Ala Gly Phe Ala Asp Ser Pro
        35                  40                  45

Ala Cys Val Ala Val Cys Pro Ala Glu Cys Ile Val Gln Gly
    50                  55                  60

<210> SEQ ID NO 21
<211> LENGTH: 2676
<212> TYPE: DNA
<213> ORGANISM: Escherichia coli
<220> FEATURE:
<221> NAME/KEY: CDS
<222> LOCATION: (1)..(2676)

<400> SEQUENCE: 21 atg gct gtt act aat gtc gct gaa ctt aac gca ctc gta gag cgt gta      48
Met Ala Val Thr Asn Val Ala Glu Leu Asn Ala Leu Val Glu Arg Val
1               5                   10                  15
```

-continued

```
aaa aaa gcc cag cgt gaa tat gcc agt ttc act caa gag caa gta gac      96
Lys Lys Ala Gln Arg Glu Tyr Ala Ser Phe Thr Gln Glu Gln Val Asp
         20                  25                  30 aaa atc ttc cgc gcc gcc gct ctg gct gct gca gat gct cga atc cca     144
Lys Ile Phe Arg Ala Ala Ala Leu Ala Ala Ala Asp Ala Arg Ile Pro
 35                  40                  45 ctc gcg aaa atg gcc gtt gcc gaa tcc ggc atg ggt atc gtc gaa gat     192
Leu Ala Lys Met Ala Val Ala Glu Ser Gly Met Gly Ile Val Glu Asp
         50                  55                  60 aaa gtg atc aaa aac cac ttt gct tct gaa tat atc tac aac gcc tat     240
Lys Val Ile Lys Asn His Phe Ala Ser Glu Tyr Ile Tyr Asn Ala Tyr
 65                  70                  75                  80 aaa gat gaa aaa acc tgt ggt gtt ctg tct gaa gac gac act ttt ggt     288
Lys Asp Glu Lys Thr Cys Gly Val Leu Ser Glu Asp Asp Thr Phe Gly
             85                  90                  95 acc atc act atc gct gaa cca atc ggt att att tgc ggt atc gtt ccg     336
Thr Ile Thr Ile Ala Glu Pro Ile Gly Ile Ile Cys Gly Ile Val Pro
        100                 105                 110 acc act aac ccg act tca act gct atc ttc aaa tcg ctg atc agt ctg     384
Thr Thr Asn Pro Thr Ser Thr Ala Ile Phe Lys Ser Leu Ile Ser Leu
        115                 120                 125 aag acc cgt aac gcc att atc ttc tcc ccg cac ccg cgt gca aaa gat     432
Lys Thr Arg Asn Ala Ile Ile Phe Ser Pro His Pro Arg Ala Lys Asp
130                 135                 140 gcc acc aac aaa gcg gct gat atc gtt ctg cag gct gct atc gct gcc     480
Ala Thr Asn Lys Ala Ala Asp Ile Val Leu Gln Ala Ala Ile Ala Ala
145                 150                 155                 160 ggt gct ccg aaa gat ctg atc ggc tgg atc gat caa cct tct gtt gaa     528
Gly Ala Pro Lys Asp Leu Ile Gly Trp Ile Asp Gln Pro Ser Val Glu
                165                 170                 175 ctg tct aac gca ctg atg cac cac cca gac atc aac ctg atc ctc gcg     576
Leu Ser Asn Ala Leu Met His His Pro Asp Ile Asn Leu Ile Leu Ala
            180                 185                 190 act ggt ggt ccg ggc atg gtt aaa gcc gca tac agc tcc ggt aaa cca     624
Thr Gly Gly Pro Gly Met Val Lys Ala Ala Tyr Ser Ser Gly Lys Pro
        195                 200                 205 gct atc ggt gta ggc gcg ggc aac act cca gtt gtt atc gat gaa act     672
Ala Ile Gly Val Gly Ala Gly Asn Thr Pro Val Val Ile Asp Glu Thr
210                 215                 220 gct gat atc aaa cgt gca gtt gca tct gta ctg atg tcc aaa acc ttc     720
Ala Asp Ile Lys Arg Ala Val Ala Ser Val Leu Met Ser Lys Thr Phe
225                 230                 235                 240 gac aac ggc gta atc tgt gct tct gaa cag tct gtt gtt gtt gtt gac     768
Asp Asn Gly Val Ile Cys Ala Ser Glu Gln Ser Val Val Val Val Asp
                245                 250                 255 tct gtt tat gac gct gta cgt gaa cgt ttt gca acc cac ggc ggc tat     816
Ser Val Tyr Asp Ala Val Arg Glu Arg Phe Ala Thr His Gly Gly Tyr
            260                 265                 270 ctg ttg cag ggt aaa gag ctg aaa gct gtt cag gat gtt atc ctg aaa     864
Leu Leu Gln Gly Lys Glu Leu Lys Ala Val Gln Asp Val Ile Leu Lys
        275                 280                 285 aac ggt gcg ctg aac gcg gct atc gtt ggt cag cca gcc tat aaa att     912
Asn Gly Ala Leu Asn Ala Ala Ile Val Gly Gln Pro Ala Tyr Lys Ile
290                 295                 300 gct gaa ctg gca ggc ttc tct gta cca gaa aac acc aag att ctg atc     960
Ala Glu Leu Ala Gly Phe Ser Val Pro Glu Asn Thr Lys Ile Leu Ile
305                 310                 315                 320 ggt gaa gtg acc gtt gtt gat gaa agc gaa ccg ttc gca cat gaa aaa    1008
Gly Glu Val Thr Val Val Asp Glu Ser Glu Pro Phe Ala His Glu Lys
```

```
                325             330             335
ctg tcc ccg act ctg gca atg tac cgc gct aaa gat ttc gaa gac gcg    1056
Leu Ser Pro Thr Leu Ala Met Tyr Arg Ala Lys Asp Phe Glu Asp Ala
        340             345             350 gta gaa aaa gca gag aaa ctg gtt gct atg ggc ggt atc ggt cat acc    1104
Val Glu Lys Ala Glu Lys Leu Val Ala Met Gly Gly Ile Gly His Thr
355             360             365 tct tgc ctg tac act gac cag gat aac caa ccg gct cgc gtt tct tac    1152
Ser Cys Leu Tyr Thr Asp Gln Asp Asn Gln Pro Ala Arg Val Ser Tyr
        370             375             380 ttc ggt cag aaa atg aaa acg gcg cgt atc ctg att aac acc cca gcg    1200
Phe Gly Gln Lys Met Lys Thr Ala Arg Ile Leu Ile Asn Thr Pro Ala
385             390             395             400 tct cag ggt ggt atc ggt gac ctg tat aac ttc aaa ctc gca cct tcc    1248
Ser Gln Gly Gly Ile Gly Asp Leu Tyr Asn Phe Lys Leu Ala Pro Ser
        405             410             415 ctg act ctg ggt tgt ggt tct tgg ggt ggt aac tcc atc tct gaa aac    1296
Leu Thr Leu Gly Cys Gly Ser Trp Gly Gly Asn Ser Ile Ser Glu Asn
        420             425             430 gtt ggt ccg aaa cac ctg atc aac aag aaa acc gtt gct aag cga gct    1344
Val Gly Pro Lys His Leu Ile Asn Lys Lys Thr Val Ala Lys Arg Ala
        435             440             445 gaa aac atg ttg tgg cac aaa ctt ccg aaa tct atc tac ttc cgc cgt    1392
Glu Asn Met Leu Trp His Lys Leu Pro Lys Ser Ile Tyr Phe Arg Arg
450             455             460 ggc tcc ctg cca atc gcg ctg gat gaa gtg att act gat ggc cac aaa    1440
Gly Ser Leu Pro Ile Ala Leu Asp Glu Val Ile Thr Asp Gly His Lys
465             470             475             480 cgt gcg ctc atc gtg act gac cgc ttc ctg ttc aac aat ggt tat gct    1488
Arg Ala Leu Ile Val Thr Asp Arg Phe Leu Phe Asn Asn Gly Tyr Ala
        485             490             495 gat cag atc act tcc gta ctg aaa gca gca ggc gtt gaa act gaa gtc    1536
Asp Gln Ile Thr Ser Val Leu Lys Ala Ala Gly Val Glu Thr Glu Val
        500             505             510 ttc ttc gaa gta gaa gcg gac ccg acc ctg agc atc gtt cgt aaa ggt    1584
Phe Phe Glu Val Glu Ala Asp Pro Thr Leu Ser Ile Val Arg Lys Gly
        515             520             525 gca gaa ctg gca aac tcc ttc aaa cca gac gtg att atc gcg ctg ggt    1632
Ala Glu Leu Ala Asn Ser Phe Lys Pro Asp Val Ile Ile Ala Leu Gly
530             535             540 ggt ggt tcc ccg atg gac gcc gcg aag atc atg tgg gtt atg tac gaa    1680
Gly Gly Ser Pro Met Asp Ala Ala Lys Ile Met Trp Val Met Tyr Glu
545             550             555             560 cat ccg gaa act cac ttc gaa gag ctg gcg ctg cgc ttt atg gat atc    1728
His Pro Glu Thr His Phe Glu Glu Leu Ala Leu Arg Phe Met Asp Ile
        565             570             575 cgt aaa cgt atc tac aag ttc ccg aaa atg ggc gtg aaa gcg aaa atg    1776
Arg Lys Arg Ile Tyr Lys Phe Pro Lys Met Gly Val Lys Ala Lys Met
        580             585             590 atc gct gtc acc acc act tct ggt aca ggt tct gaa gtc act ccg ttt    1824
Ile Ala Val Thr Thr Thr Ser Gly Thr Gly Ser Glu Val Thr Pro Phe
        595             600             605 gcg gtt gta act gac gac gct act ggt cag aaa tat ccg ctg gca gac    1872
Ala Val Val Thr Asp Asp Ala Thr Gly Gln Lys Tyr Pro Leu Ala Asp
        610             615             620 tat gcg ctg act ccg gat atg gcg att gtc gac gcc aac ctg gtt atg    1920
Tyr Ala Leu Thr Pro Asp Met Ala Ile Val Asp Ala Asn Leu Val Met
625             630             635             640 gac atg ccg aag tcc ctg tgt gct ttc ggt ggt ctg gac gca gta act    1968
```

```
Asp Met Pro Lys Ser Leu Cys Ala Phe Gly Gly Leu Asp Ala Val Thr
            645                 650                 655 cac gcc atg gaa gct tat gtt tct gta ctg gca tct gag ttc tct gat    2016
His Ala Met Glu Ala Tyr Val Ser Val Leu Ala Ser Glu Phe Ser Asp
        660                 665                 670 ggt cag gct ctg cag gca ctg aaa ctg ctg aaa gaa tat ctg cca gcg    2064
Gly Gln Ala Leu Gln Ala Leu Lys Leu Leu Lys Glu Tyr Leu Pro Ala
    675                 680                 685 tcc tac cac gaa ggg tct aaa aat ccg gta gcg cgt gaa cgt gtt cac    2112
Ser Tyr His Glu Gly Ser Lys Asn Pro Val Ala Arg Glu Arg Val His
690                 695                 700 agt gca gcg act atc gcg ggt atc gcg ttt gcg aac gcc ttc ctg ggt    2160
Ser Ala Ala Thr Ile Ala Gly Ile Ala Phe Ala Asn Ala Phe Leu Gly
705                 710                 715                 720 gta tgt cac tca atg gcg cac aaa ctg ggt tcc cag ttc cat att ccg    2208
Val Cys His Ser Met Ala His Lys Leu Gly Ser Gln Phe His Ile Pro
                725                 730                 735 cac ggt ctg gca aac gcc ctg ctg att tgt aac gtt att cgc tac aat    2256
His Gly Leu Ala Asn Ala Leu Leu Ile Cys Asn Val Ile Arg Tyr Asn
            740                 745                 750 gcg aac gac aac ccg acc aag cag act gca ttc agc cag tat gac cgt    2304
Ala Asn Asp Asn Pro Thr Lys Gln Thr Ala Phe Ser Gln Tyr Asp Arg
        755                 760                 765 ccg cag gct cgc cgt cgt tat gct gaa att gcc gac cac ttg ggt ctg    2352
Pro Gln Ala Arg Arg Arg Tyr Ala Glu Ile Ala Asp His Leu Gly Leu
    770                 775                 780 agc gca ccg ggc gac cgt act gct gct aag atc gag aaa ctg ctg gca    2400
Ser Ala Pro Gly Asp Arg Thr Ala Ala Lys Ile Glu Lys Leu Leu Ala
785                 790                 795                 800 tgg ctg gaa acg ctg aaa gct gaa ctg ggt att ccg aaa tct atc cgt    2448
Trp Leu Glu Thr Leu Lys Ala Glu Leu Gly Ile Pro Lys Ser Ile Arg
                805                 810                 815 gaa gct ggc gtt cag gaa gca gac ttc ctg gcg aac gtg gat aaa ctg    2496
Glu Ala Gly Val Gln Glu Ala Asp Phe Leu Ala Asn Val Asp Lys Leu
            820                 825                 830 tct gaa gat gca ttc gat gac cag tgc acc ggc gct aac ccg cgt tac    2544
Ser Glu Asp Ala Phe Asp Asp Gln Cys Thr Gly Ala Asn Pro Arg Tyr
        835                 840                 845 ccg ctg atc tcc gag ctg aaa cag att ctg ctg gat acc tac tac ggt    2592
Pro Leu Ile Ser Glu Leu Lys Gln Ile Leu Leu Asp Thr Tyr Tyr Gly
    850                 855                 860 cgt gat tat gta gaa ggt gaa act gca gcg aag aaa gaa gct gct ccg    2640
Arg Asp Tyr Val Glu Gly Glu Thr Ala Ala Lys Lys Glu Ala Ala Pro
865                 870                 875                 880 gct aaa gct gag aaa aaa gcg aaa aaa tcc gct taa                    2676
Ala Lys Ala Glu Lys Lys Ala Lys Lys Ser Ala
                885                 890

<210> SEQ ID NO 22
<211> LENGTH: 891
<212> TYPE: PRT
<213> ORGANISM: Escherichia coli

<400> SEQUENCE: 22

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45
```

-continued

```
Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Thr Phe Gly
                85                  90                  95

Thr Ile Thr Ile Ala Glu Pro Ile Gly Ile Ile Cys Gly Ile Val Pro
                100                 105                 110

Thr Thr Asn Pro Thr Ser Thr Ala Ile Phe Lys Ser Leu Ile Ser Leu
            115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
    450                 455                 460
```

-continued

```
Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ala Leu Gly
    530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
                580                 585                 590

Ile Ala Val Thr Thr Thr Ser Gly Thr Gly Ser Glu Val Thr Pro Phe
                595                 600                 605

Ala Val Val Thr Asp Asp Ala Thr Gly Gln Lys Tyr Pro Leu Ala Asp
610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
                740                 745                 750

Ala Asn Asp Asn Pro Thr Lys Gln Thr Ala Phe Ser Gln Tyr Asp Arg
                755                 760                 765

Pro Gln Ala Arg Arg Arg Tyr Ala Glu Ile Ala Asp His Leu Gly Leu
770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Asp Gln Cys Thr Gly Ala Asn Pro Arg Tyr
            835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
```

<210> SEQ ID NO 23
<211> LENGTH: 69
<212> TYPE: DNA
<213> ORGANISM: Artificial
<220> FEATURE:
<223> OTHER INFORMATION: primer

<400> SEQUENCE: 23
cgttattgtt atctagttgt gcaaaacatg ctaatgtagc attacgcccc gccctgccac      60
tcatcgcag                                                             69

<210> SEQ ID NO 24
<211> LENGTH: 58
<212> TYPE: DNA
<213> ORGANISM: Artificial
<220> FEATURE:
<223> OTHER INFORMATION: primer

<400> SEQUENCE: 24
attagtaaca gccataatgc tctcctgata atgttaaacc gctcacaatt ccacacat       58

<210> SEQ ID NO 25
<211> LENGTH: 183
<212> TYPE: DNA
<213> ORGANISM: Artificial
<220> FEATURE:
<223> OTHER INFORMATION: hybrid promoter

<400> SEQUENCE: 25
ctagatctct cacctaccaa acaatgcccc cctgcaaaaa ataaattcat aaaaaacata     60
cagataacca tctgcggtga taaattatct ctggcggtgt tgacaattaa tcatcggctc    120
gtataatgtg tggaattgtg agcggtttaa cattatcagg agagcattat ggctgttact    180
aat                                                                  183

<210> SEQ ID NO 26
<211> LENGTH: 24
<212> TYPE: DNA
<213> ORGANISM: Artificial
<220> FEATURE:
<223> OTHER INFORMATION: primer

<400> SEQUENCE: 26
acttgttctt gagtgaaact ggca                                           24

<210> SEQ ID NO 27
<211> LENGTH: 22
<212> TYPE: DNA
<213> ORGANISM: Artificial
<220> FEATURE:
<223> OTHER INFORMATION: primer

<400> SEQUENCE: 27
aagacgcgct gacaatacgc ct                                             22

<210> SEQ ID NO 28
<211> LENGTH: 69
<212> TYPE: DNA
<213> ORGANISM: Artificial
<220> FEATURE:
<223> OTHER INFORMATION: primer

<400> SEQUENCE: 28

```
cgttattgtt atctagttgt gcaaaacatg ctaatgtagc atcagaaaaa ctcatcgagc    60
atcaaatga                                                           69

<210> SEQ ID NO 29
<211> LENGTH: 65
<212> TYPE: DNA
<213> ORGANISM: Artificial
<220> FEATURE:
<223> OTHER INFORMATION: primer

<400> SEQUENCE: 29
agccggagca gcttctttct tcgctgcagt ttcaccttct acgttgtgtc tcaaaatctc    60
tgatg                                                               65

<210> SEQ ID NO 30
<211> LENGTH: 24
<212> TYPE: DNA
<213> ORGANISM: Artificial
<220> FEATURE:
<223> OTHER INFORMATION: primer

<400> SEQUENCE: 30
aagacgcgct gacaatacgc cttt                                          24

<210> SEQ ID NO 31
<211> LENGTH: 24
<212> TYPE: DNA
<213> ORGANISM: Artificial
<220> FEATURE:
<223> OTHER INFORMATION: primer

<400> SEQUENCE: 31
aaggggccgt ttatgttgcc agac                                          24

<210> SEQ ID NO 32
<211> LENGTH: 69
<212> TYPE: DNA
<213> ORGANISM: Artificial
<220> FEATURE:
<223> OTHER INFORMATION: primer

<400> SEQUENCE: 32
catgtgggtt atgtacgaac atccggaaac tcacttcgaa aagctggcgc tgcgctttat    60
ggatatccg                                                           69

<210> SEQ ID NO 33
<211> LENGTH: 24
<212> TYPE: DNA
<213> ORGANISM: Artificial
<220> FEATURE:
<223> OTHER INFORMATION: primer

<400> SEQUENCE: 33
aaggggccgt ttatgttgcc agac                                          24

<210> SEQ ID NO 34
<211> LENGTH: 24
<212> TYPE: DNA
<213> ORGANISM: Artificial
<220> FEATURE:
<223> OTHER INFORMATION: primer

<400> SEQUENCE: 34
```
aagacgcgct gacaatacgc cttt                                           24

<210> SEQ ID NO 35
<211> LENGTH: 51
<212> TYPE: DNA
<213> ORGANISM: Artificial
<220> FEATURE:
<223> OTHER INFORMATION: primer

<400> SEQUENCE: 35
ttttctagat aaggaggaat gacgtatgac ccggacattc aagacaatgg a             51

<210> SEQ ID NO 36
<211> LENGTH: 39
<212> TYPE: DNA
<213> ORGANISM: Artificial
<220> FEATURE:
<223> OTHER INFORMATION: primer

<400> SEQUENCE: 36
aaatctagat tcagcttatg cttcgccttc aatcgaacg                           39

<210> SEQ ID NO 37
<211> LENGTH: 344
<212> TYPE: DNA
<213> ORGANISM: Escherichia coli

<400> SEQUENCE: 37
aagctttacg cgaacgagcc atgacattgc tgacgactct ggcagtggca gatgacataa   60
aactggtcga ctggttacaa caacgcctgg ggcttttaga gcaacgagac acggcaatgt  120
tgcaccgttt gctgcatgat attgaaaaaa atatccaccaa ataaaaaacg ccttagtaag  180
tattttcag cttttcattc tgactgcaac gggcaatatg tctctgtgtg gattaaaaaa   240
agagtgtctg atagcagctt ctgaactggt tacctgccgt gagtaaatta aaatttttatt  300
gacttaggtc actaaatact ttaaccaata taggcgactc taga                   344

<210> SEQ ID NO 38
<211> LENGTH: 53
<212> TYPE: DNA
<213> ORGANISM: Artificial
<220> FEATURE:
<223> OTHER INFORMATION: primer

<400> SEQUENCE: 38
ttttctggta cctaaggagg aatgacgtat gattactatt gacggtaatg gcg          53

<210> SEQ ID NO 39
<211> LENGTH: 40
<212> TYPE: DNA
<213> ORGANISM: Artificial
<220> FEATURE:
<223> OTHER INFORMATION: primer

<400> SEQUENCE: 39
gagagaccgg gtaccttaat cggtgttgct tttttccgct                         40

<210> SEQ ID NO 40
<211> LENGTH: 49
<212> TYPE: DNA
<213> ORGANISM: Artificial
<220> FEATURE:
<223> OTHER INFORMATION: primer

<400> SEQUENCE: 40

```
aattggtacc taaggaggaa tgacgtatga ccagtggccc aaaaccggc                49
```

<210> SEQ ID NO 41
<211> LENGTH: 42
<212> TYPE: DNA
<213> ORGANISM: Artificial
<220> FEATURE:
<223> OTHER INFORMATION: primer

<400> SEQUENCE: 41

```
gcgacgccta gcttagggta ccttaccatg cctcgatatt gt                       42
```

<210> SEQ ID NO 42
<211> LENGTH: 35
<212> TYPE: DNA
<213> ORGANISM: Artificial
<220> FEATURE:
<223> OTHER INFORMATION: primer

<400> SEQUENCE: 42

```
ctctctggcc ccgggctgat tgatttgatc gattg                               35
```

<210> SEQ ID NO 43
<211> LENGTH: 33
<212> TYPE: DNA
<213> ORGANISM: Artificial
<220> FEATURE:
<223> OTHER INFORMATION: primer

<400> SEQUENCE: 43

```
gagagacccc gggttaccag taatgctccg ctg                                 33
```

<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44

```
gcgcgaattc gggcgatgat gttgacgcca                                     30
```

<210> SEQ ID NO 45
<211> LENGTH: 30
<212> TYPE: DNA
<213> ORGANISM: Artificial
<220> FEATURE:
<223> OTHER INFORMATION: primer

<400> SEQUENCE: 45

```
gcgcgaattc gtcccatact aacctctgtt                                     30
```

<210> SEQ ID NO 46
<211> LENGTH: 2664
<212> TYPE: DNA
<213> ORGANISM: Escherichia coli
<220> FEATURE:
<221> NAME/KEY: CDS
<222> LOCATION: (1)..(2664)

<400> SEQUENCE: 46

```
atg tca gaa cgt ttc cca aat gac gtg gat ccg atc gaa act cgc gac      48
Met Ser Glu Arg Phe Pro Asn Asp Val Asp Pro Ile Glu Thr Arg Asp
1               5                   10                  15 tgg ctc cag gcg atc gaa tcg gtc atc cgt gaa gaa ggt gtt gag cgt      96
```

```
Trp Leu Gln Ala Ile Glu Ser Val Ile Arg Glu Glu Gly Val Glu Arg
            20                  25                  30 gct cag tat ctg atc gac caa ctg ctt gct gaa gcc cgc aaa ggc ggt    144
Ala Gln Tyr Leu Ile Asp Gln Leu Leu Ala Glu Ala Arg Lys Gly Gly
        35                  40                  45 gta aac gta gcc gca ggc aca ggt atc agc aac tac atc aac acc atc    192
Val Asn Val Ala Ala Gly Thr Gly Ile Ser Asn Tyr Ile Asn Thr Ile
 50                  55                  60 ccc gtt gaa gaa caa ccg gag tat ccg ggt aat ctg gaa ctg gaa cgc    240
Pro Val Glu Glu Gln Pro Glu Tyr Pro Gly Asn Leu Glu Leu Glu Arg
 65                  70                  75                  80 cgt att cgt tca gct atc cgc tgg aac gcc atc atg acg gtg ctg cgt    288
Arg Ile Arg Ser Ala Ile Arg Trp Asn Ala Ile Met Thr Val Leu Arg
                85                  90                  95 gcg tcg aaa aaa gac ctc gaa ctg ggc ggc cat atg gcg tcc ttc cag    336
Ala Ser Lys Lys Asp Leu Glu Leu Gly Gly His Met Ala Ser Phe Gln
            100                 105                 110 tct tcc gca acc att tat gat gtg tgc ttt aac cac ttc ttc cgt gca    384
Ser Ser Ala Thr Ile Tyr Asp Val Cys Phe Asn His Phe Phe Arg Ala
        115                 120                 125 cgc aac gag cag gat ggc ggc gac ctg gtt tac ttc cag ggc cac atc    432
Arg Asn Glu Gln Asp Gly Gly Asp Leu Val Tyr Phe Gln Gly His Ile
130                 135                 140 tcc ccg ggc gtg tac gct cgt gct ttc ctg gaa ggt cgt ctg act cag    480
Ser Pro Gly Val Tyr Ala Arg Ala Phe Leu Glu Gly Arg Leu Thr Gln
145                 150                 155                 160 gag cag ctg gat aac ttc cgt cag gaa gtt cac ggc aat ggc ctc tct    528
Glu Gln Leu Asp Asn Phe Arg Gln Glu Val His Gly Asn Gly Leu Ser
                165                 170                 175 tcc tat ccg cac ccg aaa ctg atg ccg gaa ttc tgg cag ttc ccg acc    576
Ser Tyr Pro His Pro Lys Leu Met Pro Glu Phe Trp Gln Phe Pro Thr
            180                 185                 190 gta tct atg ggt ctg ggt ccg att ggt gct att tac cag gct aaa ttc    624
Val Ser Met Gly Leu Gly Pro Ile Gly Ala Ile Tyr Gln Ala Lys Phe
        195                 200                 205 ctg aaa tat ctg gaa cac cgt ggc ctg aaa gat acc tct aaa caa acc    672
Leu Lys Tyr Leu Glu His Arg Gly Leu Lys Asp Thr Ser Lys Gln Thr
210                 215                 220 gtt tac gcg ttc ctc ggt gac ggt gaa atg gac gaa ccg gaa tcc aaa    720
Val Tyr Ala Phe Leu Gly Asp Gly Glu Met Asp Glu Pro Glu Ser Lys
225                 230                 235                 240 ggt gcg atc acc atc gct acc cgt gaa aaa ctg gat aac ctg gtc ttc    768
Gly Ala Ile Thr Ile Ala Thr Arg Glu Lys Leu Asp Asn Leu Val Phe
                245                 250                 255 gtt atc aac tgt aac ctg cag cgt ctt gac ggc ccg gtc acc ggt aac    816
Val Ile Asn Cys Asn Leu Gln Arg Leu Asp Gly Pro Val Thr Gly Asn
            260                 265                 270 ggc aag atc atc aac gaa ctg gaa ggc atc ttc gaa ggt gct ggc tgg    864
Gly Lys Ile Ile Asn Glu Leu Glu Gly Ile Phe Glu Gly Ala Gly Trp
        275                 280                 285 aac gtg atc aaa gtg atg tgg ggt agc cgt tgg gat gaa ctg ctg cgt    912
Asn Val Ile Lys Val Met Trp Gly Ser Arg Trp Asp Glu Leu Leu Arg
290                 295                 300 aag gat acc agc ggt aaa ctg atc cag ctg atg aac gaa acc gtt gac    960
Lys Asp Thr Ser Gly Lys Leu Ile Gln Leu Met Asn Glu Thr Val Asp
305                 310                 315                 320 ggc gac tac cag acc ttc aaa tcg aaa gat ggt gcg tac gtt cgt gaa   1008
Gly Asp Tyr Gln Thr Phe Lys Ser Lys Asp Gly Ala Tyr Val Arg Glu
                325                 330                 335
```

```
cac ttc ttc ggt aaa tat cct gaa acc gca gca ctg gtt gca gac tgg    1056
His Phe Phe Gly Lys Tyr Pro Glu Thr Ala Ala Leu Val Ala Asp Trp
            340                 345                 350 act gac gag cag atc tgg gca ctg aac cgt ggt ggt cac gat ccg aag    1104
Thr Asp Glu Gln Ile Trp Ala Leu Asn Arg Gly Gly His Asp Pro Lys
        355                 360                 365 aaa atc tac gct gca ttc aag aaa gcg cag gaa acc aaa ggc aaa gcg    1152
Lys Ile Tyr Ala Ala Phe Lys Lys Ala Gln Glu Thr Lys Gly Lys Ala
    370                 375                 380 aca gta atc ctt gct cat acc att aaa ggt tac ggc atg ggc gac gcg    1200
Thr Val Ile Leu Ala His Thr Ile Lys Gly Tyr Gly Met Gly Asp Ala
385                 390                 395                 400 gct gaa ggt aaa aac atc gcg cac cag gtt aag aaa atg aac atg gac    1248
Ala Glu Gly Lys Asn Ile Ala His Gln Val Lys Lys Met Asn Met Asp
                405                 410                 415 ggt gtg cgt cat atc cgc gac cgt ttc aat gtg ccg gtg tct gat gca    1296
Gly Val Arg His Ile Arg Asp Arg Phe Asn Val Pro Val Ser Asp Ala
            420                 425                 430 gat atc gaa aaa ctg ccg tac atc acc ttc ccg gaa ggt tct gaa gag    1344
Asp Ile Glu Lys Leu Pro Tyr Ile Thr Phe Pro Glu Gly Ser Glu Glu
        435                 440                 445 cat acc tat ctg cac gct cag cgt cag aaa ctg cac ggt tat ctg cca    1392
His Thr Tyr Leu His Ala Gln Arg Gln Lys Leu His Gly Tyr Leu Pro
    450                 455                 460 agc cgt cag ccg aac ttc acc gag aag ctt gag ctg ccg agc ctg caa    1440
Ser Arg Gln Pro Asn Phe Thr Glu Lys Leu Glu Leu Pro Ser Leu Gln
465                 470                 475                 480 gac ttc ggc gcg ctg ttg gaa gag cag agc aaa gag atc tct acc act    1488
Asp Phe Gly Ala Leu Leu Glu Glu Gln Ser Lys Glu Ile Ser Thr Thr
                485                 490                 495 atc gct ttc gtt cgt gct ctg aac gtg atg ctg aag aac aag tcg atc    1536
Ile Ala Phe Val Arg Ala Leu Asn Val Met Leu Lys Asn Lys Ser Ile
            500                 505                 510 aaa gat cgt ctg gta ccg atc atc gcc gac gaa gcg cgt act ttc ggt    1584
Lys Asp Arg Leu Val Pro Ile Ile Ala Asp Glu Ala Arg Thr Phe Gly
        515                 520                 525 atg gaa ggt ctg ttc cgt cag att ggt att tac agc ccg aac ggt cag    1632
Met Glu Gly Leu Phe Arg Gln Ile Gly Ile Tyr Ser Pro Asn Gly Gln
    530                 535                 540 cag tac acc ccg cag gac cgc gag cag gtt gct tac tat aaa gaa gac    1680
Gln Tyr Thr Pro Gln Asp Arg Glu Gln Val Ala Tyr Tyr Lys Glu Asp
545                 550                 555                 560 gag aaa ggt cag att ctg cag gaa ggg atc aac gag ctg ggc gca ggt    1728
Glu Lys Gly Gln Ile Leu Gln Glu Gly Ile Asn Glu Leu Gly Ala Gly
                565                 570                 575 tgt tcc tgg ctg gca gcg gcg acc tct tac agc acc aac aat ctg ccg    1776
Cys Ser Trp Leu Ala Ala Ala Thr Ser Tyr Ser Thr Asn Asn Leu Pro
            580                 585                 590 atg atc ccg ttc tac atc tat tac tcg atg ttc ggc ttc cag cgt att    1824
Met Ile Pro Phe Tyr Ile Tyr Tyr Ser Met Phe Gly Phe Gln Arg Ile
        595                 600                 605 ggc gat ctg tgc tgg gcg gct ggc gac cag caa gcg cgt ggc ttc ctg    1872
Gly Asp Leu Cys Trp Ala Ala Gly Asp Gln Gln Ala Arg Gly Phe Leu
    610                 615                 620 atc ggc ggt act tcc ggt cgt acc acc ctg aac ggc gaa ggt ctg cag    1920
Ile Gly Gly Thr Ser Gly Arg Thr Thr Leu Asn Gly Glu Gly Leu Gln
625                 630                 635                 640 cac gaa gat ggt cac agc cac att cag tcg ctg act atc ccg aac tgt    1968
His Glu Asp Gly His Ser His Ile Gln Ser Leu Thr Ile Pro Asn Cys
                645                 650                 655
```

```
atc tct tac gac ccg gct tac gct tac gaa gtt gct gtc atc atg cat    2016
Ile Ser Tyr Asp Pro Ala Tyr Ala Tyr Glu Val Ala Val Ile Met His
        660                 665                 670 gac ggt ctg gag cgt atg tac ggt gaa aaa caa gag aac gtt tac tac    2064
Asp Gly Leu Glu Arg Met Tyr Gly Glu Lys Gln Glu Asn Val Tyr Tyr
    675                 680                 685 tac atc act acg ctg aac gaa aac tac cac atg ccg gca atg ccg gaa    2112
Tyr Ile Thr Thr Leu Asn Glu Asn Tyr His Met Pro Ala Met Pro Glu
690                 695                 700 ggt gct gag gaa ggt atc cgt aaa ggt atc tac aaa ctc gaa act att    2160
Gly Ala Glu Glu Gly Ile Arg Lys Gly Ile Tyr Lys Leu Glu Thr Ile
705                 710                 715                 720 gaa ggt agc aaa ggt aaa gtt cag ctc ctc ggc tcc ggt tct atc ctg    2208
Glu Gly Ser Lys Gly Lys Val Gln Leu Leu Gly Ser Gly Ser Ile Leu
                725                 730                 735 cgt cac gtc cgt gaa gca gct gag atc ctg gcg aaa gat tac ggc gta    2256
Arg His Val Arg Glu Ala Ala Glu Ile Leu Ala Lys Asp Tyr Gly Val
            740                 745                 750 ggt tct gac gtt tat agc gtg acc tcc ttc acc gag ctg gcg cgt gat    2304
Gly Ser Asp Val Tyr Ser Val Thr Ser Phe Thr Glu Leu Ala Arg Asp
        755                 760                 765 ggt cag gat tgt gaa cgc tgg aac atg ctg cac ccg ctg gaa act ccg    2352
Gly Gln Asp Cys Glu Arg Trp Asn Met Leu His Pro Leu Glu Thr Pro
    770                 775                 780 cgc gtt ccg tat atc gct cag gtg atg aac gac gct ccg gca gtg gca    2400
Arg Val Pro Tyr Ile Ala Gln Val Met Asn Asp Ala Pro Ala Val Ala
785                 790                 795                 800 tct acc gac tat atg aaa ctg ttc gct gag cag gtc cgt act tac gta    2448
Ser Thr Asp Tyr Met Lys Leu Phe Ala Glu Gln Val Arg Thr Tyr Val
                805                 810                 815 ccg gct gac gac tac cgc gta ctg ggt act gat ggc ttc ggt cgt tcc    2496
Pro Ala Asp Asp Tyr Arg Val Leu Gly Thr Asp Gly Phe Gly Arg Ser
            820                 825                 830 gac agc cgt gag aac ctg cgt cac cac ttc gaa gtt gat gct tct tat    2544
Asp Ser Arg Glu Asn Leu Arg His His Phe Glu Val Asp Ala Ser Tyr
        835                 840                 845 gtc gtg gtt gcg gcg ctg ggc gaa ctg gct aaa cgt ggc gaa atc gat    2592
Val Val Val Ala Ala Leu Gly Glu Leu Ala Lys Arg Gly Glu Ile Asp
    850                 855                 860 aag aaa gtg gtt gct gac gca atc gcc aaa ttc aac atc gat gca gat    2640
Lys Lys Val Val Ala Asp Ala Ile Ala Lys Phe Asn Ile Asp Ala Asp
865                 870                 875                 880 aaa gtt aac ccg cgt ctg gcg taa                                    2664
Lys Val Asn Pro Arg Leu Ala
                885

<210> SEQ ID NO 47
<211> LENGTH: 887
<212> TYPE: PRT
<213> ORGANISM: Escherichia coli

<400> SEQUENCE: 47

Met Ser Glu Arg Phe Pro Asn Asp Val Asp Pro Ile Glu Thr Arg Asp
1               5                   10                  15

Trp Leu Gln Ala Ile Glu Ser Val Ile Arg Glu Glu Gly Val Glu Arg
            20                  25                  30

Ala Gln Tyr Leu Ile Asp Gln Leu Leu Ala Glu Ala Arg Lys Gly Gly
        35                  40                  45

Val Asn Val Ala Ala Gly Thr Gly Ile Ser Asn Tyr Ile Asn Thr Ile
```

-continued

```
            50                  55                  60
Pro Val Glu Glu Gln Pro Glu Tyr Pro Gly Asn Leu Glu Leu Glu Arg
65                  70                  75                  80

Arg Ile Arg Ser Ala Ile Arg Trp Asn Ala Ile Met Thr Val Leu Arg
                85                  90                  95

Ala Ser Lys Lys Asp Leu Glu Leu Gly Gly His Met Ala Ser Phe Gln
            100                 105                 110

Ser Ser Ala Thr Ile Tyr Asp Val Cys Phe Asn His Phe Phe Arg Ala
            115                 120                 125

Arg Asn Glu Gln Asp Gly Gly Asp Leu Val Tyr Phe Gln Gly His Ile
130                 135                 140

Ser Pro Gly Val Tyr Ala Arg Ala Phe Leu Glu Gly Arg Leu Thr Gln
145                 150                 155                 160

Glu Gln Leu Asp Asn Phe Arg Gln Glu Val His Gly Asn Gly Leu Ser
                165                 170                 175

Ser Tyr Pro His Pro Lys Leu Met Pro Glu Phe Trp Gln Phe Pro Thr
            180                 185                 190

Val Ser Met Gly Leu Gly Pro Ile Gly Ala Ile Tyr Gln Ala Lys Phe
            195                 200                 205

Leu Lys Tyr Leu Glu His Arg Gly Leu Lys Asp Thr Ser Lys Gln Thr
210                 215                 220

Val Tyr Ala Phe Leu Gly Asp Gly Glu Met Asp Glu Pro Glu Ser Lys
225                 230                 235                 240

Gly Ala Ile Thr Ile Ala Thr Arg Glu Lys Leu Asp Asn Leu Val Phe
                245                 250                 255

Val Ile Asn Cys Asn Leu Gln Arg Leu Asp Gly Pro Val Thr Gly Asn
            260                 265                 270

Gly Lys Ile Ile Asn Glu Leu Glu Gly Ile Phe Glu Gly Ala Gly Trp
            275                 280                 285

Asn Val Ile Lys Val Met Trp Gly Ser Arg Trp Asp Glu Leu Leu Arg
290                 295                 300

Lys Asp Thr Ser Gly Lys Leu Ile Gln Leu Met Asn Glu Thr Val Asp
305                 310                 315                 320

Gly Asp Tyr Gln Thr Phe Lys Ser Lys Asp Gly Ala Tyr Val Arg Glu
                325                 330                 335

His Phe Phe Gly Lys Tyr Pro Glu Thr Ala Ala Leu Val Ala Asp Trp
            340                 345                 350

Thr Asp Glu Gln Ile Trp Ala Leu Asn Arg Gly Gly His Asp Pro Lys
            355                 360                 365

Lys Ile Tyr Ala Ala Phe Lys Lys Ala Gln Glu Thr Lys Gly Lys Ala
370                 375                 380

Thr Val Ile Leu Ala His Thr Ile Lys Gly Tyr Gly Met Gly Asp Ala
385                 390                 395                 400

Ala Glu Gly Lys Asn Ile Ala His Gln Val Lys Lys Met Asn Met Asp
                405                 410                 415

Gly Val Arg His Ile Arg Asp Arg Phe Asn Val Pro Val Ser Asp Ala
            420                 425                 430

Asp Ile Glu Lys Leu Pro Tyr Ile Thr Phe Pro Glu Gly Ser Glu Glu
            435                 440                 445

His Thr Tyr Leu His Ala Gln Arg Gln Lys Leu His Gly Tyr Leu Pro
450                 455                 460

Ser Arg Gln Pro Asn Phe Thr Glu Lys Leu Glu Leu Pro Ser Leu Gln
465                 470                 475                 480
```

```
Asp Phe Gly Ala Leu Leu Glu Glu Gln Ser Lys Glu Ile Ser Thr Thr
            485                 490                 495

Ile Ala Phe Val Arg Ala Leu Asn Val Met Leu Lys Asn Lys Ser Ile
            500                 505                 510

Lys Asp Arg Leu Val Pro Ile Ala Asp Glu Ala Arg Thr Phe Gly
            515                 520                 525

Met Glu Gly Leu Phe Arg Gln Ile Gly Ile Tyr Ser Pro Asn Gly Gln
    530                 535                 540

Gln Tyr Thr Pro Gln Asp Arg Glu Gln Val Ala Tyr Lys Glu Asp
545                 550                 555                 560

Glu Lys Gly Gln Ile Leu Gln Glu Gly Ile Asn Glu Leu Gly Ala Gly
                565                 570                 575

Cys Ser Trp Leu Ala Ala Thr Ser Tyr Ser Thr Asn Asn Leu Pro
                580                 585                 590

Met Ile Pro Phe Tyr Ile Tyr Tyr Ser Met Phe Gly Phe Gln Arg Ile
            595                 600                 605

Gly Asp Leu Cys Trp Ala Ala Gly Asp Gln Gln Ala Arg Gly Phe Leu
            610                 615                 620

Ile Gly Gly Thr Ser Gly Arg Thr Thr Leu Asn Gly Glu Gly Leu Gln
625                 630                 635                 640

His Glu Asp Gly His Ser His Ile Gln Ser Leu Thr Ile Pro Asn Cys
                645                 650                 655

Ile Ser Tyr Asp Pro Ala Tyr Ala Tyr Glu Val Ala Val Ile Met His
                660                 665                 670

Asp Gly Leu Glu Arg Met Tyr Gly Glu Lys Gln Glu Asn Val Tyr Tyr
            675                 680                 685

Tyr Ile Thr Thr Leu Asn Glu Asn Tyr His Met Pro Ala Met Pro Glu
            690                 695                 700

Gly Ala Glu Glu Gly Ile Arg Lys Gly Ile Tyr Lys Leu Glu Thr Ile
705                 710                 715                 720

Glu Gly Ser Lys Gly Lys Val Gln Leu Leu Gly Ser Gly Ser Ile Leu
                725                 730                 735

Arg His Val Arg Glu Ala Ala Glu Ile Leu Ala Lys Asp Tyr Gly Val
                740                 745                 750

Gly Ser Asp Val Tyr Ser Val Thr Ser Phe Thr Glu Leu Ala Arg Asp
            755                 760                 765

Gly Gln Asp Cys Glu Arg Trp Asn Met Leu His Pro Leu Glu Thr Pro
            770                 775                 780

Arg Val Pro Tyr Ile Ala Gln Val Met Asn Asp Ala Pro Ala Val Ala
785                 790                 795                 800

Ser Thr Asp Tyr Met Lys Leu Phe Ala Glu Gln Val Arg Thr Tyr Val
                805                 810                 815

Pro Ala Asp Asp Tyr Arg Val Leu Gly Thr Asp Gly Phe Gly Arg Ser
            820                 825                 830

Asp Ser Arg Glu Asn Leu Arg His His Phe Glu Val Asp Ala Ser Tyr
            835                 840                 845

Val Val Val Ala Ala Leu Gly Glu Leu Ala Lys Arg Gly Glu Ile Asp
    850                 855                 860

Lys Lys Val Val Ala Asp Ala Ile Ala Lys Phe Asn Ile Asp Ala Asp
865                 870                 875                 880

Lys Val Asn Pro Arg Leu Ala
                885
```

<210> SEQ ID NO 48
<211> LENGTH: 1893
<212> TYPE: DNA
<213> ORGANISM: Escherichia coli
<220> FEATURE:
<221> NAME/KEY: CDS
<222> LOCATION: (1)..(1893)

<400> SEQUENCE: 48

| | | | | | | | | | | | | | | | | |
|---|---|---|---|---|---|---|---|---|---|---|---|---|---|---|---|---|
| atg | gct | atc | gaa | atc | aaa | gta | ccg | gac | atc | ggg | gct | gat | gaa | gtt | gaa | 48 |
| Met | Ala | Ile | Glu | Ile | Lys | Val | Pro | Asp | Ile | Gly | Ala | Asp | Glu | Val | Glu | |
| 1 | | | | 5 | | | | | 10 | | | | | 15 | | |
| atc | acc | gag | atc | ctg | gtc | aaa | gtg | ggc | gac | aaa | gtt | gaa | gcc | gaa | cag | 96 |
| Ile | Thr | Glu | Ile | Leu | Val | Lys | Val | Gly | Asp | Lys | Val | Glu | Ala | Glu | Gln | |
| | | | 20 | | | | | 25 | | | | | 30 | | | |
| tcg | ctg | atc | acc | gta | gaa | ggc | gac | aaa | gcc | tct | atg | gaa | gtt | ccg | tct | 144 |
| Ser | Leu | Ile | Thr | Val | Glu | Gly | Asp | Lys | Ala | Ser | Met | Glu | Val | Pro | Ser | |
| | | 35 | | | | | 40 | | | | | 45 | | | | |
| ccg | cag | gcg | ggt | atc | gtt | aaa | gag | atc | aaa | gtc | tct | gtt | ggc | gat | aaa | 192 |
| Pro | Gln | Ala | Gly | Ile | Val | Lys | Glu | Ile | Lys | Val | Ser | Val | Gly | Asp | Lys | |
| | 50 | | | | | 55 | | | | | 60 | | | | | |
| acc | cag | acc | ggc | gca | ctg | att | atg | att | ttc | gat | tcc | gcc | gac | ggt | gca | 240 |
| Thr | Gln | Thr | Gly | Ala | Leu | Ile | Met | Ile | Phe | Asp | Ser | Ala | Asp | Gly | Ala | |
| 65 | | | | | 70 | | | | | 75 | | | | | 80 | |
| gca | gac | gct | gca | cct | gct | cag | gca | gaa | gag | aag | aaa | gaa | gca | gct | ccg | 288 |
| Ala | Asp | Ala | Ala | Pro | Ala | Gln | Ala | Glu | Glu | Lys | Lys | Glu | Ala | Ala | Pro | |
| | | | 85 | | | | | 90 | | | | | 95 | | | |
| gca | gca | gca | cca | gcg | gct | gcg | gcg | gca | aaa | gac | gtt | aac | gtt | ccg | gat | 336 |
| Ala | Ala | Ala | Pro | Ala | Ala | Ala | Ala | Ala | Lys | Asp | Val | Asn | Val | Pro | Asp | |
| | | 100 | | | | | 105 | | | | | 110 | | | | |
| atc | ggc | agc | gac | gaa | gtt | gaa | gtg | acc | gaa | atc | ctg | gtg | aaa | gtt | ggc | 384 |
| Ile | Gly | Ser | Asp | Glu | Val | Glu | Val | Thr | Glu | Ile | Leu | Val | Lys | Val | Gly | |
| | 115 | | | | | 120 | | | | | 125 | | | | | |
| gat | aaa | gtt | gaa | gct | gaa | cag | tcg | ctg | atc | acc | gta | gaa | ggc | gac | aag | 432 |
| Asp | Lys | Val | Glu | Ala | Glu | Gln | Ser | Leu | Ile | Thr | Val | Glu | Gly | Asp | Lys | |
| 130 | | | | | 135 | | | | | 140 | | | | | | |
| gct | tct | atg | gaa | gtt | ccg | gct | ccg | ttt | gct | ggc | acc | gtg | aaa | gag | atc | 480 |
| Ala | Ser | Met | Glu | Val | Pro | Ala | Pro | Phe | Ala | Gly | Thr | Val | Lys | Glu | Ile | |
| 145 | | | | | 150 | | | | | 155 | | | | | 160 | |
| aaa | gtg | aac | gtg | ggt | gac | aaa | gtg | tct | acc | ggc | tcg | ctg | att | atg | gtc | 528 |
| Lys | Val | Asn | Val | Gly | Asp | Lys | Val | Ser | Thr | Gly | Ser | Leu | Ile | Met | Val | |
| | | | 165 | | | | | 170 | | | | | 175 | | | |
| ttc | gaa | gtc | gcg | ggt | gaa | gca | ggc | gcg | gca | gct | ccg | gcc | gct | aaa | cag | 576 |
| Phe | Glu | Val | Ala | Gly | Glu | Ala | Gly | Ala | Ala | Ala | Pro | Ala | Ala | Lys | Gln | |
| | | | 180 | | | | | 185 | | | | | 190 | | | |
| gaa | gca | gct | ccg | gca | gcg | gcc | cct | gca | cca | gcg | gct | ggc | gtg | aaa | gaa | 624 |
| Glu | Ala | Ala | Pro | Ala | Ala | Ala | Pro | Ala | Pro | Ala | Ala | Gly | Val | Lys | Glu | |
| | | 195 | | | | | 200 | | | | | 205 | | | | |
| gtt | aac | gtt | ccg | gat | atc | ggc | ggt | gac | gaa | gtt | gaa | gtg | act | gaa | gtg | 672 |
| Val | Asn | Val | Pro | Asp | Ile | Gly | Gly | Asp | Glu | Val | Glu | Val | Thr | Glu | Val | |
| | 210 | | | | | 215 | | | | | 220 | | | | | |
| atg | gtg | aaa | gtg | ggc | gac | aaa | gtt | gcc | gct | gaa | cag | tca | ctg | atc | acc | 720 |
| Met | Val | Lys | Val | Gly | Asp | Lys | Val | Ala | Ala | Glu | Gln | Ser | Leu | Ile | Thr | |
| 225 | | | | | 230 | | | | | 235 | | | | | 240 | |
| gta | gaa | ggc | gac | aaa | gct | tct | atg | gaa | gtt | ccg | gcg | ccg | ttt | gca | ggc | 768 |
| Val | Glu | Gly | Asp | Lys | Ala | Ser | Met | Glu | Val | Pro | Ala | Pro | Phe | Ala | Gly | |
| | | | 245 | | | | | 250 | | | | | 255 | | | |
| gtc | gtg | aag | gaa | ctg | aaa | gtc | aac | gtt | ggc | gat | aaa | gtg | aaa | act | ggc | 816 |
| Val | Val | Lys | Glu | Leu | Lys | Val | Asn | Val | Gly | Asp | Lys | Val | Lys | Thr | Gly | |
| | | | 260 | | | | | 265 | | | | | 270 | | | |

-continued

| | | |
|---|---|---|
| tcg ctg att atg atc ttc gaa gtt gaa ggc gca gcg cct gcg gca gct<br>Ser Leu Ile Met Ile Phe Glu Val Glu Gly Ala Ala Pro Ala Ala Ala<br>          275                  280                    285 | | 864 |
| cct gcg aaa cag gaa gcg gca gcg ccg gca ccg gca aaa gct gaa<br>Pro Ala Lys Gln Glu Ala Ala Ala Pro Ala Pro Ala Lys Ala Glu<br> 290                      295                    300 | | 912 |
| gcc ccg gca gca gca cca gct gcg aaa gcg gaa ggc aaa tct gaa ttt<br>Ala Pro Ala Ala Ala Pro Ala Ala Lys Ala Glu Gly Lys Ser Glu Phe<br>305                    310                    315                  320 | | 960 |
| gct gaa aac gac gct tat gtt cac gcg act ccg ctg atc cgc cgt ctg<br>Ala Glu Asn Asp Ala Tyr Val His Ala Thr Pro Leu Ile Arg Arg Leu<br>                    325                    330                  335 | | 1008 |
| gca cgc gag ttt ggt gtt aac ctt gcg aaa gtg aag ggc act ggc cgt<br>Ala Arg Glu Phe Gly Val Asn Leu Ala Lys Val Lys Gly Thr Gly Arg<br>             340                    345                  350 | | 1056 |
| aaa ggt cgt atc ctg cgc gaa gac gtt cag gct tac gtg aaa gaa gct<br>Lys Gly Arg Ile Leu Arg Glu Asp Val Gln Ala Tyr Val Lys Glu Ala<br>          355                    360                    365 | | 1104 |
| atc aaa cgt gca gaa gca gct ccg gca gcg act ggc ggt ggt atc cct<br>Ile Lys Arg Ala Glu Ala Ala Pro Ala Ala Thr Gly Gly Gly Ile Pro<br>370                    375                    380 | | 1152 |
| ggc atg ctg ccg tgg ccg aag gtg gac ttc agc aag ttt ggt gaa atc<br>Gly Met Leu Pro Trp Pro Lys Val Asp Phe Ser Lys Phe Gly Glu Ile<br>385                    390                    395                  400 | | 1200 |
| gaa gaa gtg gaa ctg ggc cgc atc cag aaa atc tct ggt gcg aac ctg<br>Glu Glu Val Glu Leu Gly Arg Ile Gln Lys Ile Ser Gly Ala Asn Leu<br>                    405                    410                  415 | | 1248 |
| agc cgt aac tgg gta atg atc ccg cat gtt act cac ttc gac aaa acc<br>Ser Arg Asn Trp Val Met Ile Pro His Val Thr His Phe Asp Lys Thr<br>             420                    425                  430 | | 1296 |
| gat atc acc gag ttg gaa gcg ttc cgt aaa cag cag aac gaa gaa gcg<br>Asp Ile Thr Glu Leu Glu Ala Phe Arg Lys Gln Gln Asn Glu Glu Ala<br>          435                    440                    445 | | 1344 |
| gcg aaa cgt aag ctg gat gtg aag atc acc ccg gtt gtc ttc atc atg<br>Ala Lys Arg Lys Leu Asp Val Lys Ile Thr Pro Val Val Phe Ile Met<br>450                    455                    460 | | 1392 |
| aaa gcc gtt gct gca gct ctt gag cag atg cct cgc ttc aat agt tcg<br>Lys Ala Val Ala Ala Ala Leu Glu Gln Met Pro Arg Phe Asn Ser Ser<br>465                    470                    475                  480 | | 1440 |
| ctg tcg gaa gac ggt cag cgt ctg acc ctg aag aaa tac atc aac atc<br>Leu Ser Glu Asp Gly Gln Arg Leu Thr Leu Lys Lys Tyr Ile Asn Ile<br>                    485                    490                  495 | | 1488 |
| ggt gtg gcg gtg gat acc ccg aac ggt ctg gtt gtt ccg gta ttc aaa<br>Gly Val Ala Val Asp Thr Pro Asn Gly Leu Val Val Pro Val Phe Lys<br>             500                    505                  510 | | 1536 |
| gac gtc aac aag aaa ggc atc atc gag ctg tct cgc gag ctg atg act<br>Asp Val Asn Lys Lys Gly Ile Ile Glu Leu Ser Arg Glu Leu Met Thr<br>          515                    520                  525 | | 1584 |
| att tct aag aaa gcg cgt gac ggt aag ctg act gcg ggc gaa atg cag<br>Ile Ser Lys Lys Ala Arg Asp Gly Lys Leu Thr Ala Gly Glu Met Gln<br>530                    535                    540 | | 1632 |
| ggc ggt tgc ttc acc atc tcc agc atc ggc ggc ctg ggt act acc cac<br>Gly Gly Cys Phe Thr Ile Ser Ser Ile Gly Gly Leu Gly Thr Thr His<br>545                    550                    555                  560 | | 1680 |
| ttc gcg ccg att gtg aac gcg ccg gaa gtg gct atc ctc ggc gtt tcc<br>Phe Ala Pro Ile Val Asn Ala Pro Glu Val Ala Ile Leu Gly Val Ser<br>                    565                    570                  575 | | 1728 |
| aag tcc gcg atg gag ccg gtg tgg aat ggt aaa gag ttc gtg ccg cgt<br>Lys Ser Ala Met Glu Pro Val Trp Asn Gly Lys Glu Phe Val Pro Arg<br>             580                    585                  590 | | 1776 |

```
ctg atg ctg ccg att tct ctc tcc ttc gac cac cgc gtg atc gac ggt      1824
Leu Met Leu Pro Ile Ser Leu Ser Phe Asp His Arg Val Ile Asp Gly
        595                 600                 605 gct gat ggt gcc cgt ttc att acc atc att aac aac acg ctg tct gac      1872
Ala Asp Gly Ala Arg Phe Ile Thr Ile Ile Asn Asn Thr Leu Ser Asp
    610                 615                 620 att cgc cgt ctg gtg atg taa                                          1893
Ile Arg Arg Leu Val Met
625             630

<210> SEQ ID NO 49
<211> LENGTH: 630
<212> TYPE: PRT
<213> ORGANISM: Escherichia coli

<400> SEQUENCE: 49
```

Met Ala Ile Glu Ile Lys Val Pro Asp Ile Gly Ala Asp Glu Val Glu
1               5                   10                  15

Ile Thr Glu Ile Leu Val Lys Val Gly Asp Lys Val Glu Ala Glu Gln
            20                  25                  30

Ser Leu Ile Thr Val Glu Gly Asp Lys Ala Ser Met Glu Val Pro Ser
        35                  40                  45

Pro Gln Ala Gly Ile Val Lys Glu Ile Lys Val Ser Val Gly Asp Lys
    50                  55                  60

Thr Gln Thr Gly Ala Leu Ile Met Ile Phe Asp Ser Ala Asp Gly Ala
65                  70                  75                  80

Ala Asp Ala Ala Pro Ala Gln Ala Glu Glu Lys Lys Glu Ala Ala Pro
                85                  90                  95

Ala Ala Ala Pro Ala Ala Ala Ala Lys Asp Val Asn Val Pro Asp
            100                 105                 110

Ile Gly Ser Asp Glu Val Glu Val Thr Glu Ile Leu Val Lys Val Gly
        115                 120                 125

Asp Lys Val Glu Ala Glu Gln Ser Leu Ile Thr Val Glu Gly Asp Lys
    130                 135                 140

Ala Ser Met Glu Val Pro Ala Pro Phe Ala Gly Thr Val Lys Glu Ile
145                 150                 155                 160

Lys Val Asn Val Gly Asp Lys Val Ser Thr Gly Ser Leu Ile Met Val
                165                 170                 175

Phe Glu Val Ala Gly Glu Ala Gly Ala Ala Pro Ala Ala Lys Gln
            180                 185                 190

Glu Ala Ala Pro Ala Ala Ala Pro Ala Pro Ala Ala Gly Val Lys Glu
    195                 200                 205

Val Asn Val Pro Asp Ile Gly Gly Asp Glu Val Glu Val Thr Glu Val
    210                 215                 220

Met Val Lys Val Gly Asp Lys Val Ala Ala Glu Gln Ser Leu Ile Thr
225                 230                 235                 240

Val Glu Gly Asp Lys Ala Ser Met Glu Val Pro Ala Pro Phe Ala Gly
                245                 250                 255

Val Val Lys Glu Leu Lys Val Asn Val Gly Asp Lys Val Lys Thr Gly
            260                 265                 270

Ser Leu Ile Met Ile Phe Glu Val Glu Gly Ala Ala Pro Ala Ala Ala
        275                 280                 285

Pro Ala Lys Gln Glu Ala Ala Pro Ala Pro Ala Ala Lys Ala Glu
    290                 295                 300

Ala Pro Ala Ala Ala Pro Ala Ala Lys Ala Glu Gly Lys Ser Glu Phe

```
                305                 310                 315                 320
Ala Glu Asn Asp Ala Tyr Val His Ala Thr Pro Leu Ile Arg Arg Leu
                325                 330                 335

Ala Arg Glu Phe Gly Val Asn Leu Ala Lys Val Lys Gly Thr Gly Arg
            340                 345                 350

Lys Gly Arg Ile Leu Arg Glu Asp Val Gln Ala Tyr Val Lys Glu Ala
        355                 360                 365

Ile Lys Arg Ala Glu Ala Ala Pro Ala Ala Thr Gly Gly Gly Ile Pro
    370                 375                 380

Gly Met Leu Pro Trp Pro Lys Val Asp Phe Ser Lys Phe Gly Glu Ile
385                 390                 395                 400

Glu Glu Val Glu Leu Gly Arg Ile Gln Lys Ile Ser Gly Ala Asn Leu
                405                 410                 415

Ser Arg Asn Trp Val Met Ile Pro His Val Thr His Phe Asp Lys Thr
            420                 425                 430

Asp Ile Thr Glu Leu Glu Ala Phe Arg Lys Gln Gln Asn Glu Glu Ala
        435                 440                 445

Ala Lys Arg Lys Leu Asp Val Lys Ile Thr Pro Val Val Phe Ile Met
    450                 455                 460

Lys Ala Val Ala Ala Leu Glu Gln Met Pro Arg Phe Asn Ser Ser
465                 470                 475                 480

Leu Ser Glu Asp Gly Gln Arg Leu Thr Leu Lys Lys Tyr Ile Asn Ile
                485                 490                 495

Gly Val Ala Val Asp Thr Pro Asn Gly Leu Val Val Pro Val Phe Lys
            500                 505                 510

Asp Val Asn Lys Lys Gly Ile Ile Glu Leu Ser Arg Glu Leu Met Thr
        515                 520                 525

Ile Ser Lys Lys Ala Arg Asp Gly Lys Leu Thr Ala Gly Glu Met Gln
    530                 535                 540

Gly Gly Cys Phe Thr Ile Ser Ser Ile Gly Gly Leu Gly Thr Thr His
545                 550                 555                 560

Phe Ala Pro Ile Val Asn Ala Pro Glu Val Ala Ile Leu Gly Val Ser
                565                 570                 575

Lys Ser Ala Met Glu Pro Val Trp Asn Gly Lys Glu Phe Val Pro Arg
            580                 585                 590

Leu Met Leu Pro Ile Ser Leu Ser Phe Asp His Arg Val Ile Asp Gly
        595                 600                 605

Ala Asp Gly Ala Arg Phe Ile Thr Ile Ile Asn Asn Thr Leu Ser Asp
    610                 615                 620

Ile Arg Arg Leu Val Met
625                 630

<210> SEQ ID NO 50
<211> LENGTH: 1425
<212> TYPE: DNA
<213> ORGANISM: Escherichia coli
<220> FEATURE:
<221> NAME/KEY: CDS
<222> LOCATION: (1)..(1425)

<400> SEQUENCE: 50 atg agt act gaa atc aaa act cag gtc gtg gta ctt ggg gca ggc ccc      48
Met Ser Thr Glu Ile Lys Thr Gln Val Val Val Leu Gly Ala Gly Pro
1               5                   10                  15 gca ggt tac tcc gct gcc ttc cgt tgc gct gat tta ggt ctg gaa acc      96
Ala Gly Tyr Ser Ala Ala Phe Arg Cys Ala Asp Leu Gly Leu Glu Thr
```

-continued

|  | 20 | 25 | 30 |  |
|---|---|---|---|---|
| gta atc gta gaa cgt tac aac acc ctt ggc ggt gtt tgc ctg aac gtc<br>Val Ile Val Glu Arg Tyr Asn Thr Leu Gly Gly Val Cys Leu Asn Val<br>35                      40                        45 | | | | 144 |
| ggc tgt atc cct tct aaa gca ctg ctg cac gta gca aaa gtt atc gaa<br>Gly Cys Ile Pro Ser Lys Ala Leu Leu His Val Ala Lys Val Ile Glu<br>50                      55                        60 | | | | 192 |
| gaa gcc aaa gcg ctg gct gaa cac ggt atc gtc ttc ggc gaa ccg aaa<br>Glu Ala Lys Ala Leu Ala Glu His Gly Ile Val Phe Gly Glu Pro Lys<br>65                      70                        75                        80 | | | | 240 |
| acc gat atc gac aag att cgt acc tgg aaa gag aaa gtg atc aat cag<br>Thr Asp Ile Asp Lys Ile Arg Thr Trp Lys Glu Lys Val Ile Asn Gln<br>                      85                        90                        95 | | | | 288 |
| ctg acc ggt ggt ctg gct ggt atg gca aaa ggc cgc aaa gtc aaa gtg<br>Leu Thr Gly Gly Leu Ala Gly Met Ala Lys Gly Arg Lys Val Lys Val<br>100                      105                      110 | | | | 336 |
| gtc aac ggt ctg ggt aaa ttc acc ggg gct aac acc ctg gaa gtt gaa<br>Val Asn Gly Leu Gly Lys Phe Thr Gly Ala Asn Thr Leu Glu Val Glu<br>115                      120                      125 | | | | 384 |
| ggt gag aac ggc aaa acc gtg atc aac ttc gac aac gcg atc att gca<br>Gly Glu Asn Gly Lys Thr Val Ile Asn Phe Asp Asn Ala Ile Ile Ala<br>130                      135                      140 | | | | 432 |
| gcg ggt tct cgc ccg atc caa ctg ccg ttt att ccg cat gaa gat ccg<br>Ala Gly Ser Arg Pro Ile Gln Leu Pro Phe Ile Pro His Glu Asp Pro<br>145                      150                      155                        160 | | | | 480 |
| cgt atc tgg gac tcc act gac gcg ctg gaa ctg aaa gaa gta cca gaa<br>Arg Ile Trp Asp Ser Thr Asp Ala Leu Glu Leu Lys Glu Val Pro Glu<br>                           165                      170                      175 | | | | 528 |
| cgc ctg ctg gta atg ggt ggc ggt atc atc ggt ctg gaa atg ggc acc<br>Arg Leu Leu Val Met Gly Gly Gly Ile Ile Gly Leu Glu Met Gly Thr<br>180                      185                      190 | | | | 576 |
| gtt tac cac gcg ctg ggt tca cag att gac gtg gtt gaa atg ttc gac<br>Val Tyr His Ala Leu Gly Ser Gln Ile Asp Val Val Glu Met Phe Asp<br>195                      200                      205 | | | | 624 |
| cag gtt atc ccg gca gct gac aaa gac atc gtt aaa gtc ttc acc aag<br>Gln Val Ile Pro Ala Ala Asp Lys Asp Ile Val Lys Val Phe Thr Lys<br>210                      215                      220 | | | | 672 |
| cgt atc agc aag aaa ttc aac ctg atg ctg gaa acc aaa gtt acc gcc<br>Arg Ile Ser Lys Lys Phe Asn Leu Met Leu Glu Thr Lys Val Thr Ala<br>225                      230                      235                        240 | | | | 720 |
| gtt gaa gcg aaa gaa gac ggc att tat gtg acg atg gaa ggc aaa aaa<br>Val Glu Ala Lys Glu Asp Gly Ile Tyr Val Thr Met Glu Gly Lys Lys<br>                           245                      250                      255 | | | | 768 |
| gca ccc gct gaa ccg cag cgt tac gac gcc gtg ctg gta gcg att ggt<br>Ala Pro Ala Glu Pro Gln Arg Tyr Asp Ala Val Leu Val Ala Ile Gly<br>260                      265                      270 | | | | 816 |
| cgt gtg ccg aac ggt aaa aac ctc gac gca ggc aaa gca ggc gtg gaa<br>Arg Val Pro Asn Gly Lys Asn Leu Asp Ala Gly Lys Ala Gly Val Glu<br>275                      280                      285 | | | | 864 |
| gtt gac gac cgt ggt ttc atc cgc gtt gac aaa cag ctg cgt acc aac<br>Val Asp Asp Arg Gly Phe Ile Arg Val Asp Lys Gln Leu Arg Thr Asn<br>290                      295                      300 | | | | 912 |
| gta ccg cac atc ttt gct atc ggc gat atc gtc ggt caa ccg atg ctg<br>Val Pro His Ile Phe Ala Ile Gly Asp Ile Val Gly Gln Pro Met Leu<br>305                      310                      315                        320 | | | | 960 |
| gca cac aaa ggt gtt cac gaa ggt cac gtt gcc gct gaa gtt atc gcc<br>Ala His Lys Gly Val His Glu Gly His Val Ala Ala Glu Val Ile Ala<br>                         325                      330                      335 | | | | 1008 |
| ggt aag aaa cac tac ttc gat ccg aaa gtt atc ccg tcc atc gcc tat | | | | 1056 |

```
                                                                  -continued Gly Lys Lys His Tyr Phe Asp Pro Lys Val Ile Pro Ser Ile Ala Tyr
            340                 345                 350 acc gaa cca gaa gtt gca tgg gtg ggt ctg act gag aaa gaa gcg aaa        1104
Thr Glu Pro Glu Val Ala Trp Val Gly Leu Thr Glu Lys Glu Ala Lys
        355                 360                 365 gag aaa ggc atc agc tat gaa acc gcc acc ttc ccg tgg gct gct tct        1152
Glu Lys Gly Ile Ser Tyr Glu Thr Ala Thr Phe Pro Trp Ala Ala Ser
    370                 375                 380 ggt cgt gct atc gct tcc gac tgc gca gac ggt atg acc aag ctg att        1200
Gly Arg Ala Ile Ala Ser Asp Cys Ala Asp Gly Met Thr Lys Leu Ile
385                 390                 395                 400 ttc gac aaa gaa tct cac cgt gtg atc ggt ggt gcg att gtc ggt act        1248
Phe Asp Lys Glu Ser His Arg Val Ile Gly Gly Ala Ile Val Gly Thr
                405                 410                 415 aac ggc ggc gag ctg ctg ggt gaa atc ggc ctg gca atc gaa atg ggt        1296
Asn Gly Gly Glu Leu Leu Gly Glu Ile Gly Leu Ala Ile Glu Met Gly
            420                 425                 430 tgt gat gct gaa gac atc gca ctg acc atc cac gcg cac ccg act ctg        1344
Cys Asp Ala Glu Asp Ile Ala Leu Thr Ile His Ala His Pro Thr Leu
        435                 440                 445 cac gag tct gtg ggc ctg gcg gca gaa gtg ttc gaa ggt agc att acc        1392
His Glu Ser Val Gly Leu Ala Ala Glu Val Phe Glu Gly Ser Ile Thr
    450                 455                 460 gac ctg ccg aac ccg aaa gcg aag aag aag taa                            1425
Asp Leu Pro Asn Pro Lys Ala Lys Lys Lys
465                 470

<210> SEQ ID NO 51
<211> LENGTH: 474
<212> TYPE: PRT
<213> ORGANISM: Escherichia coli

<400> SEQUENCE: 51

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190
```

Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
450                 455                 460

Asp Leu Pro Asn Pro Lys Ala Lys Lys Lys
465                 470

<210> SEQ ID NO 52
<211> LENGTH: 1698
<212> TYPE: DNA
<213> ORGANISM: Escherichia coli
<220> FEATURE:
<221> NAME/KEY: CDS
<222> LOCATION: (1)..(1698)

<400> SEQUENCE: 52

```
atg gaa cca aaa aca aaa aaa cag cgt tcg ctt tat atc cct tac gct      48
Met Glu Pro Lys Thr Lys Lys Gln Arg Ser Leu Tyr Ile Pro Tyr Ala
1               5                   10                  15 ggc cct gta ctg ctg gaa ttt ccg ttg ttg aat aaa ggc agt gcc ttc      96
Gly Pro Val Leu Leu Glu Phe Pro Leu Leu Asn Lys Gly Ser Ala Phe
                20                  25                  30 agc atg gaa gaa cgc cgt aac ttc aac ctg ctg ggg tta ctg ccg gaa     144
Ser Met Glu Glu Arg Arg Asn Phe Asn Leu Leu Gly Leu Leu Pro Glu
            35                  40                  45 gtg gtc gaa acc atc gaa gaa caa gcg gaa cga gca tgg atc cag tat     192
Val Val Glu Thr Ile Glu Glu Gln Ala Glu Arg Ala Trp Ile Gln Tyr
```

-continued

```
            50                  55                  60
cag gga ttc aaa acc gaa atc gac aaa cac atc tac ctg cgt aac atc      240
Gln Gly Phe Lys Thr Glu Ile Asp Lys His Ile Tyr Leu Arg Asn Ile
 65                  70                  75                  80 cag gac act aac gaa acc ctc ttc tac cgt ctg gta aac aat cat ctt      288
Gln Asp Thr Asn Glu Thr Leu Phe Tyr Arg Leu Val Asn Asn His Leu
                 85                  90                  95 gat gag atg atg cct gtt att tat acc cca acc gtc ggc gca gcc tgt      336
Asp Glu Met Met Pro Val Ile Tyr Thr Pro Thr Val Gly Ala Ala Cys
            100                 105                 110 gag cgt ttt tct gag atc tac cgc cgt tca cgc ggc gtg ttt atc tct      384
Glu Arg Phe Ser Glu Ile Tyr Arg Arg Ser Arg Gly Val Phe Ile Ser
        115                 120                 125 tac cag aac cgg cac aat atg gac gat att ctg caa aac gtg ccg aac      432
Tyr Gln Asn Arg His Asn Met Asp Asp Ile Leu Gln Asn Val Pro Asn
    130                 135                 140 cat aat att aaa gtg att gtg gtg act gac ggt gaa cgc att ctg ggg      480
His Asn Ile Lys Val Ile Val Val Thr Asp Gly Glu Arg Ile Leu Gly
145                 150                 155                 160 ctt ggt gac cag ggc atc ggc ggg atg ggc att ccg atc ggt aaa ctg      528
Leu Gly Asp Gln Gly Ile Gly Gly Met Gly Ile Pro Ile Gly Lys Leu
                165                 170                 175 tcg ctc tat acc gcc tgt ggc ggc atc agc ccg gcg tat acc ctt ccg      576
Ser Leu Tyr Thr Ala Cys Gly Gly Ile Ser Pro Ala Tyr Thr Leu Pro
            180                 185                 190 gtg gtg ctg gat gtc gga acg aac aac caa cag ctg ctt aac gat ccg      624
Val Val Leu Asp Val Gly Thr Asn Asn Gln Gln Leu Leu Asn Asp Pro
        195                 200                 205 ctg tat atg ggc tgg cgt aat ccg cgt atc act gac gac gaa tac tat      672
Leu Tyr Met Gly Trp Arg Asn Pro Arg Ile Thr Asp Asp Glu Tyr Tyr
    210                 215                 220 gaa ttc gtt gat gaa ttt atc cag gct gtg aaa caa cgc tgg cca gac      720
Glu Phe Val Asp Glu Phe Ile Gln Ala Val Lys Gln Arg Trp Pro Asp
225                 230                 235                 240 gtg ctg ttg cag ttt gaa gac ttt gct caa aaa aat gcg atg ccg tta      768
Val Leu Leu Gln Phe Glu Asp Phe Ala Gln Lys Asn Ala Met Pro Leu
                245                 250                 255 ctt aac cgc tat cgc aat gaa att tgt tct ttt aac gat gac att cag      816
Leu Asn Arg Tyr Arg Asn Glu Ile Cys Ser Phe Asn Asp Asp Ile Gln
            260                 265                 270 ggc act gcg gcg gta aca gtc ggc aca ctg atc gca gca agc cgc gcg      864
Gly Thr Ala Ala Val Thr Val Gly Thr Leu Ile Ala Ala Ser Arg Ala
        275                 280                 285 gca ggt ggt cag tta agc gag aaa aaa atc gtc ttc ctt ggc gca ggt      912
Ala Gly Gly Gln Leu Ser Glu Lys Lys Ile Val Phe Leu Gly Ala Gly
    290                 295                 300 tca gcg gga tgc ggc att gcc gaa atg atc atc tcc cag acc cag cgc      960
Ser Ala Gly Cys Gly Ile Ala Glu Met Ile Ile Ser Gln Thr Gln Arg
305                 310                 315                 320 gaa gga tta agc gag gaa gcg gcg cgg cag aaa gtc ttt atg gtc gat     1008
Glu Gly Leu Ser Glu Glu Ala Ala Arg Gln Lys Val Phe Met Val Asp
                325                 330                 335 cgc ttt ggc ttg ctg act gac aag atg ccg aac ctg ctg cct ttc cag     1056
Arg Phe Gly Leu Leu Thr Asp Lys Met Pro Asn Leu Leu Pro Phe Gln
            340                 345                 350 acc aaa ctg gtg cag aag cgc gaa aac ctc agt gac tgg gat acc gac     1104
Thr Lys Leu Val Gln Lys Arg Glu Asn Leu Ser Asp Trp Asp Thr Asp
        355                 360                 365 agc gat gtg ctg tca ctg ctg gat gtg gtg cgc aat gta aaa cca gat     1152
```

```
Ser Asp Val Leu Ser Leu Leu Asp Val Val Arg Asn Val Lys Pro Asp
    370                 375                 380 att ctg att ggc gtc tca gga cag acc ggg ctg ttt acg gaa gag atc      1200
Ile Leu Ile Gly Val Ser Gly Gln Thr Gly Leu Phe Thr Glu Glu Ile
385                 390                 395                 400 atc cgt gag atg cat aaa cac tgt ccg cgt ccg atc gtg atg ccg ctg      1248
Ile Arg Glu Met His Lys His Cys Pro Arg Pro Ile Val Met Pro Leu
                405                 410                 415 tct aac ccg acg tca cgc gtg gaa gcc aca ccg cag gac att atc gcc      1296
Ser Asn Pro Thr Ser Arg Val Glu Ala Thr Pro Gln Asp Ile Ile Ala
        420                 425                 430 tgg acc gaa ggt aac gcg ctg gtc gcc acg ggc agc ccg ttt aat cca      1344
Trp Thr Glu Gly Asn Ala Leu Val Ala Thr Gly Ser Pro Phe Asn Pro
    435                 440                 445 gtg gta tgg aaa gat aaa atc tac cct atc gcc cag tgt aac aac gcc      1392
Val Val Trp Lys Asp Lys Ile Tyr Pro Ile Ala Gln Cys Asn Asn Ala
450                 455                 460 ttt att ttc ccg ggc atc ggc ctg ggt gtt att gct tcc ggc gcg tca      1440
Phe Ile Phe Pro Gly Ile Gly Leu Gly Val Ile Ala Ser Gly Ala Ser
465                 470                 475                 480 cgt atc acc gat gag atg ctg atg tcg gca agt gaa acg ctg gcg cag      1488
Arg Ile Thr Asp Glu Met Leu Met Ser Ala Ser Glu Thr Leu Ala Gln
                485                 490                 495 tat tca cca ttg gtg ctg aac ggc gaa ggt atg gta ctg ccg gaa ctg      1536
Tyr Ser Pro Leu Val Leu Asn Gly Glu Gly Met Val Leu Pro Glu Leu
        500                 505                 510 aaa gat att cag aaa gtc tcc cgc gca att gcg ttt gcg gtt ggc aaa      1584
Lys Asp Ile Gln Lys Val Ser Arg Ala Ile Ala Phe Ala Val Gly Lys
    515                 520                 525 atg gcg cag cag caa ggc gtg gcg gtg aaa acc tct gcc gaa gcc ctg      1632
Met Ala Gln Gln Gln Gly Val Ala Val Lys Thr Ser Ala Glu Ala Leu
530                 535                 540 caa cag gcc att gac gat aat ttc tgg caa gcc gaa tac cgc gac tac      1680
Gln Gln Ala Ile Asp Asp Asn Phe Trp Gln Ala Glu Tyr Arg Asp Tyr
545                 550                 555                 560 cgc cgt acc tcc atc taa                                              1698
Arg Arg Thr Ser Ile
                565

<210> SEQ ID NO 53
<211> LENGTH: 565
<212> TYPE: PRT
<213> ORGANISM: Escherichia coli

<400> SEQUENCE: 53

Met Glu Pro Lys Thr Lys Lys Gln Arg Ser Leu Tyr Ile Pro Tyr Ala
1               5                   10                  15

Gly Pro Val Leu Leu Glu Phe Pro Leu Leu Asn Lys Gly Ser Ala Phe
            20                  25                  30

Ser Met Glu Glu Arg Arg Asn Phe Asn Leu Gly Leu Leu Pro Glu
        35                  40                  45

Val Val Glu Thr Ile Glu Gln Ala Glu Arg Ala Trp Ile Gln Tyr
50                  55                  60

Gln Gly Phe Lys Thr Glu Ile Asp Lys His Ile Tyr Leu Arg Asn Ile
65                  70                  75                  80

Gln Asp Thr Asn Glu Thr Leu Phe Tyr Arg Leu Val Asn Asn His Leu
                85                  90                  95

Asp Glu Met Met Pro Val Ile Tyr Thr Pro Thr Val Gly Ala Ala Cys
            100                 105                 110
```

```
Glu Arg Phe Ser Glu Ile Tyr Arg Arg Ser Arg Gly Val Phe Ile Ser
        115                 120                 125

Tyr Gln Asn Arg His Asn Met Asp Asp Ile Leu Gln Asn Val Pro Asn
130                 135                 140

His Asn Ile Lys Val Ile Val Val Thr Asp Gly Glu Arg Ile Leu Gly
145                 150                 155                 160

Leu Gly Asp Gln Gly Ile Gly Gly Met Gly Ile Pro Ile Gly Lys Leu
                165                 170                 175

Ser Leu Tyr Thr Ala Cys Gly Gly Ile Ser Pro Ala Tyr Thr Leu Pro
            180                 185                 190

Val Val Leu Asp Val Gly Thr Asn Asn Gln Gln Leu Leu Asn Asp Pro
        195                 200                 205

Leu Tyr Met Gly Trp Arg Asn Pro Arg Ile Thr Asp Asp Glu Tyr Tyr
    210                 215                 220

Glu Phe Val Asp Glu Phe Ile Gln Ala Val Lys Gln Arg Trp Pro Asp
225                 230                 235                 240

Val Leu Leu Gln Phe Glu Asp Phe Ala Gln Lys Asn Ala Met Pro Leu
                245                 250                 255

Leu Asn Arg Tyr Arg Asn Glu Ile Cys Ser Phe Asn Asp Asp Ile Gln
            260                 265                 270

Gly Thr Ala Ala Val Thr Val Gly Thr Leu Ile Ala Ala Ser Arg Ala
        275                 280                 285

Ala Gly Gly Gln Leu Ser Glu Lys Lys Ile Val Phe Leu Gly Ala Gly
    290                 295                 300

Ser Ala Gly Cys Gly Ile Ala Glu Met Ile Ile Ser Gln Thr Gln Arg
305                 310                 315                 320

Glu Gly Leu Ser Glu Glu Ala Ala Arg Gln Lys Val Phe Met Val Asp
                325                 330                 335

Arg Phe Gly Leu Leu Thr Asp Lys Met Pro Asn Leu Leu Pro Phe Gln
            340                 345                 350

Thr Lys Leu Val Gln Lys Arg Glu Asn Leu Ser Asp Trp Asp Thr Asp
        355                 360                 365

Ser Asp Val Leu Ser Leu Leu Asp Val Val Arg Asn Val Lys Pro Asp
    370                 375                 380

Ile Leu Ile Gly Val Ser Gly Gln Thr Gly Leu Phe Thr Glu Glu Ile
385                 390                 395                 400

Ile Arg Glu Met His Lys His Cys Pro Arg Pro Ile Val Met Pro Leu
                405                 410                 415

Ser Asn Pro Thr Ser Arg Val Glu Ala Thr Pro Gln Asp Ile Ile Ala
            420                 425                 430

Trp Thr Glu Gly Asn Ala Leu Val Ala Thr Gly Ser Pro Phe Asn Pro
        435                 440                 445

Val Val Trp Lys Asp Lys Ile Tyr Pro Ile Ala Gln Cys Asn Asn Ala
    450                 455                 460

Phe Ile Phe Pro Gly Ile Gly Leu Gly Val Ile Ala Ser Gly Ala Ser
465                 470                 475                 480

Arg Ile Thr Asp Glu Met Leu Met Ser Ala Ser Glu Thr Leu Ala Gln
                485                 490                 495

Tyr Ser Pro Leu Val Leu Asn Gly Glu Gly Met Val Leu Pro Glu Leu
            500                 505                 510

Lys Asp Ile Gln Lys Val Ser Arg Ala Ile Ala Phe Ala Val Gly Lys
        515                 520                 525
```

```
Met Ala Gln Gln Gln Gly Val Ala Val Lys Thr Ser Ala Glu Ala Leu
    530                 535                 540
Gln Gln Ala Ile Asp Asp Asn Phe Trp Gln Ala Glu Tyr Arg Asp Tyr
545                 550                 555                 560
Arg Arg Thr Ser Ile
                565

<210> SEQ ID NO 54
<211> LENGTH: 2280
<212> TYPE: DNA
<213> ORGANISM: Escherichia coli
<220> FEATURE:
<221> NAME/KEY: CDS
<222> LOCATION: (1)..(2280)

<400> SEQUENCE: 54 atg gat gac cag tta aaa caa agt gca ctt gat ttc cat gaa ttt cca     48
Met Asp Asp Gln Leu Lys Gln Ser Ala Leu Asp Phe His Glu Phe Pro
1               5                   10                  15 gtt cca ggg aaa atc cag gtt tct cca acc aag cct ctg gca aca cag     96
Val Pro Gly Lys Ile Gln Val Ser Pro Thr Lys Pro Leu Ala Thr Gln
            20                  25                  30 cgc gat ctg gcg ctg gcc tac tca cca ggc gtt gcc gca cct tgt ctt    144
Arg Asp Leu Ala Leu Ala Tyr Ser Pro Gly Val Ala Ala Pro Cys Leu
        35                  40                  45 gaa atc gaa aaa gac ccg tta aaa gcc tac aaa tat acc gcc cga ggt    192
Glu Ile Glu Lys Asp Pro Leu Lys Ala Tyr Lys Tyr Thr Ala Arg Gly
    50                  55                  60 aac ctg gtg gcg gtg atc tct aac ggt acg gcg gtg ctg ggg tta ggc    240
Asn Leu Val Ala Val Ile Ser Asn Gly Thr Ala Val Leu Gly Leu Gly
65                  70                  75                  80 aac att ggc gcg ctg gca ggc aaa ccg gtg atg gaa ggc aag ggc gtt    288
Asn Ile Gly Ala Leu Ala Gly Lys Pro Val Met Glu Gly Lys Gly Val
                85                  90                  95 ctg ttt aag aaa ttc gcc ggg att gat gta ttt gac att gaa gtt gac    336
Leu Phe Lys Lys Phe Ala Gly Ile Asp Val Phe Asp Ile Glu Val Asp
            100                 105                 110 gaa ctc gac ccg gac aaa ttt att gaa gtt gtc gcc gcg ctc gaa cca    384
Glu Leu Asp Pro Asp Lys Phe Ile Glu Val Val Ala Ala Leu Glu Pro
        115                 120                 125 acc ttc ggc ggc atc aac ctc gaa gac att aaa gcg cca gaa tgt ttc    432
Thr Phe Gly Gly Ile Asn Leu Glu Asp Ile Lys Ala Pro Glu Cys Phe
    130                 135                 140 tat att gaa cag aaa ctg cgc gag cgg atg aat att ccg gta ttc cac    480
Tyr Ile Glu Gln Lys Leu Arg Glu Arg Met Asn Ile Pro Val Phe His
145                 150                 155                 160 gac gat cag cac ggc acg gca att atc agc act gcc gcc atc ctc aac    528
Asp Asp Gln His Gly Thr Ala Ile Ile Ser Thr Ala Ala Ile Leu Asn
                165                 170                 175 ggc ttg cgc gtg gtg gag aaa aac atc tcc gac gtg cgg atg gtg gtt    576
Gly Leu Arg Val Val Glu Lys Asn Ile Ser Asp Val Arg Met Val Val
            180                 185                 190 tcc ggc gcg ggt gcc gca gca atc gcc tgt atg aac ctg ctg gta gcg    624
Ser Gly Ala Gly Ala Ala Ala Ile Ala Cys Met Asn Leu Leu Val Ala
        195                 200                 205 ctg ggt ctg caa aaa cat aac atc gtg gtt tgc gat tca aaa ggc gtt    672
Leu Gly Leu Gln Lys His Asn Ile Val Val Cys Asp Ser Lys Gly Val
    210                 215                 220 atc tat cag ggc cgt gag cca aac atg gcg gaa acc aaa gcc gca tat    720
Ile Tyr Gln Gly Arg Glu Pro Asn Met Ala Glu Thr Lys Ala Ala Tyr
225                 230                 235                 240
```

```
gcg gtg gtg gat gac ggc aaa cgt acc ctc gat gat gtg att gaa ggc     768
Ala Val Val Asp Asp Gly Lys Arg Thr Leu Asp Asp Val Ile Glu Gly
                245                 250                 255 gcg gat att ttc ctg ggc tgt tcc ggc ccg aaa gtg ctg acc cag gaa     816
Ala Asp Ile Phe Leu Gly Cys Ser Gly Pro Lys Val Leu Thr Gln Glu
        260                 265                 270 atg gtg aag aaa atg gct cgt gcg cca atg atc ctg gcg ctg gcg aac     864
Met Val Lys Lys Met Ala Arg Ala Pro Met Ile Leu Ala Leu Ala Asn
            275                 280                 285 ccg gaa ccg gaa att ctg ccg ccg ctg gcg aaa gaa gtg cgt ccg gat     912
Pro Glu Pro Glu Ile Leu Pro Pro Leu Ala Lys Glu Val Arg Pro Asp
290                 295                 300 gcc atc att tgc acc ggt cgt tct gac tat ccg aac cag gtg aac aac     960
Ala Ile Ile Cys Thr Gly Arg Ser Asp Tyr Pro Asn Gln Val Asn Asn
305                 310                 315                 320 gtc ctg tgc ttc ccg ttc atc ttc cgt ggc gcg ctg gac gtt ggc gca    1008
Val Leu Cys Phe Pro Phe Ile Phe Arg Gly Ala Leu Asp Val Gly Ala
                325                 330                 335 acc gcc atc aac gaa gag atg aaa ctg gcg gcg gta cgt gcg att gca    1056
Thr Ala Ile Asn Glu Glu Met Lys Leu Ala Ala Val Arg Ala Ile Ala
                340                 345                 350 gaa ctc gcc cat gcg gaa cag agc gaa gtg gtg gct tca gcg tat ggc    1104
Glu Leu Ala His Ala Glu Gln Ser Glu Val Val Ala Ser Ala Tyr Gly
            355                 360                 365 gat cag gat ctg agc ttt ggt ccg gaa tac atc att cca aaa ccg ttt    1152
Asp Gln Asp Leu Ser Phe Gly Pro Glu Tyr Ile Ile Pro Lys Pro Phe
370                 375                 380 gat ccg cgc ttg atc gtt aag atc gct cct gcg gtc gct aaa gcc gcg    1200
Asp Pro Arg Leu Ile Val Lys Ile Ala Pro Ala Val Ala Lys Ala Ala
385                 390                 395                 400 atg gag tcg ggc gtg gcg act cgt ccg att gct gat ttc gac gtc tac    1248
Met Glu Ser Gly Val Ala Thr Arg Pro Ile Ala Asp Phe Asp Val Tyr
                405                 410                 415 atc gac aag ctg act gag ttc gtt tac aaa acc aac ctg ttt atg aag    1296
Ile Asp Lys Leu Thr Glu Phe Val Tyr Lys Thr Asn Leu Phe Met Lys
                420                 425                 430 ccg att ttc tcc cag gct cgc aaa gcg ccg aag cgc gtt gtt ctg ccg    1344
Pro Ile Phe Ser Gln Ala Arg Lys Ala Pro Lys Arg Val Val Leu Pro
            435                 440                 445 gaa ggg gaa gag gcg cgc gtt ctg cat gcc act cag gaa ctg gta acg    1392
Glu Gly Glu Glu Ala Arg Val Leu His Ala Thr Gln Glu Leu Val Thr
450                 455                 460 ctg gga ctg gcg aaa ccg atc ctt atc ggt cgt ccg aac gtg atc gaa    1440
Leu Gly Leu Ala Lys Pro Ile Leu Ile Gly Arg Pro Asn Val Ile Glu
465                 470                 475                 480 atg cgc att cag aaa ctg ggc ttg cag atc aaa gcg ggc gtt gat ttt    1488
Met Arg Ile Gln Lys Leu Gly Leu Gln Ile Lys Ala Gly Val Asp Phe
                485                 490                 495 gag atc gtc aat aac gaa tcc gat ccg cgc ttt aaa gag tac tgg acc    1536
Glu Ile Val Asn Asn Glu Ser Asp Pro Arg Phe Lys Glu Tyr Trp Thr
                500                 505                 510 gaa tac ttc cag atc atg aag cgt cgc ggc gtc act cag gaa cag gcg    1584
Glu Tyr Phe Gln Ile Met Lys Arg Arg Gly Val Thr Gln Glu Gln Ala
            515                 520                 525 cag cgg gcg ctg atc agt aac ccg aca gtg atc ggc gcg atc atg gtt    1632
Gln Arg Ala Leu Ile Ser Asn Pro Thr Val Ile Gly Ala Ile Met Val
530                 535                 540 cag cgt ggg gaa gcc gat gca atg att tgc ggt acg gtg ggt gat tat    1680
Gln Arg Gly Glu Ala Asp Ala Met Ile Cys Gly Thr Val Gly Asp Tyr
```

```
                   545                 550                 555                 560
cat gaa cat ttt agc gtg gtg aaa aat gtc ttt ggt tat cgc gat ggc        1728
His Glu His Phe Ser Val Val Lys Asn Val Phe Gly Tyr Arg Asp Gly
                    565                 570                 575 gtt cac acc gca ggt gcc atg aac gcg ctg ctg ctg ccg agt ggt aac        1776
Val His Thr Ala Gly Ala Met Asn Ala Leu Leu Leu Pro Ser Gly Asn
                580                 585                 590 acc ttt att gcc gat aca tat gtt aat gat gaa ccg gat gca gaa gag        1824
Thr Phe Ile Ala Asp Thr Tyr Val Asn Asp Glu Pro Asp Ala Glu Glu
            595                 600                 605 ctg gcg gag atc acc ttg atg gcg gca gaa act gtc cgt cgt ttt ggt        1872
Leu Ala Glu Ile Thr Leu Met Ala Ala Glu Thr Val Arg Arg Phe Gly
        610                 615                 620 att gag ccg cgc gtt gct ttg ttg tcg cac tcc aac ttt ggt tct tct        1920
Ile Glu Pro Arg Val Ala Leu Leu Ser His Ser Asn Phe Gly Ser Ser
    625                 630                 635                 640 gac tgc ccg tcg tcg agc aaa atg cgt cag gcg ctg gaa ctg gtc agg        1968
Asp Cys Pro Ser Ser Ser Lys Met Arg Gln Ala Leu Glu Leu Val Arg
                    645                 650                 655 gaa cgt gca cca gaa ctg atg att gat ggt gaa atg cac ggc gat gca        2016
Glu Arg Ala Pro Glu Leu Met Ile Asp Gly Glu Met His Gly Asp Ala
                660                 665                 670 gcg ctg gtg gaa gcg att cgc aac gac cgt atg ccg gac agc tct ttg        2064
Ala Leu Val Glu Ala Ile Arg Asn Asp Arg Met Pro Asp Ser Ser Leu
            675                 680                 685 aaa ggt tcc gcc aat att ctg gtg atg ccg aac atg gaa gct gcc cgc        2112
Lys Gly Ser Ala Asn Ile Leu Val Met Pro Asn Met Glu Ala Ala Arg
        690                 695                 700 att agt tac aac tta ctg cgt gtt tcc agc tcg gaa ggt gtg act gtc        2160
Ile Ser Tyr Asn Leu Leu Arg Val Ser Ser Ser Glu Gly Val Thr Val
705                 710                 715                 720 ggc ccg gtg ctg atg ggt gtg gcg aaa ccg gtt cac gtg tta acg ccg        2208
Gly Pro Val Leu Met Gly Val Ala Lys Pro Val His Val Leu Thr Pro
                    725                 730                 735 atc gca tcg gtg cgt cgt atc gtc aac atg gtg gcg ctg gcc gtg gta        2256
Ile Ala Ser Val Arg Arg Ile Val Asn Met Val Ala Leu Ala Val Val
                740                 745                 750 gaa gcg caa acc caa ccg ctg taa                                        2280
Glu Ala Gln Thr Gln Pro Leu
            755

<210> SEQ ID NO 55
<211> LENGTH: 759
<212> TYPE: PRT
<213> ORGANISM: Escherichia coli

<400> SEQUENCE: 55

Met Asp Asp Gln Leu Lys Gln Ser Ala Leu Asp Phe His Glu Phe Pro
1               5                   10                  15

Val Pro Gly Lys Ile Gln Val Ser Pro Thr Lys Pro Leu Ala Thr Gln
                20                  25                  30

Arg Asp Leu Ala Leu Ala Tyr Ser Pro Gly Val Ala Ala Pro Cys Leu
            35                  40                  45

Glu Ile Glu Lys Asp Pro Leu Lys Ala Tyr Lys Tyr Thr Ala Arg Gly
        50                  55                  60

Asn Leu Val Ala Val Ile Ser Asn Gly Thr Ala Val Leu Gly Leu Gly
65                  70                  75                  80

Asn Ile Gly Ala Leu Ala Gly Lys Pro Val Met Glu Gly Lys Gly Val
                85                  90                  95
```

```
Leu Phe Lys Lys Phe Ala Gly Ile Asp Val Phe Asp Ile Glu Val Asp
            100                 105                 110

Glu Leu Asp Pro Asp Lys Phe Ile Glu Val Val Ala Ala Leu Glu Pro
        115                 120                 125

Thr Phe Gly Gly Ile Asn Leu Glu Asp Ile Lys Ala Pro Glu Cys Phe
    130                 135                 140

Tyr Ile Glu Gln Lys Leu Arg Glu Arg Met Asn Ile Pro Val Phe His
145                 150                 155                 160

Asp Asp Gln His Gly Thr Ala Ile Ile Ser Thr Ala Ala Ile Leu Asn
                165                 170                 175

Gly Leu Arg Val Val Glu Lys Asn Ile Ser Asp Val Arg Met Val Val
            180                 185                 190

Ser Gly Ala Gly Ala Ala Ala Ile Ala Cys Met Asn Leu Leu Val Ala
        195                 200                 205

Leu Gly Leu Gln Lys His Asn Ile Val Val Cys Asp Ser Lys Gly Val
    210                 215                 220

Ile Tyr Gln Gly Arg Glu Pro Asn Met Ala Glu Thr Lys Ala Ala Tyr
225                 230                 235                 240

Ala Val Val Asp Asp Gly Lys Arg Thr Leu Asp Asp Val Ile Glu Gly
                245                 250                 255

Ala Asp Ile Phe Leu Gly Cys Ser Gly Pro Lys Val Leu Thr Gln Glu
            260                 265                 270

Met Val Lys Lys Met Ala Arg Ala Pro Met Ile Leu Ala Leu Ala Asn
        275                 280                 285

Pro Glu Pro Glu Ile Leu Pro Pro Leu Ala Lys Glu Val Arg Pro Asp
    290                 295                 300

Ala Ile Ile Cys Thr Gly Arg Ser Asp Tyr Pro Asn Gln Val Asn Asn
305                 310                 315                 320

Val Leu Cys Phe Pro Phe Ile Phe Arg Gly Ala Leu Asp Val Gly Ala
                325                 330                 335

Thr Ala Ile Asn Glu Glu Met Lys Leu Ala Ala Val Arg Ala Ile Ala
            340                 345                 350

Glu Leu Ala His Ala Glu Gln Ser Glu Val Val Ala Ser Ala Tyr Gly
        355                 360                 365

Asp Gln Asp Leu Ser Phe Gly Pro Glu Tyr Ile Ile Pro Lys Pro Phe
    370                 375                 380

Asp Pro Arg Leu Ile Val Lys Ile Ala Pro Ala Val Ala Lys Ala Ala
385                 390                 395                 400

Met Glu Ser Gly Val Ala Thr Arg Pro Ile Ala Asp Phe Asp Val Tyr
                405                 410                 415

Ile Asp Lys Leu Thr Glu Phe Val Tyr Lys Thr Asn Leu Phe Met Lys
            420                 425                 430

Pro Ile Phe Ser Gln Ala Arg Lys Ala Pro Lys Arg Val Val Leu Pro
        435                 440                 445

Glu Gly Glu Glu Ala Arg Val Leu His Ala Thr Gln Glu Leu Val Thr
    450                 455                 460

Leu Gly Leu Ala Lys Pro Ile Leu Ile Gly Arg Pro Asn Val Ile Glu
465                 470                 475                 480

Met Arg Ile Gln Lys Leu Gly Leu Gln Ile Lys Ala Gly Val Asp Phe
                485                 490                 495

Glu Ile Val Asn Asn Glu Ser Asp Pro Arg Phe Lys Glu Tyr Trp Thr
            500                 505                 510
```

-continued

```
Glu Tyr Phe Gln Ile Met Lys Arg Arg Gly Val Thr Gln Glu Gln Ala
            515                 520                 525

Gln Arg Ala Leu Ile Ser Asn Pro Thr Val Ile Gly Ala Ile Met Val
            530                 535                 540

Gln Arg Gly Glu Ala Asp Ala Met Ile Cys Gly Thr Val Gly Asp Tyr
545                 550                 555                 560

His Glu His Phe Ser Val Val Lys Asn Val Phe Gly Tyr Arg Asp Gly
            565                 570                 575

Val His Thr Ala Gly Ala Met Asn Ala Leu Leu Leu Pro Ser Gly Asn
            580                 585                 590

Thr Phe Ile Ala Asp Thr Tyr Val Asn Asp Glu Pro Asp Ala Glu Glu
            595                 600                 605

Leu Ala Glu Ile Thr Leu Met Ala Ala Glu Thr Val Arg Arg Phe Gly
            610                 615                 620

Ile Glu Pro Arg Val Ala Leu Leu Ser His Ser Asn Phe Gly Ser Ser
625                 630                 635                 640

Asp Cys Pro Ser Ser Ser Lys Met Arg Gln Ala Leu Glu Leu Val Arg
                645                 650                 655

Glu Arg Ala Pro Glu Leu Met Ile Asp Gly Glu Met His Gly Asp Ala
                660                 665                 670

Ala Leu Val Glu Ala Ile Arg Asn Asp Arg Met Pro Asp Ser Ser Leu
                675                 680                 685

Lys Gly Ser Ala Asn Ile Leu Val Met Pro Asn Met Glu Ala Ala Arg
            690                 695                 700

Ile Ser Tyr Asn Leu Leu Arg Val Ser Ser Ser Glu Gly Val Thr Val
705                 710                 715                 720

Gly Pro Val Leu Met Gly Val Ala Lys Pro Val His Val Leu Thr Pro
                725                 730                 735

Ile Ala Ser Val Arg Arg Ile Val Asn Met Val Ala Leu Ala Val Val
                740                 745                 750

Glu Ala Gln Thr Gln Pro Leu
            755
```

AMINO ACID PRODUCING MICROORGANISM AND A METHOD FOR PRODUCING AN AMINO ACID

This application claims priority under 35 U.S.C. §119 to Japanese Patent Application No. 2007-228733, filed Sep. 4, 2007, which is incorporated by reference. The Sequence Listing in electronic format filed herewith is also hereby incorporated by reference in its entirety (File Name: US-372_Seq_List_Copy_1; File Size: 210 KB; Date Created: Sep. 2, 2008).

TECHNICAL FIELD

The present invention relates to a microorganism which produces an L-amino acid and a method for producing an L-amino acid. L-lysine and L-tryptophan are widely used as feed additives, etc. L-phenylalanine is used as a raw material in the production of sweeteners. L-valine, L-leucine, and L-isoleucine are used for amino acid infusions or supplements. L-serine is useful as a food additive and a raw material in the production of cosmetics, etc.

BACKGROUND ART

Methods for production of a target substance, such as an L-amino acid, by fermentation of a microorganism have been reported. The microorganisms used for this purpose include wild-type microorganisms (wild-type strain), auxotrophic strains derived from wild-type strains, metabolic regulation mutant strains derived from wild-type strains which are resistant to various drugs, strains which act as both auxotrophic and metabolic regulation mutants, and so forth.

In recent years, recombinant DNA techniques have been used in the production of target substances by fermentation. For example, it is well-known that L-amino acid productivity of a microorganism can be improved by enhancing expression of a gene encoding an L-amino acid biosynthetic enzyme or by enhancing uptake of a carbon source to the L-amino acid biosynthesis system.

For example, known methods include, for L-lysine, enhancing expression of genes encoding enzymes such as dihydrodipicolinate synthase, aspartokinase, dihydrodipicolinate reductase, diaminopimelate decarboxylase, and diarinopimelate dehydrogenase (U.S. Pat. No. 6,040,160), reducing the activities of homoserine dehydrogenase and lysine decarboxylase (U.S. Pat. No. 5,827,698), reducing the activity of the malic enzyme (WO2005/010175), and so forth.

For L-tryptophan, desensitization to the feedback inhibition of phosphoglycerate dehydrogenase and anthranilate synthase (U.S. Pat. No. 6,180,373), deletion of tryptophanase (U.S. Pat. No. 4,371,614), and so forth are known.

For L-phenylalanine, desensitization to the feedback inhibition of chorismate mutase-prephenate dehydratase (U.S. Pat. No. 5,354,672), deletion of chorismate mutase-prephenate dehydrogenase and tyrosine repressor (WO03/044191), and so forth are known.

For L-valine, a mutant strain requiring lipoic acid for its growth and/or which is deficient in $H^+$-ATPase (U.S. Pat. No. 5,888,783), and so forth are known. For L-leucine, desensitization to the feedback inhibition of isopropyl malate synthase (U.S. Pat. No. 6,403,342) and so forth are known, and for L-isoleucine, increasing the expression of genes encoding threonine deaminase and acetohydroxy acid synthase (U.S. Pat. No. 5,998,178), and so forth are known.

For L-serine, a strain containing 3-phosphoglycerate dehydrogenase which is desensitized to feedback inhibition by serine (U.S. Pat. No. 5,618,716), a bacterium having L-serine-producing ability and at least phosphoserine phosphatase activity, phosphoserine transaminase activity, or both, is enhanced, a bacterium deficient in L-serine decomposition ability (U.S. Pat. No. 6,037,154), a bacterium resistant to azaserine or β-(2-thienyl)-DL-alanine and having L-serine-producing ability (U.S. Pat. No. 6,258,573), and so forth are known.

SUMMARY OF THE INVENTION

The present invention provides a bacterial strain which can efficiently produce an L-amino acid. A method is also provided for efficiently producing an L-amino acid using such a strain.

Conventional L-amino acid production is mainly based on maintaining the supply of acetyl-CoA to the TCA cycle by pyruvate dehydrogenase using sugar as the carbon source. However, since the reaction catalyzed by pyruvate dehydrogenase is accompanied by decarboxylation, one molecule of $CO_2$ is inevitably released. Therefore, in order to further increase the productivity, it is necessary to decrease this decarboxylation. As a result, ethanol and aliphatic acids can be used as the carbon source which provides acetyl-CoA. Also, the enzymatic activity of pyruvate synthase can be increased. This enzyme catalyzes carbon dioxide fixation, or pyruvate:$NADP^+$ oxidoreductase. Furthermore, L-amino acid production can be improved by increasing the enzymatic activity of ferredoxin-$NADP^+$ reductase, which reduces ferredoxin or flavodoxin from the oxidized proteins, and is required for the enzymatic activity of pyruvate synthase. Also, the ability to produce ferredoxin or flavodoxin can be increased.

It is an aspect of the present invention to provide a microorganism which has an ability to produce an L-amino acid selected from the group consisting of L-lysine, L-tryptophan, L-phenylalanine, L-valine, L-leucine, L-isoleucine and L-serine, and has been modified to increase the activity of pyruvate synthase or pyruvate:$NADP^+$ oxidoreductase.

It is a further aspect of the present invention to provide the aforementioned microorganism, which is modified to increase the activity of pyruvate synthase.

It is a further aspect of the present invention to provide the aforementioned microorganism, which is modified to increase the activity of pyruvate:$NADP^+$ oxidoreductase.

It is a further aspect of the present invention to provide the aforementioned microorganism, wherein the activity of pyruvate synthase or pyruvate:$NADP^+$ oxidoreductase is increased by a method selected from the group consisting of A) increasing expression of the gene encoding pyruvate synthase or pyruvate:$NADP^+$ oxidoreductase, b) increasing translation of the gene, and c) combinations thereof.

It is a further aspect of the present invention to provide the aforementioned microorganism, wherein the activity of pyruvate synthase or pyruvate:$NADP^+$ oxidoreductase is increased by increasing the copy number of the gene encoding pyruvate synthase or pyruvate:$NADP^+$ oxidoreductase, or by modifying an expression control sequence of the gene.

It is a further aspect of the present invention to provide the aforementioned microorganism, wherein pyruvate synthase is selected from the group consisting of:

(A) a polypeptide comprising the amino acid sequence shown in SEQ ID NO: 2, (B) a polypeptide comprising the amino acid sequence shown in SEQ ID NO: 2, but which includes one or more substitutions, deletions, insertions, or additions of one or several amino acid residues, and having pyruvate synthase activity, (C) a polypeptide comprising the amino acid sequence shown in SEQ ID NO: 4, (D) a polypeptide comprising the amino acid sequence shown in SEQ ID NO: 4, but which includes one or more substitutions, deletions, insertions, or additions of one or several amino acid residues and having pyruvate synthase activity.

It is a further aspect of the present invention to provide the aforementioned microorganism, wherein the gene encoding pyruvate synthase is selected from the group consisting of:

(a) a DNA comprising the nucleotide sequence shown in SEQ ID NO: 1, (b) a DNA which is able to hybridize with a sequence complementary to the nucleotide sequence shown in SEQ ID NO: 1, or a probe which is prepared from the nucleotide sequence, under stringent conditions, and encoding a polypeptide having pyruvate synthase activity, (c) a DNA comprising the nucleotide sequence shown in SEQ ID NO: 3, (d) a DNA which is able to hybridize with a sequence complementary to the nucleotide sequence shown in SEQ ID NO: 3, or a probe which can be prepared from the nucleotide sequence, under stringent conditions, and encoding a polypeptide having pyruvate synthase activity.

(8) The aforementioned microorganism, wherein NADP$^+$ oxidoreductase is selected from the group consisting of:

(A) a polypeptide comprising the amino acid sequence shown in SEQ ID NO: 6, (B) a polypeptide comprising the amino acid sequence shown in SEQ ID NO: 6, but which includes one or more substitutions, deletions, insertions or addition of one or several amino acid residues and having pyruvate:NADP$^+$ oxidoreductase activity.

It is a further aspect of the present invention to provide the aforementioned microorganism, wherein the gene encoding pyruvate:NADP$^+$ oxidoreductase is selected from the group consisting of:

(a) a DNA comprising the nucleotide sequence shown in SEQ ID NO: 5, (b) a DNA which is able to hybridize with a sequence complementary to the nucleotide sequence shown in SEQ ID NO: 5, or a probe which can be prepared from the nucleotide sequence, under stringent conditions, and encoding a polypeptide having pyruvate:NADP$^+$ oxidoreductase activity.

It is a further aspect of the present invention to provide the aforementioned microorganism, which has been modified to increase the activity of ferredoxin-NADP$^+$ reductase.

It is a further aspect of the present invention to provide the aforementioned microorganism, which has been modified to improve the ability of said microorganism to produce ferredoxin or flavodoxin.

It is a further aspect of the present invention to provide the aforementioned microorganism, which has been modified to decrease pyruvate dehydrogenase activity.

It is a further aspect of the present invention to provide the aforementioned microorganism, which has been modified so that it can aerobically assimilate ethanol.

It is a further aspect of the present invention to provide the aforementioned microorganism, wherein said microorganism is a bacterium belonging to a genus selected from the group consisting of *Escherichia, Enterobacter, Pantoea, Klebsiella* and *Serratia*.

It is a further aspect of the present invention to provide the aforementioned microorganism, which is a coryneform bacterium.

It is a further aspect of the present invention to provide a method for producing an L-amino acid comprising culturing the aforementioned microorganism in a medium to produce an L-amino acid selected from the group consisting of L-lysine, L-tryptophan, L-phenylalanine, L-valine, L-leucine, L-isoleucine, and L-serine, and collecting the L-amino acid from the medium or the microorganism.

It is a further aspect of the present invention to provide the aforementioned method, wherein the medium contains ethanol or an aliphatic acid as the carbon source.

Figure 1:
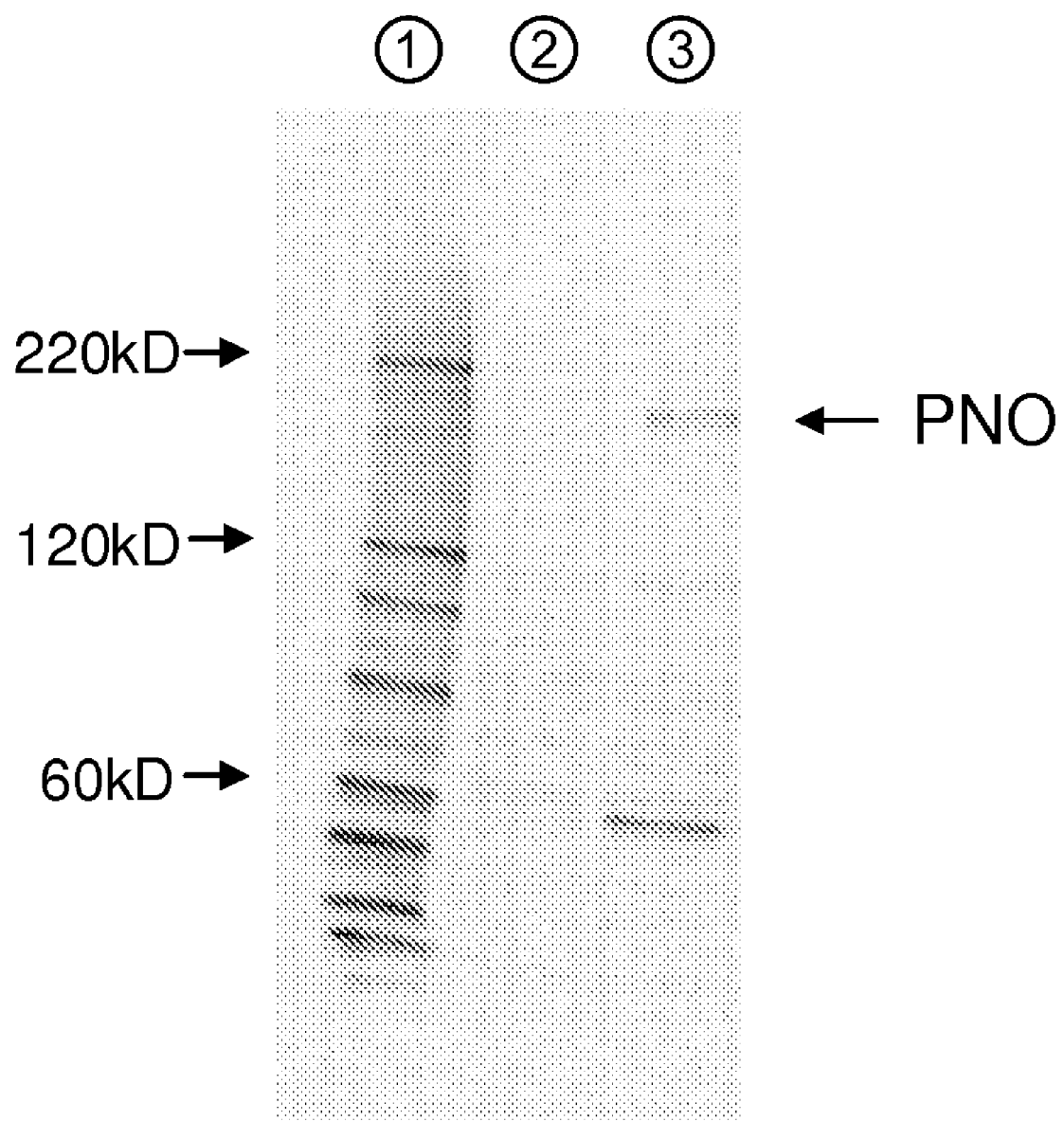
FIG. 1 is a photograph showing the result of Western blotting showing expression of the pyruvate:NADP$^+$ oxidoreductase (PNO) gene derived from *Euglena gracilis*.

Lane 1: Markers
Lane 2: Crude enzyme extract obtained from WC196ΔcadAΔldc/pCABD2/pMW-Pthr
Lane 3: Crude enzyme extract obtained from WC196ΔcadAΔldc/pCABD2/pMW-Pthr-PNO.

DESCRIPTION OF THE PREFERRED EMBODIMENTS

Hereinafter, the present invention will be explained in detail.

<1> Microorganism

The microorganism has the ability to produced an L-amino acid, such as L-lysine, L-tryptophan, L-phenylalanine, L-valine, L-leucine, L-isoleucine, and L-serine, and has been modified to increase an activity of pyruvate synthase orpyruvate:NADP$^+$ oxidoreductase.

The "L-amino acid" means L-lysine, L-tryptophan, L-phenylalanine, L-valine, L-leucine, L-isoleucine, and L-serine, unless specifically mentioned otherwise.

The phrase "ability to produce an L-amino acid (L-amino acid-producing ability)" refers to the ability to produce an L-amino acid and cause accumulation of the L-amino acid in the cells of the microorganism or into the medium to such a degree that the L-amino acid can be collected from the cells or medium when the microorganism is cultured in the medium. One or more amino acids may be produced by the microorganism. The microorganism may inherently have the ability to produce the L-amino acid, or the ability may be imparted by modifying the microorganism using mutagenesis or recombinant DNA techniques, or by introducing the gene described herein to the microorganism.

The expression "activity of pyruvate synthase or pyruvate:NADP$^+$ oxidoreductase is increased" or "to increase the activity of pyruvate synthase orpyruvate:NADP$^+$ oxidoreductase" means that the activity of pyruvate synthase or pyruvate:NADP$^+$ oxidoreductase increases in a microorganism which inherently has pyruvate synthase and/or pyruvate:NADP$^+$ oxidoreductase, or that the activity of pyruvate synthase or pyruvate:NADP$^+$ oxidoreductase is imparted to a microorganism to which pyruvate synthase and pyruvate:NADP$^+$ oxidoreductase are not native.

<1-1> Impairing the Ability to Produce an L-Amino Acid

The microorganism can be obtained by modifying a parent strain which is able to produce an L-amino acid so that the activity of pyruvate synthase or pyruvate:NADP$^+$ oxidoreductase, or both, is increased. The microorganism can also be obtained by modifying a parent strain to have increased activity of pyruvate synthase or pyruvate:NADP+ oxidoreductase, and then imparting or enhancing the ability to produce L-amino acids.

Methods for imparting the L-amino acid-producing ability to a microorganism, and microorganisms imparted with L-amino acid-producing ability, will be exemplified below, but the methods are not limited to these.

Microorganisms belonging to γ-Proteobacteria such as bacteria belonging to the genera *Escherichia, Enterobacter, Pantoea, Klebsiella, Serratia, Erwinia, Salmonella, Morganella*, etc.; coryneform bacteria such as bacteria belonging to the genera *Brevibacterium, Corynebacterium*, and *Microbacterium*; and microorganisms belonging to the genera *Alicyclobacillus, Bacillus*, and *Saccharomyces* can be used. γ-proteobacteria include those classified according to the NCBI (National Center for Biotechnology Information) taxonomy database and can be used.

Examples of *Escherichia* bacteria include *Escherichia coli* and so forth. When *Escherichia coli* strains are bred by using genetic engineering techniques, the *E. coli* K12 strain and derivatives thereof, the *Escherichia coli* MG1655 strain (ATCC 47076), and the W3110 strain (ATCC 27325) can be used. The *Escherichia coli* K12 strain was isolated at Stanford University in 1922. This strain is a lysogenic bacterium of λ phage and has the F-factor. This strain is a highly versatile strain from which genetic recombinants can be constructed by conjugation or the like. Furthermore, the genome sequence of the *Escherichia coli* K12 strain has been determined, and the genetic information can be used freely. The *Escherichia coli* K12 strain and derivatives thereof are available from the American Type Culture Collection (ATCC, Address: P.O. Box 1549, Manassas, Va. 20108, United States of America).

In particular, *Pantoea* bacteria, *Erwinia* bacteria, and *Enterobacter* bacteria are classified as γ-proteobacteria, and they are taxonomically very close to one another (J. Gen. Appl. Microbiol., 1997, 43, 355-361; Int J. Syst. Bacteriol., 1997, 43, 1061-1067). In recent years, some bacteria belonging to the genus *Enterobacter* were reclassified as *Pantoea agglomerans, Pantoea dispersa*, or the like, on the basis of DNA-DNA hybridization experiments etc. (International Journal of Systematic Bacteriology, July 1989, 39:337-345). Furthermore, some bacteria belonging to the genus *Erwinia* were reclassified as *Pantoea ananas* or *Pantoea stewartii* (refer to Int. J. Syst. Bacteriol., 1993, 43:162-173).

Examples of the *Enterobacter* bacteria include, but are not limited to, *Enterobacter agglomerans, Enterobacter aerogenes*, and so forth. Specifically, the strains exemplified in European Patent Publication No. 952221 can be used. A typical strain of the genus *Enterobacter* is the *Enterobacter agglomeranses* ATCC 12287 strain.

Typical strains of the *Pantoea* bacteria include, but are not limited to, *Pantoea ananatis, Pantoea stewartii, Pantoea agglomerans*, and *Pantoea citrea*. Specific examples include the following strains:

*Pantoea ananatis* AJ13355 (FERM BP-6614, European Patent Publication No. 0952221)

*Pantoea ananatis* AJ13356 (FERM BP-6615, European Patent Publication No. 0952221)

Although these strains are described as *Enterobacter agglomerans* in European Patent Publication No. 0952221, they are currently classified as *Pantoea ananatis* on the basis of nucleotide sequence analysis of the 16S rRNA etc., as described above.

Examples of the *Erwinia* bacteria include, but are not limited to, *Erwinia amylovora* and *Erwinia carotovora*, and examples of the *Klebsiella* bacteria include *Klebsiella planticola*. Specific examples include the following strains:

*Erwinia amylovora* ATCC 15580
*Erwinia carotovora* ATCC 15713
*Klebsiella planticola* AJ13399 (FERM BP-6600, European Patent Publication No. 955368)
*Klebsiella planticola* AJ13410 (FERM BP-6617, European Patent Publication No. 955368).

The coryneform bacteria are a group of microorganisms defined in Bergey's Manual of Determinative Bacteriology, 8th Ed., p. 599, 1974, and include aerobic, Gram-positive, and nonacid-fast bacilli which are not able to sporulate, and which were originally classified into the genus *Brevibacterium*, but are now recognized as being in the genus *Corynebacterium* (Liebl, W., Ehrmann, M., Ludwig, W., and Schleifer, K. H., 1991, Int J. Syst. Bacteriol. 41:255-260). These bacteria also include bacteria belonging to the genus *Brevibacterium* or *Microbacterium* which are closely related to the genus *Corynebacterium*.

Specific examples of coryneform bacteria which are used to produce amino acids of the L-glutamic acid family include the following:

*Corynebacterium acetoacidophilum*
*Corynebacterium acetoglutamicum*
*Corynebacterium alkanolyticum*
*Corynebacterium callunae*
*Corynebacterium glutamnicum*
*Corynebacterium lilium* (*Corynebacterium glutarnicum*)
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium ammoniagenes* (*Corynebacterium ammoniagenes*)
*Brevibacterium album*
*Brevibacterium cerinum*
*Microbacterium ammoniaphilum*

Specifically, the following strains can be mentioned:

*Corynebacterium thermoaminogenes* AJ12340 (FERM BP-1539)
*Corynebacterium glutamicum* ATCC 13032
*Brevibacterium flavum* (*Corynebacterium glutamicum*) ATCC 13826, ATCC 14067
*Brevibacterium lactofermentum* (*Corynebacterium glutamicum*) ATCC 13665, ATCC 13869
*Brevibacterium ammoniagenes* (*Corynebacterium ammoniagenes*) ATCC 6871

The bacterium may be able to assimilate ethanol. The bacterium may inherently be able to assimilate ethanol, or the ability to assimilate ethanol may be imparted or increased recombinantly. *Escherichia coli* is known to have AdhE, which has activities of acetaldehyde dehydrogenase and alcohol dehydrogenase, which are enzymes which can generate ethanol under anaerobic conditions, and catalyze the reactions described below.

Acetyl-CoA+NADH+H$^+$=acetaldehyde+NAD$^+$+CoA

Acetaldehyde+NADH+H$^+$=ethanol+NAD$^+$

Although *Escherichia coli* cannot assimilate ethanol under aerobic conditions, the mutation of AdhE results in *Escherichia coli* to be able to aerobically assimilate ethanol (Clark D. P., and Cronan, J. E. Jr., 1980, J. Bacteriol., 144:179-184; Membrillo-Hernandez, J. et al., 2000, J. Biol. Chem., 275: 33869-33875). The specific mutation is that the glutamic acid at position 569 in *Escherichia coli* AdhE is replaced with an amino acid other than glutamic acid and aspartic acid, such as lysine (Glu568Lys or E568K).

The aforementioned AdhE mutant may further include the following additional mutations:

A) Replacement of the glutamic acid at position 560 with another amino acid, such as lysine, B) Replacement of the phenylalanine at position 566 with another amino acid, C) Replacement of the glutamic acid at position 22, methionine at position 236, tyrosine at position 461, isoleucine at position 554, and alanine at position 786, with glycine, valine, cysteine, serine, and valine, respectively, or D) a combination of the aforementioned mutations.

It is known that *Corynebacterium glutamicum* has two or more kinds of alcohol dehydrogenases, and can aerobically assimilate ethanol (Pelechova J, Smekal F. Koura V, Plachy J and Krumphanzl V, 1980, Folia Microbiol (Praha) 25:341-346).

The bacterium may be able to assimilate fat, oil, or an aliphatic acid. The bacterium may inherently be able to assimilate fat, oil, or aliphatic acids, or the ability can be imparted or increased recombinantly. *Escherichia coli* is known to be able to assimilate long chain aliphatic acids having a length of 12 or longer (Clark D. P. and Cronan J. E., 1996, In *Escherichia coli* and *Salmonella*: Cellular and Molecular Biology/Second Edition (Neidhardt, F. C. Ed.) pp. 343-357). Furthermore, *Escherichia coli* strains which were mutated to assimilate short- to medium-chain aliphatic acids are known (Nunn, W. D. et al., 1979, J. Biol. Chem., 254: 9130-9134; Salanitro, J. P. and Wegener, W. S., 1971, J. Bacteriol., 108:885-892).

A bacterium which is able to produce an L-amino acid means that the bacterium can produce and cause accumulation of an L-amino acid in the medium in such an amount that the L-amino acid can be collected from the medium when the bacterium is cultured in the medium. The target L-amino acid can accumulate in the medium in an amount not less than 0.5 g/L, more preferably not less than 1.0 g/L. The "L-amino acid" encompasses L-lysine, L-tryptophan, L-phenylalanine, L-valine, L-leucine, L-isoleucine, and L-serine. L-Lysine and L-tryptophan are especially preferred.

Hereinafter, methods for imparting an L-amino acid-producing ability to such bacteria as mentioned above, or methods for enhancing an L-amino acid-producing ability of such bacteria as described above, are described.

To impart the ability to produce an L-amino acid, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include by acquiring the properties of an auxotrophic mutant, an analogue-resistant strain, or a metabolic regulation mutant, or by constructing a recombinant strain so that it overexpresses an L-amino acid biosynthesis enzyme. Here, in the breeding of an L-amino acid-producing bacteria, one or more of the above described properties may be imparted. The expression of L-amino acid biosynthesis enzyme(s) can be enhanced alone or in combinations of two or more. Furthermore, the methods of imparting properties such as an auxotrophic mutation, analogue resistance, or metabolic regulation mutation may be combined with the methods of enhancing the biosynthesis enzymes.

An auxotrophic mutant strain, L-amino acid analogue-resistant strain, or metabolic regulation mutant strain with the ability to produce an L-amino acid can be obtained by subjecting a parent strain or wild-type strain to conventional mutatagenesis, such as exposure to X-rays or UV irradiation, or treatment with a mutagen such as N-methyl-N'-nitro-N-nitrosoguanidine, etc., then selecting those which exhibit autotrophy, analogue resistance, or a metabolic regulation mutation and which also have the ability to produce an L-amino acid.

Moreover, L-amino acid-producing ability can also be imparted or enhanced by enhancing an enzymatic activity by gene recombination. Examples of the method for enhancing enzymatic activity include, for example, modifying the bacterium to increase expression of a gene encoding an enzyme involved in the biosynthesis of an L-amino acid. Gene expression can also be increased by introducing an amplification plasmid prepared by introducing a DNA fragment containing the gene into an appropriate plasmid, for example, a plasmid vector containing at least a gene responsible for replication and proliferation of the plasmid in the microorganism, increasing the copy number of the gene on the chromosome by conjugation, transfer or the like, or introducing a mutation into the promoter region of the gene (refer to International Patent Publication WO95/34672).

When a target gene is introduced into the aforementioned amplification plasmid or chromosome, any promoter may be used to express the gene so long as the chosen promoter functions in the L-amino acid-producing bacterium. The promoter may be inherent to the gene, or may be a modified form. Expression of the gene can also be controlled by suitably choosing a promoter that potently functions in the L-amino acid-producing bacterium, or by approximating the −35 and −10 regions of the promoter close to the consensus sequence. The methods for enhancing expression of genes encoding the target enzymes are described in WO04/18935, European Patent Publication No. 1010755, and so forth.

Examples of methods for imparting L-amino acid-producing ability to a bacterium and bacteria imparted with an L-amino acid-producing ability will be described below.

L-Lysine-Producing Bacteria

Examples of L-lysine-producing *Escherichia* bacteria include mutants which are resistant to L-lysine analogues. L-lysine analogues inhibit growth of the bacteria, but this inhibition is fully or partially desensitized when L-lysine is present in the medium. Examples of the L-lysine analogues include, but are not limited to, oxalysine, lysine hydroxamate, S-(2-aminoethyl)-L-cysteine (AEC), γ-methyllysine, α-chlorocaprolactam, and so forth Mutants which are resistant to these lysine analogues can be obtained by subjecting the bacteria to a conventional artificial mutagenesis treatment. Specific examples of bacterial strains useful for producing L-lysine include *Escherichia coli* AJ1442 (FERM BP-1543, NRRL B-12185; see U.S. Pat. No. 4,346,170) and *Escherichia coli* VL611. In these microorganisms, feedback inhibition of aspartokinase by L-lysine is desensitized.

The WC196 strain is an L-lysine-producing *Escherichia coli* bacterium. This bacterial strain was bred by conferring AEC resistance to the W3110 strain, which was derived from *Escherichia coli* K-12. The resulting strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of L-lysine-producing bacteria and parent strains which can be used to derive L-lysine-producing bacteria also include strains in which expression is increased of one or more genes encoding an L-lysine biosynthetic enzyme. Examples of such enzymes include, but are not limited to, dihydrodipicolinate synthase (dapA), aspartonase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), diaminopimelate epimerase (dapF), tetrahydrodipicolinate succinylase (dapD), succinyl diaminopimelate deacylase (dapE), and asparlase (aspA) (EP 1253195 A). The abbreviations in parentheses are the gene names which correspond to the enzymes, and this convention is used throughout this specification. Dihydrodipicolinate reductase, diaminopimelate decarboxylase, diaminopimelate dehydrogenase, phosphoenolpyrvate carboxylase, aspartate aminotransferase, diaminopimelate epimerase, aspartate semialdehyde dehydrogenase, tetrahydrodipicolinate succinylase, and succinyl diaminopimelate deacylase are especially preferred. In addition, the chosen parent strains may overexpress the cyo gene, which is involved in energy efficiency (EP 1170376 A), the gene encoding nicotinamide nucleotide transhydrogenase (pntAB) (U.S. Pat. No. 5,830,716), the ybjE gene (WO2005/073390), or combinations thereof.

Examples of L-lysine-producing bacteria and parent strains which can be used to derive L-lysine-producing bacteria also include strains with decreased or no activity of an enzyme that catalyzes a reaction which produces a compound other than L-lysine via a biosynthetic pathway which branches off from the biosynthetic pathway of L-lysine. Examples of these enzymes include homoserine dehydrogenase, lysine decarboxylase (U.S. Pat. No. 5,827,698), and the malic enzyme (WO2005/010175).

Preferred examples of L-lysine-producing bacteria include Escherichia coli WC196ΔmezpCABD2 (WO2005/010175), WC196ΔcadAΔldc/pCABD2 (WO2006/078039), and so forth. The WC196ΔmezpCABD2 strain is obtained by introducing the plasmid pCABD2, which is disclosed in U.S. Pat. No. 6,040,160, into the WC196 strain with disrupted sfcA and b2463 genes, which encode the malic enzyme. The nucleotide sequences of the sfcA and b2463 genes and the amino acid sequences encoded by these genes are shown in SEQ ID NOS: 52 to 55.

The WC196ΔcadAΔldc/pCABD2 strain is obtained by introducing the plasmid pCABD2, which is disclosed in U.S. Pat. No. 6,040,160, into a WC196 strain with disrupted cadA and ldcC genes, which encode lysine decarboxylase. The pCABD2 plasmid contains a mutant Escherichia coli dapA gene encoding a dihydrodipicolinate synthase (DDPS) which is desensitized to feedback inhibition by L-lysine, a mutant Escherichia coli lysC gene which encodes aspartokinase III which is desensitized to feedback inhibition by L-lysine, the Escherichia coli dapB gene encoding dihydrodipicolinate reductase, and the Brevibacterium lactoformentum ddh gene encoding diaminopimelate dehydrogenase.

L-Tryptophan-Producing Bacteria

Examples of L-tryptophan-producing bacteria and parent strains which can be used to derive L-tryptophan-producing bacteria include, but are not limited to, strains belonging to the genus Escherichia, such as E. coli JP4735/pMU3028 (DSM10122) and JP6015/pMU91 (DSM10123), which is deficient in tryptophanyl-tRNA synthetase encoded by a mutant trpS gene (U.S. Pat. No. 5,756,345); E. coli SV164 (pGH5) having a serA allele encoding phosphoglycerate dehydrogenase not subject to feedback inhibition by serine and a trpE allele encoding anthranilate synthase not subject to feedback inhibition by tryptophan (U.S. Pat. No. 6,180,373); E. coli AGX17 (pGX44) (NRRL B-12263) and AGX6 (pGX50) aroP (NRRL B-12264) deficient in the enzyme tryptophanase (U.S. Pat. No. 4,371,614); E. coli AGX17/pGX50, pACKG4-pps with enhanced phosphoenolpyruvate-producing ability (WO97/08333, U.S. Pat. No. 6,319,696), and so forth. L-tryptophan-producing Escherichia bacteria with enhanced activity of the protein encoded by the yedA or yddG genes may also be used (U.S. Published Patent Applications 2003/0148473 A1 and 2003/0157667 A1).

Examples of L-tryptophan-producing bacteria and parent strains which can be used to derive L-tryptophan-producing bacteria also include strains with enhanced activity of one or more enzymes such as anthranilate synthase (trpE), phosphoglycerate dehydrogenase (serA), 3-deoxy-D-arabinoheptulosonate-7-phosphate syntaase (aroG), 3-dehydroquinate synthase (aroB), shikimate dehydrogenase (aroE), shikimate kinase (aroL), 5-enolpyruvylshikimate-3-phosphate synthase (aroA), chorismate synthase (aroC), prephenate dehydratase, chorismate mutase, and tryptophan synthase (trpAB). Prephenate dehydratase and chorismate mutase are encoded by the pheA gene as a bifunctional enzyme (CM-PD). Phosphoglycerate dehydrogenase, 3-deoxy-D-arabinoheptulosonate-7-phosphate synthase, 3-dehydroquinate synthase, shikimate dehydratase, shikimate kinase, 5-enolpyruvylshikimate-3-phosphate synthase, chorismate synthase, prephenate dehydratase, chorismate mutase-prephenate dehydratase are especially preferred. The anthranilate synthase and phosphoglycerate dehydrogenase are both subject to feedback inhibition by L-tryptophan and L-serine, and therefore a mutation desensitizing the feedback inhibition may be introduced into these enzymes. Specific examples of strains having such a mutation include E. coli SV164 which harbors desensitized anthranilate synthase, and a transformant strain obtained by introducing pGH5 (WO 94/08031) into E. coli SV164, which contains a mutant serA gene encoding feedback inhibition-desensitized phosphoglycerate dehydrogenase.

Examples of L-tryptophan-producing bacteria and parent strains which can be used to derive L-tryptophan-producing bacteria also include strains transformed with the tryptophan operon which contains a gene encoding desensitized anthranilate synthase (JP 57-71397 A, JP 62-244382 A, U.S. Pat. No. 4,371,614). Moreover, L-tryptophan-producing ability may be imparted by enhancing the expression of the gene which encodes tryptophan synthase, which is part of the tryptophan operon (trpBA). The tryptophan synthase consists of α and β subunits which are encoded by trpA and trpB, respectively. In addition, L-tryptophan-producing ability may be improved by enhancing expression of the isocitrate lyase-malate synthase operon (WO2005/103275).

L-Phenylalanine-Producing Bacteria

Examples of L-phenylalanine-producing bacteria and parent strains which can be used to derive L-phenylalanine-producing bacteria include, but are not limited to, strains belonging to the genus Escherichia, such as E. coli AJ12739 (tyrA::Tn10, tyrR) (VKPM B-8197) (WO03/044191), E. coli HW1089 (ATCC 55371) harboring the pheA34 gene encoding chorismate mutase-prephenate dehydratase desensitized to the feedback inhibition (U.S. Pat. No. 5,354,672), E. coli MWEC101-b (KR8903681), *E. coli* NRRL B-12141, NRRL B-12145, NRRL B-12146, and NRRL B-12147 (U.S. Pat. No. 4,407,952). Also, as a parent strain, *E. coli* K-12 [W3110 (tyrA)/pPHAB (FERM BP-3566) having a gene encoding chorismate mutase-prephenate dehydratase desensitized to feedback inhibition, *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB], also called AJ12604 (FERM BP-3579) may be used (EP 488-424 B1). Furthermore, L-phenylalanine-producing *Escherichia* bacteria with enhanced activity of the protein encoded by the yedA or yddG genes may also be used (U.S. Published Patent Applications 2003/0148473 A1 and 2003/0157667 A1, WO03/044192).

L-Valine-Producing Bacteria

Examples of L-valine-producing bacteria and parent strains which can be used to derive L-valine-producing bacteria include, but are not limited to, strains which have been modified to overexpress the ilvGMEDA operon (U.S. Pat. No. 5,998,178). The region in the ilvGMEDA operon which is required for attenuation can be removed so that expression of the operon is not attenuated by the L-valine that is produced. Furthermore, the ilvA gene in the operon can be disrupted so that threonine deaminase activity is decreased.

Examples of L-valine-producing bacteria and parent strains which can be used to derive L-valine-producing bacteria also include strains with amino-acyl t-RNA synthetase mutants (U.S. Pat. No. 5,658,766). For example, *E. coli* VL1970, which has a mutation in the ileS gene, which encodes isoleucine tRNA synthetase, can be used. *E. coli* VL1970 was deposited at the Russian National Collection of Industrial Microorganisms (VKPM) (1 Dorozhny proezd., 1 Moscow 117545, Russia) on Jun. 24, 1988 under accession number VKPM B-4411.

Furthermore, mutants requiring lipoic acid for growth and/or lacking $H^+$-ATPase can also be used as parent strains (WO96/06926, U.S. Pat. No. 5,888,783).

L-Leucine-Producing Bacteria

Examples of L-leucine-producing bacteria and parent strains which can be used to derive L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogues including β-2-thienylalanine, 3-hydroxyleucine, 4-azaleucine and 5,5,5-trifluoroleucine (JP 62-34397 B and JP 8-70879 A); *E. coli* strains obtained by the genetic engineering method described in WO96/06926; and *E. coli* H-9068 (JP 8-70879 A).

The bacterium may be improved by enhancing the expression of one or more genes which encode proteins involved in L-leucine biosynthesis. Examples of such genes include genes of the leuABCD operon, such as a mutant leuA gene encoding isopropylmalate synthase which is not subject to feedback inhibition by L-leucine (U.S. Pat. No. 6,403,342). In addition, the bacterium may be improved by enhancing the expression of one or more genes encoding proteins which promote secretion of L-amino acids from the bacterial cell. Examples of such genes include b2682 and b2683 (ygaZH genes) (EP 1239041 A2).

L-Isoleucine-Producing Bacteria

Examples of L-isoleucine-producing bacteria and parent strains which can be used to derive L-isoleucine-producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxy acid synthase, can also be used as parent strains (JP 2-458 A, FR 0356739, and U.S. Pat. No. 5,998,178).

L-Serine-Producing Bacteria

Examples of L-serine-producing bacteria and parent strains which can be used to derive L-serine-producing bacteria include *Escherichia coli* which are desensitized to feedback inhibition of 3-phosphoglycerate dehydrogenase by serine (Japanese Patent No. 2584409, U.S. Pat. No. 5,618,716). Moreover, coryneform bacteria which are able to produce L-serine and have increased activity of at least one of phosphoserine phosphatase and phosphoserine transaminase, coryneform bacteria which cannot decompose L-serine (JP 11-253187 A, U.S. Pat. No. 6,037,154), and coryneform bacteria which is resistant to azaserine or β-(2-thienyl)-DL-alanine and is able to produce L-serine (JP 11-266881 A, U.S. Pat. No. 6,258,573) can also be used.

When the aforementioned L-amino acid-producing bacteria are bred by gene recombination, the chosen genes are not limited to genes having the genetic information described above or genes having known sequences, but genes having conservative mutations such as homologues or artificially modified genes can also be used, so long as the functions of the encoded proteins are not degraded. That is, the chosen genes may encode a known amino acid sequence including substitution, deletion, insertion, addition or the like of one or several amino acid residues at one or several positions. As for the "conservative mutation", the descriptions concerning pyruvate synthase etc. described below are also applied to the aforementioned genes.

<1-2> Enhancement of Pyruvate Synthase or pyruvate: $NADP^+$ Oxidoreductase Activity The microorganism having an L-amino acid-producing ability is modified so that an activity of pyruvate synthase or pyruvate:$NADP^+$ oxidoreductase is increased. The activity of the pyruvate synthase orpyruvate:$NADP^+$ oxidoreductase activity is increased so that it is higher as compared to that of the parent strain, for example, a wild-type strain or a non-modified strain. In addition, this is true when the pyruvate synthase activity is not native to the microorganism, for example, the pyruvate synthase or pyruvate:$NADP^+$ oxidoreductase activity of the microorganism, which has been modified to have that enzymatic activity, is increased as compared with a non-modified strain.

The bacterium may be modified first to increase the enzymatic activity of pyruvate synthase orpyruvate:$NADP^+$ oxidoreductase, and then imparted with an L-amino acid-producing ability. In addition, the activity of pyruvate synthase orpyruvate:$NADP^+$ oxidoreductase can be increased by increasing the expression of a gene as described above. That is, enzyme activity may be increased by increasing expression of the endogenous pyruvate synthase or pyruvate: $NADP^+$ oxidoreductase genes by modifying the expression control regions such as the promoter or the like, or by enhancing expression of an exogenous pyruvate synthase gene or pyruvate:$NADP^+$ oxidoreductase gene by introducing a plasmid containing the pyruvate synthase or pyruvate:$NADP^+$ oxidoreductase gene into the bacterium, introducing these genes into the chromosome of the bacterium, or the like.

Pyruvate synthase catalyzes the following reaction, which generates pyruvic acid from acetyl-CoA and $CO_2$ in the presence of an electron donor such as ferredoxin and flavodoxin (EC 1.2.7.1). Pyruvate synthase may be abbreviated as "PS", and may be also be called pyruvate oxidoreductase, pyruvate ferredoxin oxidoreductase, pyruvate flavodoxin oxidoreductase, or pyruvate oxidoreductase. As the electron donor, ferredoxin or flavodoxin can be used.

Reduced ferredoxin+acetyl-CoA+$CO_2$=oxidized ferredoxin+pyruvic acid+CoA

Enhancement of the pyruvate synthase activity can be confirmed by preparing crude enzyme solutions and measuring the pyruvate synthase activity in both the microorganism before making the modification to enhance activity, and after making the modification. The activity of pyruvate synthase can be measured by, for example, the method of Yoon et al. (Yoon, K. S. Ishii, M., Kodama, T., and Igarashi, Y. 1997. Arch. Microbiol. 167:275-279, 1997). For example, pyruvic acid is added to a reaction mixture containing oxidized methylviologen which acts as an electron acceptor, CoA, and crude enzyme solution, and spectroscopically measuring the amount of reduced methylviologen, which increases due to the decarboxylation of pyruvic acid. One unit (U) of the enzymatic activity is defined as the activity of reducing 1 μmol of methylviologen per 1 minute. When the parent strain has pyruvate synthase activity, the activity desirably increases, for example, preferably 1.5 times or more, more preferably 2 times or more, still more preferably 3 times or more, compared with that of the parent strain. When the parent strain does not have pyruvate synthase activity, although it is sufficient that pyruvate synthase is produced by the introduction of the pyruvate synthase gene, the activity is preferably enhanced to such an extent that the enzymatic activity can be measured, and the activity is preferably 0.001 U/mg (cell protein) or higher, more preferably 0.005 U/mg or higher, still more preferably 0.01 U/mg or higher. Pyruvate synthase is sensitive to oxygen, and activity expression and measurement are often generally difficult (Buckel, W. and Golding, B. T., 2006, Ann. Rev. of Microbiol., 60:2749). Therefore, as described in the examples, the enzymatic activity is measured preferably under reduced oxygen concentration in the reaction vessel.

The gene encoding pyruvate synthase may be derived from, or native to, bacteria with the reductive TCA cycle, and includes pyruvate synthase genes from *Chlorobium tepidum* and *Hydrogenobacter thermophilus*.

Specific examples include the pyruvate synthase gene having the nucleotide sequence located at nucleotide numbers from 1534432 to 1537989 of the genome sequence of *Chlorobium tepidum* (Genbank Accession No. NC_002932) and shown in SEQ ID NO: 1. The amino acid sequence encoded by this gene is shown in SEQ ID NO: 2 (Genbank Accession No. AAC76906). Furthermore, the pyruvate synthase from *Hydrogenobacter thermophilus* forms a complex of four subunits, the δ-subunit (Genbank Accession No. BAA95604), α-subunit (Genbank Accession No. BAA95605), β-subunit (Genbank Accession No. BAA95606), and γ-subunit (Genbank Accession No. BAA95607) (Ikeda, T. Ochiai, T., Morita, S., Nishiyama, A., Yamada, E., Arai, H., Ishii, M. and Igarashi, Y. 2006, Biochem. Biophys. Res. Commun., 340: 76-82). The pyruvate synthase gene may also include the four genes HP108, HP109, HP1110, and HP1111, located at nucleotide numbers from 1170138 to 1173296 in the genome sequence of *Helicobacter pylori* (GenBank Accession No. NC 000915), and the pyruvate synthase gene encoded by the four genes SSO1208, SSO7412, SSO1207, and SSO1206, identified by nucleotide numbers from 1047593 to 1044711 in the genome sequence of *Sulfolobus solfataricus* (GenBank Accession No. NC 002754). Furthermore, the pyruvate synthase gene may be cloned from *Chlorobium, Desulfobacter, Aquifex, Hydrogenobacter, Thermoproteus, Pyrobaculum* bacteria, or the like on the basis of homology to the genes exemplified above.

The *Escherichia coli* ydbK gene (b1378), which is shown in SEQ ID NO: 3, is located at nucleotide numbers from 1435284 to 1438808 in the genome sequence of the K-12 strain (GenBank Accession No. U00096). This gene is predicted to encode pyruvate flavodoxin oxidoreductase, that is, pyruvate synthase, on the basis of homology of the sequences. The amino acid sequence encoded by this gene is shown in SEQ ID NO: 4 (GenBank Accession No. AAC76906). As demonstrated in the example section, it was verified that this gene product has pyruvate synthase activity, and enhancing expression of this gene improves the ability to produce an L-amino acid.

Pyruvate:$NADP^+$ oxidoreductase catalyzes the following reaction, which generates pyruvic acid from acetyl CoA and $CO_2$, in the presence of an electron donor such as NADPH or NADH (EC 1.2.1.15). Pyruvate:$NADP^+$ oxidoreductase may be abbreviated as "PNO", and may also be called pyruvate dehydrogenase. However, pyruvate dehydrogenase activity is the activity of catalyzing the oxidative decarboxylation of pyruvic acid to generate acetyl-CoA, as described later, and pyruvate dehydrogenase (PDH) which catalyses this reaction is different from pyruvate:$NADP^+$ oxidoreductase. Pyruvate:$NADP^+$ oxidoreductase can use NADPH or NADH as the electron donor.

NADPH+acetyl-CoA+$CO_2$=$NADP^+$+pyruvic acid+CoA

Enhancement of the pyruvate:$NADP^+$ oxidoreductase activity can be confirmed by preparing crude enzyme solutions and measuring the pyruvate:$NADP^+$ oxidoreductase activity in both the microorganism before making the modification to enhance activity, and after making the modification. The activity of pyruvate:$NADP^+$ oxidoreductase can be measured by, for example, the method of Inui et al. (Inui, H., Ono, K., Miyatake, K, Nakano, Y., and Kitaoka, S., 1987, J. Biol. Chem., 262:9130-9135). For example, pyruvic acid is added to a reaction mixture containing oxidized methylviologen which acts as an electron acceptor, CoA, and crude enzyme solution, and spectroscopically measuring the amount of reduced methylviologen, which increases due to the decarboxylation of pyruvic acid. One unit (U) of the enzymatic activity is defined as the activity of reducing 1 μmol of methylviologen per 1 minute. When the parent strain has pyruvate:$NADP^+$ oxidoreductase activity, the activity increases, for example, preferably 1.5 times or more, more preferably 2 times or more, still more preferably 3 times or more, as compared to that of the parent strain. When the parent strain does not have pyruvate:$NADP^+$ oxidoreductase activity, although it is sufficient that pyruvate:$NADP^+$ oxidoreductase is produced by the introduction of the pyruvate:$NADP^+$ oxidoreductase gene, the activity is preferably enhanced to such an extent that the enzymatic activity can be measured, and the activity is preferably 0.001 U/mg (cell protein) or higher, more preferably 0.005 U/mg or higher, still more preferably 0.01 U/mg or higher. Pyruvate:$NADP^+$ oxidoreductase is sensitive to oxygen, and activity expression and measurement are often generally difficult (Inui, H., Ono, K., Miyatake, K, Nakano, Y., and Kitaoka, S., 1987, J. Biol. Chem., 262: 9130-9135; Rotte, C., Stejskal, F., Zhu, G., Keithly, J. S., and Martin, W., 2001, Mol. Biol. Evol., 18:710-720). When the activity cannot be measured due to inactivation or the like, it is still possible to confirm expression of the protein by Western blotting or the like, as described in the examples section.

The gene encoding pyruvate:$NADP^+$ oxidoreductase may be derived from, or native to, *Euglena gracilis*, which is a photosynthetic eukaryotic microorganism and is also classified into protozoans (Nakazawa, M., Inui, H. Yamaji R., Yamamoto, T., Takenaka, S., Ueda, M., Nakano, Y., Miyatake, K, 2000, FEBS Let, 479:155-156), and the protist *Cryptosporidium parvum* (Rotte, C., Stejskal, F., Zhu, G., Keithly, J. S., and Martin, W., 2001, Mol. Biol. Evol., 18:710-720). Furthermore, it is known that a homologous gene also exists in *Tharassiosira pseudonana* which belongs to *Bacillariophyta* (Ctrnacta, V., Ault, J. G., Stejskal, F., and Keithly, J. S., 2006, J. Eukaryot Microbiol., 53:225-231).

Specifically, the pyruvate:NADP$^+$ oxidoreductase gene from *Euglena gracilis* has the nucleotide sequence shown in SEQ ID NO: 5 (GenBank Accession No. AB021127). The amino acid sequence encoded by this gene is shown in SEQ ID NO: 6 (GenBank Accession No. BAB12024).

The microorganism may be modified so that the pyruvate synthase activity is increased by increasing the activity of recycling the oxidized electron donor to a reduced electron donor, which is requiled for pyruvate synthase activity, as compared to a parent strain, for example, a wild-type strain or a non-modified strain. An example of the activity for recycling the oxidized electron donor to a reduced electron donor is ferredoxin NADP$^+$ reductase activity. Furthermore, the microorganism may be modified so that the activity of pyruvate synthase is increased, in addition to enhancing the electron donor recycling activity. The gene encoding the electron donor recycling activity may be native to the parent strain, or may be introduced into the parent strain to impart the activity, and the ability to produce an L-amino acid is improved.

The ferredoxin NADP$^+$ reductase is an enzyme that reversibly catalyzes the following reaction (EC 1.18.1.2):

Reduced ferredoxin+NADP$^+$=Oxidized ferredoxin+NADPH+H$^+$

This reaction is reversible, and can generate the reduced ferredoxin in the presence NADPH and the oxidized ferredoxin. Ferredoxin can be replaced with flavodoxin, and the enzyme is a functional equivalent to flavodoxin NADP$^+$ reductase. Ferredoxin NADP$^+$ reductase has been confirmed to be present in a wide variety of organisms ranging from microorganisms to higher organisms (refer to Canillo, N. and Ceccarelli, E. A., 2004, Eur. J. Biochem., 270:1900-1915; Ceccarelli, E. A. Arakaki, A. K, Cortez, N., and Canillo, N. 2004, Biochim. Biophys. Acta., 1698:155-165), and it is also known as ferredoxin NADP$^+$ oxidoreductase or NADPH-ferredoxin oxidoreductase.

Enhancement of the ferredoxin NADP$^+$ reductase activity can be confirmed by preparing crude enzyme solutions and measuring the ferredoxin NADP$^+$ reductase activity in both the microorganism before making the modification to enhance activity, and after making the modification. The activity of ferredoxin NADP$^+$ reductase can be measured by, for example, the method of Blaschkowski et al (Blaschkowski, H. P., Neuer, G., Ludwig-Festl, M., and Knappe, J. 1989, Eur. J. Biochem., 123:563-569). For example, the activity can be measured by using ferredoxin as a substrate to spectroscopically measure the decrease of the amount of NADPH. One unit (U) of the enzymatic activity is defined as the activity of oxidizing 1 µmol of NADPH per 1 minute. When the parent strain has ferredoxin NADP$^+$ reductase activity, and the activity of the parent strain is sufficiently high, it is not necessary to enhance the activity. However, the enzymatic activity is desirably increased preferably 1.5 times or more, more preferably 2 times or more, still more preferably 3 times or more, compared with that of the parent strain.

Genes encoding ferredoxin NADP$^+$ reductase are found in many biological species, and any that have activity in the chosen L-amino acid producing strain can be used. In *Escherichia coli*, the fpr gene has been identified as the gene encoding flavodoxin NADP$^+$ reductase (Bianchi, V. Reichard, P., Eliasson, R, Pontis, E., Krook M., Jomvall, H., and Haggard-Ljungquist, E. 1993, 175:1590-1595). Moreover, it is known that, in *Pseudomonas putida*, the NADPH-putidaredoxin reductase gene and the putidaredoxin gene are present as an operon (Koga, H., Yamaguchi, E., Matsunaga, K, Aramaki, H., and Horiuchi, T. 19089, J. Biochem. (Tokyo), 106: 831-836).

The flavodoxin NADP$^+$ reductase gene from *Escherichia coli* (fpr gene) is located at nucleotide numbers from 4111749 to 4112495 (complementary strand) in the genome sequence of the *Escherichia coli* K-12 strain (Genbank Accession No. U00096) and is shown in SEQ ID NO: 7. The amino acid sequence of Fpr is shown in SEQ ID NO: 8 (Genbank Accession No. AAC76906). Moreover, the ferredoxin NADP$^+$ reductase gene (Genbank Accession No. BAB99777) is found at the nucleotide numbers from 2526234 to 2527211 of the genome sequence of *Corynebacterium glutamicum* (Genbank Accession No. BA00036).

The pyruvate synthase activity requires the presence of ferredoxin or flavodoxin, which acts as an electron donor. Therefore, the microorganism may be modified so that the activity of pyruvate synthase is increased by improving the production of ferredoxin or flavodoxin.

Moreover, the microorganism may also be modified to improve the production of ferredoxin or flavodoxin, in addition to being modified to enhance pyruvate synthase activity alone, or enhance both the activities of flavodoxin NADP$^+$ reductase and pyruvate synthase.

"Ferredoxin" refers to a protein containing nonheme iron atoms (Fe) and sulfur atoms bound with an iron-sulfur cluster called 4Fe-4S, 3Fe-4S or 2Fe-2S, and which functions as a one-electron carrier. "Flavodoxin" refers to a protein containing FMN (flavin-mononucleotide) as a prosthetic group and which functions as a one- or two-electron carrier. Ferredoxin and flavodoxin are described in McLean et al. (McLean K. J., Sabri, M., Marshall, K. R, Lawson, R. J., Lewis, D. G., Clift, D., Balding, P. R., Dunford, A. J., Warman, A. J., McVey, J. P., Quinn, A. M., Sutcliffe, M. J., Scrutton, N. S., and Munro, A. W. 2005, Biochem. Soc. Trans., 33:796-801).

Ferredoxin or flavodoxin may be native to the parent strains which are used to derive the modified microorganism described herein, or a gene encoding ferredoxin or flavodoxin may be introduced into the parent strains to impart the activity to produce ferredoxin or flavodoxin, and to improve L-glutamic producing ability.

An improvement in the ability to produce ferredoxin or flavodoxin as compared with the parent strain, such as a wild-type or non-modified strain, can be confirmed by, for example, comparing the amount of mRNA for ferredoxin or flavodoxin with that in a wild-type strain or non-modified strain. The expression amount can be confirmed by, for example, Northern hybridization and RT-PCR (Sambrook J., Fritsch, E. F., and Maniatis, T. 1989, Molecular Cloning A Laboratory Manual/Second Edition, Cold Spring Harbor Laboratory Press, New York). The degree of the increase of the expression is not particularly limited so long as it is increased compared with that of a wild-type strain or non-modified strain. However, it is increased, for example, 1.5 times or more, preferably 2 times or more, more preferably 3 times or more, compared with that of a wild-type strain or non-modified strain.

Whether the ability to produce ferredoxin or flavodoxin is improved as compared with a parent strain, for example, a wild-type strain or a non-modified strain, can be detected by SDS-PAGE, two-dimensional electrophoresis, or Western blotting using antibodies (Sambrook J., Fritsch, E. F., and Maniatis, T. 1989, Molecular Cloning A Laboratory Manual/ Second Edition, Cold Spring Harbor Laboratory Press, New York). The degree of improvement is not particularly limited so long as it is increased as compared with that of a wild-type strain or non-modified strain. However, it is increased, for example, 1.5 times or more, preferably 2 times or more, more preferably 3 times or more, compared with that of a wild-type strain or non-modified strain.

The activities of ferredoxin and flavodoxin can be measured by adding them to a suitable oxidation-reduction reaction system. For example, reducing ferredoxin with ferredoxin NADP$^+$ reductase and quantifying the reduction of cytochrome C by the reduced ferredoxin is disclosed by Boyer et al. (Boyer, M. E. et al., 2006, Biotechnol. Bioeng., 94:128-138). Furthermore, the activity of flavodoxin can be measured by the same method, but using flavodoxin NADP$^+$ reductase.

Genes encoding ferredoxin or flavodoxin are known from many species, and any of these can be used so long as the ferredoxin or flavodoxin encoded by the genes can be utilized by pyruvate synthase and an electron donor recycling system. For example, in *Escherichia coli*, the fdx gene encodes ferredoxin which has a 2Fe-2S cluster (Ta, D. T. and Vickery, L. E., 1992, J. Biol. Chem., 267:11120-11125), and the yfhL gene encodes ferredoxin which has a 4Fe-4S cluster. Furthermore, the fldA gene (Osborne C. et al., 1991, J. Bacteriol., 173: 1729-1737) and the fldB gene (Gaudu, P. and Weiss, B., 2000, J. Bacteriol., 182:1788-1793) are known to encode flavodoxin. In the genome sequence of *Corynebacterium glutamicum* (Genbank Accession No. BA00036), multiple ferredoxin genes were found at nucleotide numbers from 562643 to 562963 (fdx—Genbank Accession No. BAB97942), and nucleotide numbers from 1148953 to 1149270 (fer—Genbank Accession No. BAB98495). Furthermore, in *Chlorobium tepidum*, many ferredoxin genes have been identified, for example, ferredoxin I and ferredoxin II are of the 4Fe-4S type, which acts as the electron acceptor for pyruvate synthase (Yoon, K. S., Bobst, C., Hemann, C. F., Hille, R, and Tabita, F. R 2001, J. Biol. Chem., 276:44027-44036). Ferredoxin or flavodoxin native to or derived from bacteria having the reductive TCA cycle, such as the ferredoxin gene of *Hydrogenobacter thermophilus*, can also be used.

The ferredoxin gene of *Escherichia coli* includes the fdx gene at nucleotide numbers from 2654770 to 2655105 (complementary strand) in the genome sequence of the *Escherichia coli* K-12 strain (Genbank Accession No. U00096) and shown in SEQ ID NO: 9, and the yfhL gene at nucleotide numbers from 2697685 to 2697945 also from K-12, and shown in SEQ ID NO: 11. The amino acid sequences of Fdx and YfhL are shown in SEQ ID NOS: 10 and 12 (Genbank Accession Nos. AAC75578 and AAC75615, respectively). The flavodoxin gene of *Escherichia coli* includes the gene at nucleotide numbers from 710688 to 710158 (complementary strand) in the genome sequence of the *Escherichia coli* K-12 strain (Genbank Accession No. U00096) and shown in SEQ ID NO: 13, and the fldB gene at nucleotide numbers from 3037877 to 3038398 also from K-12, and shown in SEQ ID NO: 15. The amino acid sequences encoded by the fldA gene and the fldB gene are shown in SEQ ID NOS: 14 and 16 (Genbank Accession Nos. AAC73778 and AAC75933, respectively).

The ferredoxin gene of *Chlorobium tepidum* includes the ferredoxin I gene at nucleotide numbers from 1184078 to 1184266 in the genome sequence of *Chlorobium tepidum* (Genbank Accession No. NC_002932) and shown in SEQ ID NO: 17, and the ferredoxin II gene at nucleotide numbers from 1184476 to 1184664 also from *Chlorobium tepidum* and shown in SEQ ID NO: 19. The amino acid sequences of ferredoxin I and ferredoxin II are shown in SEQ ID NOS: 18 and 20 (Genbank Accession Nos. AAM72491 and AAM72490, respectively). Examples further include the ferredoxin gene of *Hydrogenobacter thermophilus* (Genbank Accession No. BAE02673) and the ferredoxin gene of *Sulfolobus solfataricus*, which is present at nucleotide numbers from 2345414 to 2345728 in the genome of *Sulfolobus solfataricus*. Furthermore, the gene may be those cloned from *Chlorobium, Desulfobacter, Aquifex, Hydrogenobacter, Thermoproteus, Pyrobaculum* bacteria, or the like on the basis of homology to the genes exemplified above, or those cloned from γ-proteobacteria such as those of the genus *Enterobacter, Klebsiella, Serratia, Erwinia,* and *Yersinia*, coryneform bacteria such as *Corynebacterium glutamicum* and *Brevibacterium lactofermentum, Pseudomonas* bacteria such as *Pseudomonas aeruginosa, Mycobacterium* bacteria such as *Mycobacterium tuberculosis*, and so forth.

Any of the genes described herein may have conservative mutations, and may be homologues or artificially modified genes so long as the functions of the encoded proteins are not degraded. That is, the genes described herein may encode a conservative variant of the proteins having amino acid sequences of the known proteins or wild-type proteins, and may include one or more substitutions, deletions, insertions, or additions of one or several amino acid residues at one or several positions. Although the number of the "one or several" amino acid residues may differ depending on their position in the three-dimensional structure or the types of amino acid residues of the proteins, it is preferably 1 to 20, more preferably 1 to 10, particularly preferably 1 to 5.

These substitutions are preferably conservative substitutions that are neutral mutations so to preserve the function of the protein. A conservative mutation is a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group.

Specific examples of conservative substitutions include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The above-mentioned amino acid substitution, deletion, insertion, addition, inversion etc. may be the result of a naturally-occurring mutation or variation due to an individual difference, or a difference of species of a bacterium.

Furthermore, a gene may be used which has codon substitutions that can be easily used in the chosen host into which the gene is introduced. Similarly, so long as the gene maintains its function, it may be extended or shortened at either the N-terminus and/or C-terminus by, for example, 50 or less, preferably 20 or less, more preferably 10 or less, particularly preferably 5 or less, of the number of amino acid residues.

A gene encoding a conservative variant can be obtained by, for example, modifying the nucleotide sequence by site-specific mutagenesis so that the encoded protein includes substitutions, deletions, insertions, or additions of amino acid residues at specific sites. Furthermore, it can also be obtained by the conventionally known mutagenesis techniques, such as by treating the gene with hydroxylamine or the like in vitro and irradiating the microorganism containing the gene with ultraviolet light, or treating the microorganism with a known mutagen such as N-methyl-N'-nitro-N-nitrosoguanidine (NTG) or ethyl methanesulfonate (EMS). Moreover, the substitutions, deletions, insertions, additions, inversions etc. of amino acid residues as described above include those due to a naturally occurring mutation or variation based on the difference of individuals or species of the microorganism containing the gene. Whether the gene(s) encodes pyruvate synthase, ferredoxin-NADP$^+$ reductase, ferredoxin, or flavodoxin can be confirmed by, for example, introducing each gene into a microorganism, and measuring the activity of each protein.

The gene may be a DNA which hybridizes with a DNA having any one of the aforementioned nucleotide sequences, or a probe prepared from a DNA which has anyone of these nucleotide sequences, under stringent conditions and which encodes pyruvate synthase, ferredoxin-NADP$^+$ reductase, ferredoxin, or flavodoxin.

The term "stringent conditions" refers to conditions where a so-called specific hybrid is formed and a non-specific hybrid is not formed. Examples thereof include conditions where DNAs having high homology, for example, at least 70%, preferably 80%, more preferably 90%, and further more preferably 95% homology, hybridize with each other and DNAs having homology less than the value do not hybridize with each other; and specifically include conditions corresponding to a salt concentration and temperature of washing which are typical of Southern hybridization, e.g., washing at 60° C., 1×SSC, 0.1% SDS, preferably 60° C., 0.1×SSC, 0.1% SDS, more preferably 68° C., 0.1×SSC, 0.1% SDS, once or preferably twice or three times.

The probe may have a partial sequence of the gene. Such a probe can be prepared by PCR using oligonucleotides prepared based on the nucleotide sequence of each gene as primers according to a method well known to a person skilled in the art, and a DNA fragment containing each gene as the template. When a DNA fragment of a length of about 300 bp is used as the probe, the conditions of washing after hybridization can be, for example, 50° C., 2×SSC, and 0.1% SDS.

The aforementioned descriptions concerning the conservative variant is also applied to the enzymes and genes described above which are used to impart L-amino acid-producing ability.

The modification for enhancing expression of the gene can be performed in the same manner as that described to enhance the expression of a target gene which is used to impart the L-amino acid-producing ability. The gene can be obtained by PCR using the chromosomal DNA of the microorganism as the template.

For example, the pyruvate synthase gene of *Chlorobium tepidum* can be obtained by PCR (polymerase chain reaction) (see White, T. J., Arnheim, N., and Erlich, H. A. 1989, Trends Genet., 5:185-189) using primers prepared on the basis of the nucleotide sequence of SEQ ID NO: 1, for example, the primers shown in SEQ ID NOS: 35 and 36, and using the chromosomal DNA of *Chlorobium tepidum* as the template.

The pyruvate synthase gene of *Escherichia coli* can be obtained by PCR using primers prepared on the basis of the nucleotide sequence of SEQ ID NO: 3, for example, the primers shown in SEQ ID NOS: 38 and 39, and the chromosomal DNA of *Escherichia coli* as the template.

The NADP$^+$ oxidoreductase gene of *Euglena gracilis* can be obtained by PCR using primers prepared on the basis of the nucleotide sequence of SEQ ID NO: 5, for example, the primers shown in SEQ ID NOS: 40 and 41, and the chromosomal DNA of *Euglena gracilis* as the template.

The flavodoxin NADP$^+$ reductase gene of *Escherichia coli* can be obtained by PCR using primers prepared on the basis of the nucleotide sequence of SEQ ID NO: 7, for example, the primers shown in SEQ ID NOS: 42 and 43, and the chromosomal DNA of *Escherichia coli* as the template.

The ferredoxin gene fdx of *Escherichia coli* can be obtained by PCR using primers prepared on the basis of the nucleotide sequence of SEQ ID NO: 9, for example, the primers shown in SEQ ID NOS: 44 and 45, and the chromosomal DNA of *Escherichia coli* as the template.

The flavodoxin gene fldA of *Escherichia coli* can be obtained by PCR using primers prepared on the basis of the nucleotide sequence of SEQ ID NO: 13, and the flavodoxin gene fldB of *Escherichia coli* can be obtained by PCR using primers prepared on the basis of the nucleotide sequence of SEQ ID NO: 15, and the chromosomal DNA of *Escherichia coli* as the template, respectively.

Furthermore, the ferredoxin I gene of *Chlorobium tepidum* can be obtained by PCR using primers prepared on the basis of the nucleotide sequence of SEQ ID NO: 17, and the ferredoxin II gene of *Chlorobium tepidum* can be obtained by PCR using primers prepared on the basis of the nucleotide sequence of SEQ ID NO: 19, with using the chromosomal DNA of *Chlorobium tepidum* as the template in both cases.

Genes derived from other microorganisms can also be obtained from the chromosomal DNA or a chromosomal DNA library from the chosen microorganism by PCR using, as primers, oligonucleotides prepared based on the sequences of the aforementioned gene or sequences of genes or proteins known in the chosen microorganism; or hybridization using an oligonucleotide prepared based on such sequence as mentioned above as a probe. A chromosomal DNA can be prepared from a microorganism that serves as a DNA donor by the method of Saito and Miura (Saito H. and Miura K, 1963, Biochem. Biophys. Acta, 72:619-629, Experiment Manual for Biotechnology, edited by The Society for Biotechnology, Japan, p 97-98, Baifukan Co., Ltd., 1992) or the like.

The expression of the gene and genes of L-amino acid synthesis systems can be increased by increasing the copy number of the gene by transformation or homologous recombination, or modifying an expression control sequence of the gene as described above. Furthermore, the expression of the gene can also be increased by amplifying an activator which increases expression of the gene, and/or by eliminating or attenuating a regulator which reduces expression of the gene.

Methods for increasing gene expression will be explained below.

To increase the copy number of a target gene, for example, the gene can be cloned on an appropriate vector and then used to transform a host microorganism.

The vector used for transformation may be a plasmid which autonomously replicates in the host microorganism. Examples of a plasmid which is able to autonomously replicate in *Enterobacteriaceae* include pUC19, pUC18, pBR322, RSF1010, pHSG299, pHSG298, pHSG399, pHSG398, pSTV28, pSTV29 (pHSG and pSTV vectors are available from Takara Bio Inc.), pMW119, pMW118, pMW219, pMW218 (pMW vectors are available from Nippon Gene Co., Ltd.), and so forth. Furthermore, plasmids for coryneform bacteria include pAM330 (Japanese Patent Laid-open No. 58-67699), pHM1519 (Japanese Patent Laid-open No. 58-77895), pSFK6 (Japanese Patent Laid-open No. 2000-

262288), pVK7 (USP2003-0175912A), pAJ655, pAJ611, pAJ1844 (Japanese Patent Laid-open No. 58-192900), pCG1 (Japanese Patent Laid-open No. 57-134500), pCG2 (Japanese Patent Laid-open No. 58-35197), pCG4, pCG11 (Japanese Patent Laid-open No. 57-183799), pHK4 (Japanese Patent Laid-open No. 5-7491), and so forth. Moreover, a DNA fragment which is able to impart the ability to autonomously replicate to a plasmid in a coryneform bacterium can be cut from these vectors and inserted into the aforementioned vectors for Escherichia coli, and then can be used as a so-called shuttle vector which is able to autonomously replicate in both Escherichia coli and coryneform bacteria. In addition, a phage DNA may also be used as the vector instead of a plasmid.

Examples of transformation methods include treating recipient cells with calcium chloride so to increase permeability of the DNA, which has been reported for Escherichia coli K-12 (Mandel, M. and Higa, A., 1970, J. Mol. Biol., 53:159-162), and preparing competent cells from cells which are at the growth phase, followed by transformation with DNA, which has been reported for Bacillus subtilis (Duncan, C. H., Wilson, G. A. and Young, F. E. 1977, Gene, 1:153-167). Alternatively, a method of making DNA-recipient cells into protoplasts or spheroplasts, which can easily take up recombinant DNA, followed by introducing the recombinant DNA into the cells, which is known to be applicable to Bacillus subtilis, actinomycetes and yeasts (Chang, S, and Choen, S. N., 1979, Mol. Gen. Genet, 168:111-115; Bibb, M. J. et al., 1978, Nature, 274:398-400; Hinnen, A., Hicks, J. B. and Fink, G. R. 1978, Proc. Natl. Sci., USA, 75:1929-1933) can also be employed. In addition, microorganisms can also be transformed by the electric pulse method (Japanese Patent Laid-open No. 2-207791).

The copy number of the target gene can also be increased by introducing multiple copies of the gene into the chromosomal DNA of the microorganism by homologous recombination (MillerI, J. H. Experiments in Molecular Genetics, 1972, Cold Spring Harbor Laboratory) using multiple copies of a sequence as targets in the chromosomal DNA. Sequences present in multiple copies on the chromosomal DNA include, but are not limited to, repetitive DNAs, and inverted repeats present at the end of a transposable element. Also, as disclosed in Japanese Patent Laid-open No. 2-109985, it is possible to incorporate the target gene into a transposon, and allow it to be transferred to introduce multiple copies of the gene into the chromosomal DNA. The target gene can also be introduced into the bacterial chromosome by Mu phage (Japanese Patent Laid-open No. 2-109985), or the like. Transfer of a target gene to a chromosome can be confirmed by Southern hybridization using a part of the gene as a probe.

When the copy number of a gene is increased, the copy number is not particularly limited so long as activity of the product of the target gene is enhanced. However, when the target gene is native to the chosen microorganism, the copy number is preferably 2 or more. When the target gene is not native to the chosen microorganism, the copy number of the gene may be 1, but it may also be 2 or more.

Expression of the target gene may also be increased by replacing an expression regulatory sequence of the target gene, such as promoter, on the chromosomal DNA or plasmid with a promoter which has an appropriate strength. For example, the thr promoter, lac promoter, trp promoter, trc promoter, pL promoter, tac promoter, etc., are known as promoters frequently used to increase expression of a target gene. Examples of strong promoters and methods for evaluating the strength of promoters are described in an article by Goldstein and Doi (Goldstein, M. A. and Doi R H., 1995, Biotechnol. Annu. Rev., 1:105-128), etc.

Moreover, it is also possible to substitute several nucleotides in the promoter region of a gene, so that the promoter has an appropriate strength, as disclosed in International Patent Publication WO00/18935. Substitution of the expression regulatory sequence can be performed, for example, in the same manner as in gene substitution using a temperature-sensitive plasmid. Examples of vectors having a temperature-sensitive replication origin which can be used for Escherichia coli or Pantoea ananatis include, for example, the temperature-sensitive plasmid pMAN997 described in International Publication WO99/03988, its derivatives, and so forth. Furthermore, substitution of an expression regulatory sequence can also be performed by methods which employ linear DNA, such as "Red-driven integration" using Red recombinase of λ phage (Datsenko, K. A. and Wanner, B. L., 2000, Proc. Natl. Acad. Sci. USA., 97:6640-6645), by combining the Red-driven integration method and the λ phage excision system (Cho, E. H., Gumport, R. I., Gardner, J. F. 2002, J. Bacteriol., 184:5200-5203) (WO2005/010175), and so forth. The modification of an expression regulatory sequence can be combined with increasing gene copy number described above.

Furthermore, it is known that substitution of several nucleotides in a spacer between the ribosome binding site (RBS) and the start codon, in particular, the sequences immediately upstream of the start codon, profoundly affects the mRNA translatability. Translation can be enhanced by modifying these sequences.

When pyruvate synthase consists of multiple subunits, the expression of the genes encoding the subunits may be individually enhanced, or may be simultaneously enhanced as a polycistron. Furthermore, when the genes are introduced into a microorganism by using a vector, the genes encoding the subunits may be carried on a single vector molecule, or may be separately carried on different vector molecules. Also when the genes encoding the subunits are inserted into the chromosome, the genes may be simultaneously inserted into the same site on the genome, or may be separately inserted at different sites.

Furthermore, pyruvate dehydrogenase activity may be reduced, in addition to enhancing pyruvate synthase activity or pyruvate:NADH$^+$ oxidoreductase activity.

Pyruvate dehydrogenase (henceforth also referred to as "PDH") activity means an activity for catalyzing the reaction of oxidatively decarboxylating pyruvic acid to produce acetyl-CoA. The aforementioned reaction is catalyzed by three kinds of enzymes, PDH (E1p, pyruvate dehydrogenase, EC:1.2.4.1, aceE gene, SEQ ID NO: 46), dihydrolipoyl transacetylase (E2p, EC:2.3.1.12, aceF gene, SEQ ID NO: 48), and dihydrolipoamide dehydrogenase (E3, EC:1.8.1.4, lpdA gene, SEQ ID NO: 50). That is, these three subunits catalyze the following reactions, respectively, and the activity for catalyzing the total reaction resulting from these three reactions is called PDH activity. PDH activity can be measured according to the method of Visser and Strating (Visser, J. and Strating, M., 1982, Methods Enzymol., 89:391-399).

E1p: Pyruvate+[dihydrolipoyllysine-residue succinyltransferase]lipoyllysine=[dihydrolipoyllysine-residue acetyltransferase]S-acetyldihydrolipoyllysine+$CO_2$ E2p: CoA+enzyme N6-(S-acetyldihydrolipoyl)lysine=acetyl-CoA+enzyme N6-(dihydrolipoyl)lysine E3: Protein N6-(dihydrolipoyl)lysine+$NAD^+$=protein N6-(lipoyl)lysine+$NADH+H^+$ To decrease or eliminate enzyme activity, for example, a part of or the entire coding region may be deleted from one or more of the aceE, aceF and lpdA genes, or an expression control sequence such as a promoter or Shine Dargarno (SD) sequence can be modified, or the like. The expression can also be reduced by modifying a non-translation region other than expression control regions. Furthermore, the entire gene, including the upstream and downstream regions of the genes on the chromosome, may be deleted. In addition, an amino acid substitution (missense mutation), a stop codon (nonsense mutation), or a frame shift mutation which adds or deletes one or two nucleotides may be introduced into the enzyme coding region on the chromosome by genetic recombination (Journal of Biological Chemistry, 272:8611-8617 (1997), Proceedings of the National Academy of Sciences, USA, 95 5511-5515 (1998), Journal of Biological Chemistry, 266, 20833-20839 (1991)).

To reduce the intracellular enzymatic activity, a part or all of an expression control sequence such as promoter region, a coding region or a non-coding region of the gene on the chromosome may be deleted, or another sequence may be inserted into these regions by homologous recombination. However, these modifications may be accomplished by known mutatagenesis techniques, such as exposure to X-rays or UV irradiation, or treatment with a mutagen such as N-methyl-N'-nitro-N-nitrosoguanidine, etc., so long as the PDH activity is reduced by the modification.

The expression control sequence is preferably modified by one or more nucleotides, more preferably two or more nucleotides, particularly preferably three or more nucleotides. When a coding region is deleted, it may be in the N-terminus region, an internal region, or the C-terminus region, or even the entire coding region, so long as the function of the enzyme protein is reduced. Deletion of a longer region will usually ensure inactivation of the gene. Furthermore, the reading frames upstream and downstream of the deleted region are not preferably the same.

Also, when another sequence is inserted into the coding region, the sequence may be inserted anywhere, and inserting a longer region will usually ensure inactivation of the gene. The reading frames upstream and downstream of the insertion site are not preferably the same. The other sequence is not particularly limited so long as the sequence reduces or deletes the function of the enzyme protein, and examples include a transposon carrying an antibiotic resistance gene or a gene useful for L-amino acid production.

A gene on the chromosome can be modified as described above by, for example, preparing a deletion-type version of the gene in which a partial sequence of the gene is deleted, and transforming a bacterium with a DNA containing the deletion-type gene to cause homologous recombination between the deletion-type gene and the native gene on the chromosome, and thereby substitute the deletion-type gene for the gene on the genome. The enzyme protein encoded by the deletion-type gene has a conformation different from that of the wild-type enzyme protein, if it is even produced, and thus the function is reduced or deleted. These types of gene disruption can be performed by methods using a linear DNA such as Red-driven integration, and Red-driven integration in combination with an excision system derived from λ phage, or by using a plasmid containing a temperature-sensitive replication origin, or a plasmid capable of conjugative transfer, utilizing a suicide vector which does not have a replication origin usable in the chosen host (U.S. Pat. No. 6,303,383, JP 05-007491 A) etc.

The aforementioned description concerning reduction of the PDH activity is also applied to "reduction of activity" of the other enzymes described above, or "destruction" of the other genes described above.

When the microorganism is cultured under anaerobic or microaerobic conditions, it may be already have been modified so that it does not produce any organic acid or ethanol under the anaerobic or microaerobic conditions, in addition to enhancing the pyruvate synthase activity or pyruvate:NADH$^+$ oxidoreductase activity. Examples of the organic acids include lactic acid, formic acid, and acetic acid. The method for modifying a microorganism so that organic acid or ethanol is not produced include by disrupting the gene encoding lactate dehydrogenase (Verumi, G. N. et al., 2002, J. Industrial Microbiol. Biotechnol., 28:325-332; Japanese Patent Laid-open No. 2005-95169).

<2> Method for Producing an L-Amino Acid

The microorganism is cultured in a medium to produce and cause accumulation of an L-amino acid in the medium or cells, and collecting the L-amino acid from the medium or cells.

A batch culture, fed-batch culture, and/or continuous culture may be used. Ethanol or an aliphatic acid may be added to the starting medium or feed medium, or both.

A fed-batch culture refers to a culture method in which the medium is continuously or intermittently fed into the culture vessel, and the medium is not extracted until the end of the culture. A continuous culture means a method in which the medium is continuously or intermittently fed into the culture vessel, and the medium is extracted from the vessel (usually in a volume equivalent to the volume of the fed medium) at the same time. A starting medium indicates the medium used in the batch culture, the fed-batch culture, or continuous culture before feeding the feed medium, that is, the medium used at the start of the culture. A feed medium indicates the medium which is supplied to the fermentation tank in the fed-batch culture or continuous culture. A batch culture means a method in which fresh medium is prepared for every culture, and the strain is inoculated into the medium, and the medium is not added until harvest.

A substance from which acetyl-CoA can be produced without a decarboxylation reaction is preferred as the carbon source, and specific examples include ethanol, aliphatic acids, aliphatic acid esters including fats and oils which generate an aliphatic acid upon decomposition, and so forth. Examples of using ethanol or an aliphatic acid as the carbon source will be described below.

Ethanol is a monohydric alcohol represented by the molecular formula $C_2H_5OH$, and may be used alone, or may be present as a mixture in the medium, such as the ethanol which is produced in ethanol fermentation in the medium etc.

Aliphatic acids are monovalent carboxylic acids represented by the general formula $C_mH_nCOOH$. So long as it is able to be assimilated by the bacteria having L-amino acid-producing ability, it may be of any length, and may contain aliphatic acids of any length at any ratio. Preferred aliphatic acids are oleic acid ($C_{17}H_{33}COOH$) and palmitic acid ($C_{15}H_{31}COOH$), and oleic acid is particularly preferred. A mixture of long chain aliphatic acids containing oleic acid can be obtained by hydrolysis of fats and oils. Oleic acid can be obtained as a hydrolysate of fats and oils such as palm oil, and oleic acid extracted from animal oils, vegetable oils, waste cooking oils, other blended fats and oils, or foodstuffs containing fats such as chocolate may be used. The aliphatic acid may be a free acid, or an alkali metal salt, such as sodium salts and potassium salts, or an ammonium salt.

Ethanol or aliphatic acids may be present in the medium at any concentration so long as the chosen bacterium can assimilate it as the carbon source. When it is used as the sole carbon source in the medium, it is present in an amount of 20% w/v or less, more preferably 10% w/v or less, still more preferably 2% w/v or less. Furthermore, ethanol or aliphatic acids may be present in the medium at any concentration so long as it can be assimilated as the carbon source by the chosen bacterium. When it is used as the sole carbon source in the medium, it is desirably present in the medium in an amount of 0.001% w/v or more, preferably 0.05% w/v or more, more preferably 0.1% w/v or more.

As for the feed medium, when ethanol or aliphatic acid is used as the sole carbon source, it is preferably present in the medium in an amount of 10% w/v or less, more preferably 5% w/v or less, still more preferably 1% w/v or less, and it is preferably present in the medium in an amount of 0.001% w/v or more, more preferably 0.05% w/v or more, still more preferably 0.1% w/v or more.

Although the concentration of ethanol can be measured by various methods, the enzymatic method is convenient and common (Swift R., 2003, Addiction, 98:73-80). The concentration of aliphatic acid can be measured by known methods such as gas chromatography and HPLC (TrAC Trends Anal. Chem., 2002, 21:686-697; Lin J. T., Snyder L. R., and McKeon, T. A., 1998, J. Chromatogr. A., 808:4349).

Furthermore, the medium may contain a mixture of ethanol and an aliphatic acid. The concentrations of ethanol and aliphatic acid which are added may be any concentration so long as the chosen bacterium can assimilate them as the carbon source. However, when a mixture of ethanol and an aliphatic acid is used as the sole carbon source in the medium, it is preferably present in an amount of 20% w/v or less, more preferably 10% w/v or less, still more preferably 2% w/v or less, in terms of the total concentration. Furthermore, a mixture of ethanol and an aliphatic acid may be present in the medium at any concentration so long as it can be assimilated as the carbon source by the bacterium. However, when a mixture of ethanol and an aliphatic acid is used as the sole carbon source in the medium, it is desirably contained in the medium in an amount of 0.001% w/v or more, preferably 0.05% w/v or more, more preferably 0.1% w/v or more, in terms of the total concentration of ethanol and oleic acid.

Any ratio of ethanol and aliphatic acid may be present so long as they are at such concentrations that the chosen bacteria can assimilate them as the carbon source. However, the aliphatic acid is generally mixed at a ratio of about 2 or less, preferably about 1.5 or less, preferably about 1 or less, based on ethanol, which is taken as 1. Although the lower limit of the mixing ratio of the aliphatic acid is not particularly limited in the case of mixing the aliphatic acid, the aliphatic acid is preferably mixed at a ratio of 0.05 or more, desirably 0.1 or more, based on ethanol, which is taken as 1.

In addition to ethanol or aliphatic acid, or both, other carbon sources may also be added to the medium, for example, such as saccharides such as glucose, fructose, sucrose, lactose, galactose, blackstrap molasses, and starch hydrolysate, polyhydric alcohols such as glycerol and organic acids such as fumaric acid, citric acid, and succinic acid. Glucose, sucrose, fructose, and glycerol are especially preferred. As glycerol, crude glycerol produced in biodiesel fuel production can also be used. The carbon source may be one kind of substance or a mixture of two or more kinds of substances. When other carbon sources are used, the ratio of ethanol, aliphatic acid, or a mixture of ethanol and aliphatic acid in the carbon source is preferably 10% by weight or more, more preferably 30% by weight or more, still more preferably 50% by weight or more.

Ethanol or aliphatic acid may be present at a certain constant concentration throughout the culture process, or it may be added only to the starting medium or the feed medium. If other carbon sources are sufficient, there may be a period where ethanol or aliphatic acid temporarily runs short. The term "temporarily" means that, for example, the aliphatic acid may run short for a period corresponding to 10%, 20%, or 30% at most, of the entire fermentation period.

As for the other components to be added to the medium, typical media ingredients such as a nitrogen source, inorganic ions, and if needed, other organic components in addition to the carbon source can be used. Examples of the nitrogen source present in the medium include ammonia, ammonium salts such as ammonium sulfate, ammonium carbonate, ammonium chloride, ammonium phosphate, ammonium acetate and urea, nitrates, and so forth Ammonia gas and aqueous ammonia used to adjust the pH can also be utilized as the nitrogen source. Furthermore, peptone, yeast extract, meat extract, malt extract, corn steep liquor, soybean hydrolysate, and so forth can also be utilized. The medium may contain one or more of these nitrogen sources. These nitrogen sources can also be used for both the starting medium and the feed medium. Furthermore, the same nitrogen source can be used for both the starting medium and the feed medium, or the nitrogen source of the feed medium may be different from that of the starting medium.

The medium preferably contains a phosphoric acid source and a sulfur source in addition to the carbon source, the nitrogen source, and sulfur. As the phosphoric acid source, potassium dihydrogenphosphate, dipotassium hydrogenphosphate, phosphate polymers such as pyrophosphoric acid and so forth can be utilized. Although the sulfur source may be any substance containing sulfur atoms, sulfuric acid salts such as sulfates, thiosulfates and sulfites, and sulfur-containing amino acids such as cysteine, cystine and glutathione are desirable, and ammonium sulfate is especially desirable.

Furthermore, the medium may contain a growth promoting factor, such as a nutrient with a growth promoting effect, in addition to the carbon source, nitrogen source and sulfur. As the growth promoting factor, trace metals, amino acids, vitamins, nucleic acids as well as peptone, casamino acid, yeast extract, soybean protein degradation product and so forth containing the foregoing substances can be used. Examples of the trace metals include iron, manganese, magnesium, calcium, and so forth Examples of the vitamins include vitamin $B_1$, vitamin $B_2$, vitamin $B_6$, nicotinic acid, nicotinamide, vitamin $B_{12}$ and so forth. These growth promoting factors may be present in the starting medium or the feed medium.

Furthermore, when an auxotrophic mutant that requires an amino acid or the like for growth thereof is used, it is preferable to supplement the required nutrient to the medium. In particular, since the L-lysine biosynthetic pathway is enhanced and L-lysine degrading ability is often attenuated in L-lysine-producing bacteria, one or more of L-threonine, L-homoserine, L-isoleucine, and L-methionine are preferably added. The starting medium and the feed medium may have the same or different medium composition. Furthermore, when the feed medium is fed at multiple stages, the compositions of the feed medium fed at the various stages may be the same or different.

The culture is preferably performed as an aeration culture at a fermentation temperature of 20 to 45° C., particularly preferably at 33 to 42° C. The oxygen concentration is adjusted to 5 to 50%, desirably about 10%. Furthermore, the aeration culture is preferably performed with the pH adjusted to 5 to 9. If pH is lowered during the culture, for example, calcium carbonate or an alkali such as ammonia gas and aqueous ammonia is added to neutralize the culture. When culture is performed under such conditions preferably for about 10 to 120 hours, a marked amount of L-amino acid accumulates in the culture medium. Although the concentration of L-amino acid which accumulates is not limited so long as it is higher than that observed with wild-type strains and the L-amino acid can be isolated and collected from the medium, it may be 50 g/L or higher, desirably 75 g/L or higher, more desirably 100 g/L or higher.

When the target amino acid is a basic amino acid, the fermentation is performed with the pH of the medium controlled to be 6.5 to 9.0 during the culture and to be 7.2 to 9.0 at the end of the culture. Furthermore, the internal pressure in the fermentation tank is controlled to be positive during the fermentation, or carbon dioxide or a mixed gas containing carbon dioxide is supplied to the medium so that there is a culture period that bicarbonate ions and/or carbonate ions are present in an amount of 2 g/L or larger in the medium, and thereby the bicarbonate ions and/or carbonate ions can be used as counter ions of cations mainly consisting of the basic amino acid (refer to JP 2002-065287 A).

The L-amino acid can be collected by a known collection method from the culture medium after the culture. For example, the L-amino acid can be collected by an ion exchange resin method or precipitation method, or after the bacterial cells are removed from the culture medium by centrifugation or the like, the L-amino acid is collected by concentration for crystallization.

The culture of the microorganism may be performed as a seed culture and a main culture in order to ensure accumulation of the L-amino acid higher than a certain level. The seed culture may be performed as a shaking culture using a flask or the like, or batch culture, and the main culture may be performed as fed-batch culture or continuous culture. Alternatively, both the seed culture and the main culture may be performed as batch culture.

When a fed-batch culture or continuous culture is performed, the feed medium may be intermittently fed so that the supply of ethanol, aliphatic acid or other carbon sources is temporarily stopped. The supply of the feed medium is preferably stopped for, at maximum, 30% or less, desirably 20% or less, particularly desirably 10% or less, of the feeding time. When the feed medium is intermittently fed, the feed medium may be initially added over a predetermined time, and the second and following additions may be controlled so that it is started when pH increases or the dissolved oxygen concentration is detected by a computer upon depletion of the carbon source in the fermentation medium during an addition-stopped period prior to a certain medium-addition period, and thus the substrate concentration in the culture tank is always automatically maintained at a low level (U.S. Pat. No. 5,912, 113).

The feed medium used for the fed-batch culture preferably contains ethanol or an aliphatic acid, another carbon source, and a nutrient having a growth promoting effect (growth promoting factor), and may be controlled so that the concentration of the aliphatic acid in the fermentation medium is at a predetermined concentration or lower. The expression "predetermined concentration or lower" means that the medium is prepared so that the aliphatic acid concentration in the medium becomes 10% w/v or lower, preferably 5% w/v or lower, more preferably 1% w/v or lower.

As the other carbon source, glucose, sucrose, fructose and glycerol are preferred. As the growth promoting factor, nitrogen sources, phosphoric acid, amino acids and so forth are preferred. As the nitrogen source, ammonia, ammonium salts such as ammonium sulfate, ammonium carbonate, ammonium chloride, ammonium phosphate, ammonium acetate and urea, nitrates and so forth can be used. Furthermore, as the phosphoric acid source, potassium dihydrogenphosphate and dipotassium hydrogenphosphate can be used. As for the amino acids, when an auxotrophic mutant strain is used, it is preferable to supplement the required nutrient. Furthermore, the feed medium may consist of one type of medium, or a mixture of two or more types of media. When two or more types of feed media are used, the media may be mixed and fed by using one feed can, or the media may be separately fed by using two or more feed cans.

When the continuous culture method is used for the present invention, the medium may be extracted and fed simultaneously, or a part of the medium may be extracted, and then the medium may be fed. Furthermore, the method may also be a continuous culture method in which the culture medium containing L-amino acids and bacterial cells is extracted, and only the cells are returned to the fermenter for reuse (French Patent No. 2669935). As the method for continuously or intermittently feeding a nutrient source, the same method as used in the fed-batch culture is used.

The continuous culture method reusing bacterial cells intermittently or continuously extracts the fermentation medium when the amino acid concentration reaches a predetermined level, extracting only L-amino acid and re-circulating filtration residues containing bacterial cells into the fermenter, and it can be performed by referring to, for example, French Patent No. 2669935.

When the culture medium is intermittently extracted, it is preferred that some of the L-amino acid is extracted when the L-amino acid concentration reaches a predetermined level, and a fresh medium is fed to continue the culture. Furthermore, as for the volume of the medium to be added, the culture is preferably performed so that the final volume of the medium after the addition of the medium is equal to the volume of the culture medium before the extraction. The term "equal" used herein means that the volume after the addition of the medium corresponds to about 93 to 107% of the volume of the medium before the extraction.

When the culture medium is continuously extracted, the extraction is preferably stared at the same time as, or after the feeding of, the nutrient medium. For example, within 5 hours, desirably 3 hours, more desirably 1 hour, after the start of the feeding, the extraction is started. Furthermore, the extraction volume of the culture medium is preferably equal to the volume of the fed medium.

EXAMPLES

Hereinafter, the present invention will be more specifically explained with reference to the following non-limiting examples.

Example 1

Construction of Alcohol Dehydrogenase (AdhE) Mutated Strain Derived from *Escherichia coli*

An *Escherichia coli* strain having mutant alcohol dehydrogenase AdhE was constructed so as to obtain an aerobically ethanol assimilable *Escherichia coli* strain. The nucleotide sequence of the wild-type AdhE gene (adhE) derived from *Escherichia coli* and the encoded amino acid sequence are shown in SEQ ID NOS: 21 and 22, respectively.

<1-1> Construction of *Escherichia coli* MG1655::$P_{L\text{-}tac}$-adhE Strain

Substitution of the $P_{L\text{-}tac}$ promoter for the promoter region of the *Escherichia coli* adhE gene was performed by "Red-driven integration", which was developed by Datsenko and Wanner (Datsenko, K. A. and Wanner, B. L., 2000, Proc. Natl. Acad. Sci. USA., 97:6640-6645) using the excision system derived from λ phage (Cho, E. H., Gumport, R. I., and Gardner, J. F., 2002, J. Bacteriol., 184:5200-5203).

By this technique, a genetic recombinant strain can be constructed in one step using a PCR product obtained by using primers designed so as to contain a part of a target gene at the 5' end and a part of antibiotic resistance gene at the 3' end. By further using the excision system derived from λ phage in combination, it is possible to eliminate the antibiotic resistance gene which had been integrated into the genetic recombinant strata A fragment containing the $P_{L-tac}$ promoter and the cat gene encoding the chloramphenicol resistance ($Cm^R$) gene was amplified by PCR using the genome of the *Escherichia coli* MG1655 $P_{L-tac}$xylE strain described in WO2006/043730 as the template and the primers shown in SEQ ID NOS: 23 and 24. The primer of SEQ ID NO: 23 has a sequence complementary to the upstream region of the adhE gene, and the primer of SEQ ID NO: 23 has a sequence complementary to a 5' region of the adhE gene.

The sequence of the $P_{L-tac}$ promoter is shown in SEQ ID NO: 25. For PCR, Gene Amp PCR System 2700 Amplificatory (Applied Biosystems) and Taq DNA polymerase (Fermentas) were used. The amplified fragment was purified and collected by agarose gel electrophoresis. This fragment was introduced into the *Escherichia coli* MG1655/pKD46 strain harboring the plasmid pKD46 having a temperature-sensitive replication ability by electroporation.

The strain was grown on M9 medium plates (Sambrook J., Fritsch, E. F., and Maniatis, T, 1989, Molecular Cloning A Laboratory Manual/Second Edition, Cold Spring Harbor Laboratory Press, New York) containing 2% ethanol for 36 hours, and about 100 clones appeared. PCR amplification was performed using the primers shown in SEQ ID NOS: 26 and 27, and then the nucleotide sequence of the amplified product was determined. It was confirmed that one of the clones contained the $Cm^R$ gene in the promoter region of the adhE gene, and this clone was cultured at 37° C. to eliminate the temperature-sensitive plasmid pKD46 and thereby obtain an MG1655::$P_{L-tac}$adhE strain.

<1-2> Construction of *Escherichia coli* MG1655ΔadhE Strain

The adhE gene of wild-type *Escherichia coli* MG1655 (ATCC 700926) was replaced with an inactivated adhE gene by the method developed by Datsenko and Wanner. A fragment containing the kan gene encoding the kanamycin resistance ($Kan^R$) marker was amplified by PCR using the plasmid pACYC177 (GenBank/EMBL accession number X06402, Fermentas) as the template and the primers shown in SEQ ID NOS: 28 and 29. The primer of SEQ ID NO: 28 has a sequence of 40 bases complementary to the region 318 bp upstream of the adhE gene, and the primer of SEQ ID NO: 29 has the sequence of 41 bases complementary to the region on the 3' side of the adhE gene. For PCR, Gene Amp PCR System 2700 Amplificatory (Applied Biosystems) and Taq DNA Polymerase (Fermentas) were used. The amplified fragment was purified and collected by agarose gel electrophoresis. This fragment was introduced into the *Escherichia coli* MG1655/pKD46 strain harboring the plasmid pKD46 by electroporation.

PCR amplification was performed by using the primers shown in SEQ ID NOS: 30 and 31 to confirm the presence of the $Km^R$ gene in clones grown on the LB plate medium (Sambrook, J., Fritsch, E. F., and Maniatis, T., 1989, Molecular Cloning A Laboratory Manual/Second Edition, Cold Spring Harbor Laboratory Press, New York) containing 20 µg/ml of kanamycin. One of clones confirmed to contain the $Km^R$ gene in the adhE gene region was cultured at 37° C. to remove the temperature-sensitive plasmid pKD46 and thereby obtain an MG1655ΔadhE strain.

<1-3> Construction of Mutant Alcohol Dehydrogenase (AdhE*)

In order to introduce the Glu568Lys (E568K) mutation into AdhE, PCR was performed using the primer of SEQ ID NO: 32 which is complementary to nucleotide sequences of 1662 to 1701 and 1703 to 1730 of the adhE gene and containing a g->a mutation at the nucleotide of position 1702, the primer of SEQ ID NO: 33 which is homologous to the 3' end region of the adhE gene, and the genome of the *Escherichia coli* MG1655 strain as the template. For PCR, Gene Amp PCR System 2700 Amplificatory (Applied Biosystems) and Pyrobest DNA Polymerase (Takara Shuzo) were used. The amplification fragment of 1.05 kbp was purified and collected by agarose gel electrophoresis.

PCR was performed using the genome of the *Escherichia coli* MG1655::$P_{L-tac}$adhE strain as the template, the primer shown in SEQ ID NO: 34 and the 1.05 kbp fragment having the mutation as another primer. The primer of SEQ ID NO: 34 corresponds to the sequence from 402 to 425 bp upstream from the start codon of the adhE gene. For PCR, Gene Amp PCR System 2700 Amplificatory (Applied Biosystems) and TaKaRa LA DNA Polymerase (Takara Shuzo) were used. The amplification fragment of 4.7 kbp was purified and collected by agarose gel electrophoresis.

In order to replace the wild-type adhE gene with the mutant adhE gene, the 4.7 kbp fragment containing the $Cm^R$ gene and the mutant adhE gene downstream of the $P_{L-tac}$ promoter (cat-$P_{L-tac}$adhE*) was introduced into the MG 655ΔadhE/pKD46 strain by electroporation according to the method of Datsenko and Wanner. The clones were selected on the M9 plate medium containing 2% ethanol as the sole carbon source. By sequencing the adhE gene of the grown clone, Glu568Lys (gag-aag), Ile554Ser (atc-agc), Glu22Gly (gaa-gga), Met236Val (atg-gtg), Tyr461Cys (tac-tgc) and Ala786Val (gca-gta) were identified, and this clone was designated MG1655::$P_{L-tac}$adhE*.

The MG1655Δtdh rhtA* strain was transformed via P transduction with $P1_{vir}$ phage (Miller, J. H., 1972, Experiments in Molecular Genetics, Cold Spring Harbor Lab. Press, Plainview, N.Y.) using the *Escherichia coli* MG655::$P_{L-tac}$adhE* strain as a donor, and MG1655Δtdh rhtA* $P_{L-tac}$adhE* was obtained. The MG1655Δtdh, rhtA* strain corresponds to the MG1655 strain, but the tdh gene encoding threonine dehydrogenase is disrupted by the method of Datsenko and Wanner and a rhtA23 mutation is introduced therein, which imparts resistance to high concentrations of threonine in a minimal medium to the rhtA gene (Livshits, V. A., Zakataeva, N. P., Aleshin, V. V., Vitushkina, M. V., 2003, Res. Microbiol., 154:123-135).

<1-4> Construction of Alcohol Dehydrogenase (AdhE) Mutated Strain Derived from *Escherichia coli* WC196Δmez Strain In order to impart ethanol assimilability to an L-lysine-producing bacterium, the L-lysine-producing bacterium WC196Δmez/pCABD2 strain described in International Patent Publication WO2005/010175 was subjected to P1 transduction using MG1655Δtdh rhtA adhE* as a donor to obtain a WC196Δmez adhE*/pCABD2 strain. pCABD2 is the plasmid described in U.S. Pat. No. 6,040,160, and has the dapA* gene which imparts resistance to feedback inhibition by L-lysine, the lysC* gene which imparts resistance to feedback inhibition by L-lysine, the dapB gene, and ddh gene.

Example 2

Construction of a Plasmid to Express the Pyruvate Synthase Gene of *Chlorobium tepidum* and Measurement of the Activity <2-1> Construction of a Plasmid to Express the Pyruvate Synthase Gene of *Chlorobium tepidum*

*Chlorobium tepidum* is a meso- to thermophilic autotrophic bacterium, and its optimum growth temperature is 48° C. The genome sequence of the *Chlorobium tepidum* TLS strain has been elucidated by Eisen et al. (Eisen, J. A. et al, 2002, Proc. Natl. Acad. Sci. USA, 99:9509-9514). The pyruvate synthase gene was isolated from this strain, and a plasmid expressing it was constructed.

<2-2> Measurement of Pyruvate Synthase Activity in a Strain Expressing the Pyruvate Synthase Gene of *Chlorobium tepidum*

PCR was performed using the chromosomal DNA of the *Chlorobium tepidum* TLS strain (ATCC 49652) as the template and the oligonucleotides shown in SEQ ID NOS: 35 and 36 to amplify a pyruvate synthase gene fragment. The gene fragment was digested with SacI, and inserted into the SacI site of pSTV28 (Takara Bio) to construct a plasmid, which was designated pSTV-PS. After it was confirmed that the pyruvate synthase gene contained no PCR error over the full length by using BigDye Terminators v1. Cycle Sequencing Kit, the pyruvate synthase gene was excised from pSTV-PS with SacI, and inserted into the SacI site of pMW-Pthr to construct plasmid pMW-Pthr-PS. pMW-Pthr corresponds to the vector pMW219 (Nippon Gene) having the promoter region (Pthr) of the threonine operon (thrABC) of the *Escherichia coli* K-12 strain between the HindIII site and the XbaI site and which is capable of expressing the gene cloned downstream of the promoter. The promoter sequence of the chosen threonine operon is shown in SEQ ID NO: 37.

pMW-Pthr-PS and the control vector pMW-Pthr were introduced into the WC196ΔcadAΔldc/pCABD2 strain by electroporation, respectively, and transformants were obtained on the basis of the kanamycin resistance, and the presence of the plasmids was confirmed. The strain expressing the pyruvate synthase gene of *Chlorobium tepidum* was designated WC196ΔcadAΔldc/pCABD2/pMW-Pthr-PS, and the control strain was designated WC196ΔcadAΔldc/pCABD2/pMW-Pthr.

The aforementioned strains were each inoculated into LB medium containing 20 mg/l of streptomycin and 40 mg/l of kanamycin, and cultured overnight at 37° C. with shaking. The cells were collected by centrifugation and suspended in a 50 mM HEPES buffer (pH 8.0). The cells in the suspension were disrupted by using an ultrasonicator, the suspension was centrifuged at 15000 rpm for 15 minutes, and the supernatant was used as a crude enzyme solution.

Protein concentration in the crude enzyme solution was measured by using Protein Assay CBB Solution (Nakalai Tesque), and the crude enzyme solution containing 250 μg of the total protein was used to measure the activity.

The activity was measured as follows. 2 ml of the following reaction solution was added to the crude enzyme solution. The reaction solution containing all the ingredients except for pyruvic acid was first added to a cell for spectrometry, and the cell was sealed with a rubber stopper and an aluminum cap. The oxygen concentration was reduced in the cell by injecting argon gas into the cell for 5 minutes using a syringe, and then the cell was set on a spectrophotometer (U-3210 Spectrophotometer, Hitachi). A pyruvic acid solution was added by using a syringe to start the reaction. The reaction continued at 37° C. for 30 minutes, and absorbance was periodically measured at 578 nm to examine the change in the reduced methylviologen amount. The results are shown in Table 1. In the table, the unit of the specific activity is U/mg protein. One unit is defined as activity for reducing 1 nmol of methylviologen per 1 minute.

| Reaction mixture: | |
| --- | --- |
| $MgCl_2$ | 1 mM |
| Dithiothreitol | 1 mM |
| Methylviologen | 5 mM |
| CoA | 0.25 mM |
| Pyruvic acid (added immediately before start of measurement) | 10 mM |
| HEPES (pH 8.0) | 50 mM |

TABLE 1

| Plasmid | Specific activity |
| --- | --- |
| pMW-Pthr | 0.0 |
| pMW-Pthr-PS | 1.2 |

Example 3

Construction of a Plasmid to Express the Pyruvate Synthase Gene of *Chlorobium tepidum*, Flavodoxin $NADP^+$ Reductase Gene of *Escherichia coli*, and Ferredoxin Gene of *Escherichia coli*

By using the flavodoxin $NADP^+$ reductase gene of *Escherichia coli* (fr) and the ferredoxin gene of *Escherichia coli* (fdx) as coenzyme regenerating systems, a plasmid simultaneously expressing all three genes, including the pyruvate synthase gene, was constructed.

<3-1> Construction of a Vector to Amplify the Flavodoxin $NADP^+$ Reductase Gene of *E. coli*

PCR was performed using the chromosomal DNA of the *E. coli* MG1655 strain as the template and the oligonucleotides shown in SEQ ID NOS: 42 and 43. The gene fragment was digested with SmaI and inserted into the SmaI site of pMW-Pthr to construct a plasmid for amplifying the flavodoxin $NADP^+$ reductase gene, which was designated pMW-Pthr-fpr.

<3-3> Construction of a Plasmid to Amplify the Ferredoxin (fdx) gene of *E. coli*

PCR was performed using the chromosomal DNA of the *E. coli* MG1655 strain as the template and the oligonucleotides shown in SEQ ID NOS: 44 and 45. The gene fragment was digested with EcoRI, and inserted into the EcoRI site of pMW-Pthr to construct a plasmid to amplify the ferredoxin (fdx) gene, pMW-Pthr-fdx.

<3-4> Construction of a Plasmid to Amplify the Pyruvate Synthase Gene of *C. tepidum*, the Flavodoxin $NADP^+$ Reductase Gene, and the Ferredoxin (fx) Gene of *E. coli* pMW-Pthr-fpr was digested with SmaI, and their gene fragment was ligated with pMW-Pthr-fdx which had been treated with SmaI to obtain pMW-Pthr-fpr-fdx. Then, pMW-Pthr-PS was digested with SacI and the PS gene fragment was ligated with pMW-Pthr-fpr-fdx which had been treated with SacI to construct a plasmid to express the pyruvate synthase gene of *C. tepidum* and enhance expression of the flavodoxin NADP+ reductase and the ferredoxin (fdx) genes of *E. coli*, and was named pMW-Pthr-fpr-PS-fdx.

In the aforementioned plasmids, the pyruvate synthase gene of *C. tepidum* is transcribed from Pthr, and the other genes are also transcribed by read through from Pthr.

Example 4

Effect on the L-Lysine-Producing Ability of a Strain with Enhanced Expression of the Pyruvate Synthase Gene of *Chlorobium tepidum*, Flavodoxin NADP+ Reductase Gene of *Escherichia coli*, and Ferredoxin Gene of *Escherichia coli*, Using Oleic Acid as the Carbon Source <4-1> Introduction of the Plasmid to Amplify The Pyruvate Synthase Gene of *Chlorobium tepidum*, Flavodoxin NADP+ Reductase Gene of *Escherichia coli*, and Ferredoxin Gene of *Escherichia coli* into the WC196Δmez Strain pMW-Pthr-fpr-PS-fdx and the control vector pMW-Pthr were introduced into WC196Δmez/pCABD2 by electroporation, respectively, and transformants were obtained on the basis of the kanamycin resistance, and introduction of the plasmids were confirmed. The strain expressing the pyruvate synthase gene of *Chlorobium tepidum*, the flavodoxin NADP+ reductase gene of *Escherichia coli* and the ferredoxin gene of *Escherichia coli* was designated WC196Δmez/pCABD2/pMW-Pthr-fpr-PS-fdx, and the control strain was designated WC196Δmez/pCABD2/pMW-Pthr.

<4-2> Effect on L-Lysine-Producing Ability of the Strain with Enhanced Expression of the Pyruvate Synthase Gene of *Chlorobium tepidum*, Flavodoxin NADP+ Reductase Gene of *Escherichia coli*, and Ferredoxin Gene of *Escherichia coli* Using Oleic Acid as the Carbon Source Both WC196Δmez/pCABD2/pMW-Pthr and WC196Δmez/pCABD2/pMW-Pthr-fpr-PS-fdx were inoculated onto the LB plate medium, respectively, and precultured overnight at 37° C. The cells corresponding to ⅛ of the plate were inoculated into 20 ml of the oleic acid medium having the following composition in a 500 ml-volume Sakaguchi flask, and aerobically cultured at a stirring rate of 120 rpm at 37° C. for 72 hours. The L-lysine that accumulated in the medium was measured by using Biosensor BF-5 (Oji Scientific Instruments). The live cell count in the medium was also measured. Averages of the values obtained in the culture performed in duplicate are shown in Table 2. Improvement in L-lysine accumulation was observed for the strain in which expression of pyruvate synthase gene of *Chlorobium tepidum*, flavodoxin NADP+ reductase gene of *Escherichia coli* and ferredoxin gene of *Escherichia coli* were enhanced, compared with the control.

| Composition of oleic acid medium: | |
| --- | --- |
| Sodium oleate | 20 g/L |
| MgSO$_4$·7H$_2$O | 1.0 g/L |
| (NH$_4$)$_2$SO$_4$ | 12 g/L |
| KH$_2$PO$_4$ | 0.5 g/L |
| Yeast extract | 1.0 g/L |
| FeSO$_4$·7H$_2$O | 0.01 g/L |
| MnSO$_4$·5H$_2$O | 0.01 g/L |
| Kanamycin | 40 mg/L |
| Streptomycin | 20 mg/L |
| Calcium carbonate | 30 g/L | pH 7.0 (adjusted with KOH)
Sterilization conditions: 115° C., 10 minutes

TABLE 2

| Strain | L-lysine (g/l) | Live cell count ($10^8$/ml) |
| --- | --- | --- |
| WC196Δmez/pCABD2/pMW-Pthr | 1.77 | 22.3 |
| WC196Δmez/pCABD2/pMW-Pthr-fpr-PS-fdx | 2.35 | 13.6 |

Example 5

Construction of a Plasmid to Express the Pyruvate Synthase Gene of *Escherichia coli* and Measurement of Activity An expression plasmid for the ydbK gene, which is homologous to the pyruvate synthase gene found in the genome of *Escherichia coli* MG1655 strain, was constructed, and the activity was measured.

<5-1> Construction of a Plasmid to Express the Pyruvate Synthase Gene of *Escherichia coli*

PCR was performed using the chromosomal DNA of the *Escherichia coli* MG1655 strain as the template and the oligonucleotides shown in SEQ ID NOS: 38 and 39. The gene fragment was digested with KpnI and the digested fragment was inserted into the KpnI site of pSTV28 (Takara Bio) to construct a plasmid, which was designated pSTV-ydbK After it was confirmed that the pyruvate synthase gene contained no PCR error over the full length by using BigDye Terminators v1.1 Cycle Sequencing Kit, the pyruvate synthase gene was excised from pSTV-ydbK with KpnI, and inserted into the KpnI site of pMW-Pthr to construct the plasmid pMW-Pthr-ydbK <5-2> Measurement of Pyruvate Synthase Activity in a Strain Expressing the Pyruvate Synthase Gene of *Escherichia coli* pMW-Pthr-ydbK and the control vector pMW-Pthr were introduced into the WC196ΔcadAΔldc/pCABD2 strain by electroporation, respectively, and transformants were obtained on the basis of the kanamycin resistance, and introduction of the plasmids was confirmed. The strain expressing the pyruvate synthase gene of *Escherichia coli* was designated WC196ΔcadAΔldc/pCABD2/pMW-Pthr-ydbK, and the control strain was designated WC196ΔcadAΔldc/pCABD2/pMW-Pthr.

The aforementioned strains were each inoculated into LB medium containing 20 mg/l of streptomycin and 40 mg/l of kanamycin, and cultured overnight at 37° C. with shaking. The cells were collected by centrifugation, and the activity was measured in the same manner as that for the strain expressing the pyruvate synthase gene of *Chlorobium tepidum* described in Example 2. The results are shown in Table 3. Whereas the activity of pyruvate synthase was not confirmed for the control strain WC196ΔcadAΔldc/pCABD2/pMW-Pthr, 8.0 U/mg was confirmed for the strain expressing the pyruvate synthase gene of *Escherichia coli*, WC196ΔcadAΔldc/pCABD2/pMW-Pthr-ydbK. The results are shown in Table 3. The unit of the specific activity is the same as that used in Table 1.

TABLE 3

| Plasmid | Specific activity |
| --- | --- |
| pMW-Pthr | 0.0 |
| pMW-Pthr-ydbK | 8.0 |

Example 6

Construction of a Plasmid to Express the Pyruvate Synthase Gene of *Escherichia coli*, Flavodoxin NADP$^+$ Reductase Gene of *Escherichia coli*, and Ferredoxin Gene of *Escherichia coli*

The plasmid pMW-Pthr-fpr containing the flavodoxin NADP$^+$ reductase gene of *Escherichia coli* described in Example 3 was digested with SmaI, and the obtained fpr gene fragment was ligated with the plasmid pMW-Pthr-fdx containing the ferredoxin gene of *Escherichia coli* treated with SmaI to obtain pMW-Pthr-fpr-fdx. Then, pMW-Pthr-ydbK was digested with KpnI, and the ydbK gene fragment was ligated with pMW-Pthr-fpr-fdx treated with KpnI to construct a plasmid to enhance expression of the pyruvate synthase gene of *Escherichia coli*, flavodoxin NADP$^+$ reductase gene of *Escherichia coli* and ferredoxin fdx gene, pMW-Pthr-fpr-ydbK-fdx.

Example 7

Effect on L-Lysine-Producing Ability of a Strain with Enhanced Expression of the Pyruvate Synthase Gene of *Escherichia coli*, Flavodoxin NADP$^+$ Reductase Gene of *Escherichia coli* and Ferredoxin Gene of *Escherichia coli* Using Ethanol as the Carbon Source <7-1> Introduction of the Plasmid to Amplify the Pyruvate Synthase Gene of *Escherichia coli*, Flavodoxin NADP$^+$ Reductase Gene of *Escherichia coli* and Ferredoxin Gene of *Escherichia coli* into WC196Δmez adhE* Strain pMW-Pthr-fpr-ydbK-fdx and the control vector pMW-Pthr were introduced into WC196Δmez adhE*/pCABD2 by electroporation, respectively, and transformants were obtained on the basis of the kanamycin resistance, and introduction of the plasmids were confirmed. The strain expressing the pyruvate synthase gene of *Escherichia coli* was designated WC196Δmez adhE*/pCABD2/pMW-Pthr-fpr-ydbK-fdx, and the control strain was designated WC196Δmez adhE*/pCABD2/pMW-Pthr.

<7-2> Effect on L-Lysine-Producing Ability of the Strain with Enhanced Expression of the Pyruvate Synthase Gene of *Escherichia coli*, Flavodoxin NADP$^+$ Reductase Gene of *Escherichia coli* and Ferredoxin Gene of *Escherichia coli* Using Ethanol as the Carbon Source>

Both WC196Δmez adhE*/pCABD2/pMW-Pthr and WC196Δmez adhE*/pCABD2/pMW-Pthr-fpr-ydbK-fdx were inoculated onto LB plate medium, respectively, and cultured overnight at 37° C. The cells corresponding to ⅛ of the plate were inoculated into 20 ml of the ethanol medium having the following composition in a 500 ml-volume Sakaguchi flask, and aerobically cultured at a stirring rate of 120 rpm at 37° C. for 96 hours. L-lysine which accumulated in the medium and residual ethanol were measured by using a Biosensor BF-5 (Oji Scientific Instruments). The turbidity of the medium was also measured. Averages of the values obtained in the culture performed in duplicate are shown in Table 4. Improved production of L-lysine was observed for the strain with enhanced expression of the pyruvate synthase gene of *Escherichia coli*, flavodoxin NADP$^+$ reductase gene of *Escherichia coli* and ferredoxin gene of *Escherichia coli*, compared with the control.

| Composition of ethanol medium: | |
| --- | --- |
| Ethanol | 20 ml/L |
| MgSO$_4$•7H$_2$O | 1.0 g/L |
| (NH$_4$)$_2$SO$_4$ | 12 g/L |
| KH$_2$PO$_4$ | 0.5 g/L |
| Yeast extract | 1.0 g/L |
| FeSO$_4$•7H$_2$O | 0.01 g/L |
| MnSO$_4$•5H$_2$O | 0.01 g/L |
| Kanamycin | 40 mg/L |
| Streptomycin | 20 mg/L |
| Calcium carbonate | 30 g/L | pH 7.0 (adjusted with KOH)
Sterilization conditions: 115° C., 10 minutes

TABLE 4

| Strain | Lys (g/l) | EtOH (V/V %) | OD620 |
| --- | --- | --- | --- |
| WC196Δmez adhE*/pCABD2/pMW-Pthr | 2.47 | 0.00 | 14.7 |
| WC196Δmez adhE*/pCABD2/pMW-Pthr-fpr-ydbK-fdx | 2.89 | 0.00 | 9.3 |

Example 8

Construction of the Plasmid to Express the pyruvate:NADP$^+$ Oxidoreductase Gene of *Euglena gracilis* and Measurement of Activity

*Euglena gracilis* is a photosynthetic protist, with an optimum growth temperature of 27° C. The pyruvate:NADP$^+$ oxidoreductase gene was isolated from this organism, and a plasmid expressing this gene was constructed.

<8-1> Construction of the Plasmid to Express the pyruvate:NADP$^+$ Oxidoreductase Gene of *Euglena gracilis*

PCR was performed by using the chromosomal DNA of *Euglena gracilis* as the template and the oligonucleotides shown in SEQ ID NOS: 40 and 41. The gene fragment was digested with KpnI, and the digested fragment was inserted into the KpnI site of pUC19 (Takara Bio) to construct a plasmid, which was designated pUC-PNO. After it was confirmed that the pyruvate:NADP$^+$ oxidoreductase gene contained no PCR error over the full length by using BigDye Terminators vl. I Cycle Sequencing Kit, the pyruvate:NADP$^+$ oxidoreductase gene was excised from pUC-PNO with KpnI, and inserted into the KpnI site of pMW-Pthr to construct the plasmid pMW-Pthr-PNO.

<8-2> Confirmation of Expression of pyruvate:NADP$^+$ Oxidoreductase pMW-Pthr-PNO and the control vector pMW-Pthr were introduced into the WC196ΔcadAΔldc/pCABD2 strain by electroporation, respectively, and transformants were obtained on the basis of the kanamycin resistance, and introduction of the plasmids was confirmed. The strain expressing the pyruvate:NADP$^+$ oxidoreductase gene of *Euglena gracilis* was designated WC196ΔcadAΔldc/pCABD2/pMW-Pthr-PNO, and the control strain was designated WC196ΔcadAΔldc/pCABD2/pMW-Pthr.

The aforementioned strains were each inoculated into LB medium containing 20 mg/l of streptomycin and 40 mg/l of kanamycin, and cultured overnight at 37° C. with shaking. 1 ml of the medium was inoculated into 20 ml of LB medium containing 20 mg/l of streptomycin and 40 mg/l of kanamycin, and cultured at 37° C. for 5 hours with shaking. The cells were collected by centrifugation and suspended in 1 ml of PBS. The cells in the suspension were disrupted by using an ultrasonicator, the suspension was centrifuged at 15000 rpm for 15 minutes, and the supernatant was used as a crude extract Protein concentration in the crude extract was measured by using Protein Assay CBB Solution (Nakalai Tesque), and the crude extract containing 10 µg of protein was used to prepare the samples. Each sample was prepared by adding NuPAGE LDS Sample Buffer (Invitrogen) to the crude extract at a concentration of 1.1×, then adding NuPAGE Sample Reducing Agent (Invitrogen) to a final concentration of 10%, and heating the mixture at 70° C. for 10 minutes. The prepared sample was subjected to electrophoresis using NuPAGE Tris-Acetate Gel 3-8% (Invitrogen). MagicMark XP Western Protein Standard (Invitrogen) was used as markers.

The gel after electrophoresis was transferred to a membrane by using iBlot Gel Transfer Device (Invitrogen). After the transfer, the process from blocking to detection were performed by using WesternBreeze Chemiluminescent Western Blot Immunodetection Kit (Invitrogen). First, the membrane was subjected to a blocking treatment for 30 minutes, washed twice with purified water and incubated in an anti-PNO serum solution diluted 1000 times for 1 hour. The membrane was washed 3 times with a washing solution, and incubated in a second antibody solution for 30 minutes. The membrane was washed 3 times with a washing solution and further twice with purified water, sprinkled with a detection reagent, and subjected to detection using Lumino-image Analyzer LAS-1000 (Fuji Photo Film). The results are shown in FIG. 1. A band presumed to be PNO was detected around 200 kD for the WC196ΔcadAΔldc/pCABD2/pMW-Pthr-PNO strain, whereas a band was not detected for the control strain WC196ΔcadAΔldc/pCABD2/pMW-Pthr.

Example 9

Construction of the Plasmid to Express the pyruvate:NADP+ Oxidoreductase Gene of *Euglena gracilis*

The pyruvate:NADP+ oxidoreductase gene fragment was excised from the plasmid pUC-PNO described in Example 8 with KpnI and inserted into the KpnI site of pMW-Pthr to construct the plasmid pMW-Pthr-PNO.

Example 10

Effect on L-Lysine-Producing Ability of the Strain with Enhanced Expression of the pyruvate:NADP+ Oxidoreductase Gene of *Euglena gracilis* Using Oleic Acid as the Carbon Source <10-1> Introduction of the Plasmid for Amplification of pyruvate:NADP+ Oxidoreductase Gene of *Euglena gracilis* into the WC196Δmez Strain pMW-Pthr-PNO and the control vector pMW-Pthr were introduced into WC196Δmez/pCABD2 by electroporation, respectively, and transformants were obtained on the basis of the kanamycin resistance, and introduction of the plasmids were confirmed. The strain expressing the pyruvate:NADP+ oxidoreductase gene of *Euglena gracilis* was designated WC196Δmez/pCABD2/pMW-Pthr-PNO, and the control strain was designated WC196Δmez/pCABD2/pMW-Pthr.

<10-2> Effect on L-Lysine-Producing Ability of the Strain with Enhanced Expression of the pyruvate:NADP+ Oxidoreductase Gene of *Euglena gracilis* Using Oleic Acid as the Carbon Source Both WC196Δmez/pCABD2/pMW-Pthr and WC196Δmez/pCABD2/pMW-Pthr-PNO were inoculated onto the LB plate medium, respectively, and cultured overnight at 37° C. The cells corresponding to ⅛ of the plate were inoculated into 20 ml of the oleic acid medium having the following composition in a 500 ml-volume Sakaguchi flask and aerobically cultured at a stirring rate of 120 rpm at 37° C. for 72 hours. L-lysine which accumulated in the medium was measured by using a Biosensor BF-5 (Oji Scientific Instruments). The live cell count in the medium was also measured. Averages of the values obtained in the culture performed in duplicate are shown in Table 5. Improvement in the production of L-lysine was observed for the strain in which expression of pyruvate:NADP+ oxidoreductase gene of *Euglena gracilis* was enhanced, compared with the control.

| Composition of oleic acid medium: | |
|---|---|
| Sodium oleate | 20 g/L |
| $MgSO_4·7H_2O$ | 1.0 g/L |
| $(NH_4)_2SO_4$ | 12 g/L |
| $KH_2PO_4$ | 0.5 g/L |
| Yeast extract | 1.0 g/L |
| $FeSO_4·7H_2O$ | 0.01 g/L |
| $MnSO_4·5H_2O$ | 0.01 g/L |
| Kanamycin | 40 mg/L |
| Streptomycin | 20 mg/L |
| Calcium carbonate | 30 g/L | pH 7.0 (adjusted with KOH)
Sterilization conditions: 115° C., 10 minutes

TABLE 5

| Strain | Lys (g/l) | Live cell count ($10^8$/ml) |
|---|---|---|
| WC196Δmez/pCABD2/pMW-Pthr | 1.77 | 22.3 |
| WC196Δmez/pCABD2/pMW-Pthr-PNO | 2.41 | 15.9 |

Example 11

Effect on L-Lysine-Producing Ability of the Strain with Enhanced Expression of the pyruvate:NADP+ Oxidoreductase Gene of *Euglena gracilis* Using Ethanol as the Carbon Source <11-1> Introduction of the Plasmid for Amplification of pyruvate:NADP+ Oxidoreductase Gene of *Euglena gracilis* into WC196Δmez adhE* pMW-Pthr-PNO and the control vector pMW-Pthr were introduced into WC196Δmez adhE*/pCABD2 by electroporation, respectively, and transformants were obtained on the basis of the kanamycin resistance, and introduction of the plasmids was confirmed. The strain expressing the pyruvate:NADP+ oxidoreductase gene of *Euglena gracilis* was designated WC196Δmez adhE*/pCABD2/pMW-Pthr-PNO, and the control strain was designated WC196Δmez adhE*/pCABD2/pMW-Pthr.

<11-2> Effect on L-Lysine-Producing Ability of the Strain with Enhanced Expression of the pyruvate:NADP⁺ Oxidoreductase Gene of *Euglena gracilis* Using Ethanol as the Carbon Source Both WC196Δmez adhE*/pCABD2/pMW-Pthr and WC196Δmez adhE*/pCABD2/pMW-Pthr-PNO were each inoculated onto LB plate medium, and precultured overnight at 37° C. The cells corresponding to ⅛ of the plate were inoculated into 20 ml of the ethanol medium having the following composition in a 500 ml-volume Sakaguchi flask and aerobically cultured at a stirring rate of 120 rpm at 37° C. for 96 hours. After 96 hours, 1 ml of the medium was sampled, and L-lysine which had accumulated in the medium was measured by using a Biosensor BF-5 (Oji Scientific Instruments). The turbidity of the medium was also measured. Averages of the values obtained in the culture performed in duplicate are shown in Table 6. Improvement in the production of L-lysine was observed in the strain with enhanced expression of the pyruvate:NADP⁺ oxidoreductase gene of *Euglena gracilis*, compared with the control.

| Composition of ethanol medium: | |
|---|---|
| Ethanol | 20 ml/L |
| MgSO$_4$•7H$_2$O | 1.0 g/L |
| (NH$_4$)$_2$SO$_4$ | 12 g/L |
| KH$_2$PO$_4$ | 0.5 g/L |
| Yeast extract | 1.0 g/L |
| FeSO$_4$•7H$_2$O | 0.01 g/L |
| MnSO$_4$•5H$_2$O | 0.01 g/L |
| Kanamycin | 40 mg/L |
| Streptomycin | 20 mg/L |
| Calcium carbonate | 30 g/L | pH 7.0 (adjusted with KOH)
Sterilization conditions: 115° C., 10 minutes

TABLE 6

| Strain | Lys (g/l) | EtOH (V/V %) | OD620 |
|---|---|---|---|
| WC196Δmez adhE*/pCABD2/pMW-Pthr | 2.47 | 0.00 | 14.7 |
| WC196Δmez adhE*/pCABD2/pMW-Pthr-fbr-ydbK-fdx | 2.89 | 0.00 | 9.3 |

Explanation of Sequence Listing:

SEQ ID NO: 1: Nucleotide sequence of *C. tepidum* pyruvate synthase gene

SEQ ID NO: 2: Amino acid sequence of *C. tepidum* pyruvate synthase

SEQ ID NO: 3: Nucleotide sequence of *E. coli* pyruvate synthase gene

SEQ ID NO: 4: Amino acid sequence of *E. coli* pyruvate synthase

SEQ ID NO: 5: Nucleotide sequence of *E. gracilis* pyruvate: NADP⁺ oxidoreductase gene SEQ ID NO: 6: Amino acid sequence of *E. gracilis* pyruvate: NADP⁺ oxidoreductase gene SEQ ID NO: 7: Nucleotide sequence of *E. coli* flavodoxin NADP⁺ reductase(fpr) gene SEQ ID NO: 8: Amino acid sequence encoded by *E. coli E. coli* flavodoxin NADP⁺ reductase(fpr) gene SEQ ID NO: 9: Nucleotide sequence of *E. coli* ferredoxin (fdx) gene SEQ ID NO: 10: Amino acid sequence encoded by *E. coli* ferredoxin(fdx) gene SEQ ID NO: 11: Nucleotide sequence of *E. coli* ferredoxin (yfhL) gene SEQ ID NO: 12: Amino acid sequence encoded by *E. coli* ferredoxin(yfhL) gene SEQ ID NO: 13: Nucleotide sequence of *E. coli* flavodoxin (fldA) gene SEQ ID NO: 14: Amino acid sequence encoded by *E. coli* flavodoxin(fldA) gene SEQ ID NO: 15: Nucleotide sequence of *E. coli* flavodoxin (fldB) gene SEQ ID NO: 16: Amino acid sequence encoded by *E. coli* flavodoxin(fldB) gene SEQ ID NO: 17: Nucleotide sequence of *C. tepidum* ferredoxin I gene SEQ ID NO: 18: Amino acid sequence encoded by *C. tepidum* ferredoxin I gene SEQ ID NO: 19: Nucleotide sequence of *C. tepidum* ferredoxin II gene SEQ ID NO: 20: Amino acid sequence encoded by *C. tepidum* ferredoxin II gene SEQ ID NO: 21: Nucleotide sequence of *E. coli* alcohol dehydrogenase gene SEQ ID NO: 22: Amino acid sequence encoded by *E. coli* alcohol dehydrogenase gene SEQ ID NO: 23: $P_{L-tac}$ promoter and chloramphenicol resistance (Cm$^R$) gene amplification primer 1

SEQ ID NO: 24: $P_{L-tac}$ promoter and chloramphenicol resistance (Cm$^R$) gene amplification primer 2

SEQ ID NO: 25: Nucleotide sequence of $P_{L-tac}$ promoter

SEQ ID NO: 26: $P_{L-tac}$ promoter and chloramphenicol resistance (Cm$^R$) gene amplification primer 3

SEQ ID NO: 27: $P_{L-tac}$ promoter and chloramphenicol resistance (Cm$^R$) gene amplification primer 4

SEQ ID NO: 28: Kanamycin resistance (Cm$^R$) gene amplification primer 1

SEQ ID NO: 29: Kanamycin resistance (Cm$^R$) gene amplification primer 2

SEQ ID NO: 30: Kanamycin resistance (Cm$^R$) gene amplification primer 3

SEQ ID NO: 31: Kanamycin resistance (Cm$^R$) gene amplification primer 4

SEQ ID NO: 32: *E. coli* mutant alcohol dehydrogenase gene amplification primer 1

SEQ ID NO: 33: *E. coli* mutant alcohol dehydrogenase gene amplification primer 2

SEQ ID NO: 34: *E. coli* mutant alcohol dehydrogenase gene amplification primer 3

SEQ ID NO: 35: *C. tepidum* pyruvate synthase gene amplification primer 1

SEQ ID NO: 36: *C. tepidum* pyruvate synthase gene amplification primer 2

SEQ ID NO: 37: Threonine operon promoter sequence

SEQ ID NO: 38: *E. coli* pyruvate synthase gene amplification primer 1

SEQ ID NO: 39: *E. coli* pyruvate synthase gene amplification primer 2

SEQ ID NO: 40: *E. gracilis* pyruvate:NADP⁺ oxidoreductase gene amplification primer 1

SEQ ID NO: 41: *E. gracilis* pyruvate:NADP⁺ oxidoreductase gene amplification primer 2

SEQ ID NO: 42: *E. coli* flavodoxin NADP⁺ reductase gene amplification primer 1

SEQ ID NO: 43: *E. coli* flavodoxin NADP⁺ reductase gene amplification primer 2

SEQ ID NO: 44: *E. coli* fdx gene amplification primer 1

SEQ ID NO: 45: *E. coli* fdx gene amplification primer 2

SEQ ID NO: 46: Nucleotide sequence of *E. coli* pyruvate dehydrogenase Ep1 subunit gene (aceE)

SEQ ID NO: 47: Amino acid sequence of *E. coli* pyruvate dehydrogenase Ep1 subunit SEQ ID NO: 48: Nucleotide sequence of *E. coli* pyruvate dehydrogenase E2 subunit gene (aceF)

SEQ ID NO: 49: Amino acid sequence of *E. coli* pyruvate dehydrogenase E2 subunit SEQ ID NO: 50: Nucleotide sequence of *E. coli* pyruvate dehydrogenase E3 subunit gene (lpdA)

SEQ ID NO: 51: Amino acid sequence of *E. coli* pyruvate dehydrogenase E3 subunit SEQ ID NO: 52: Nucleotide sequence of gene (sfcA) encoding *E. coli* malic enzyme SEQ ID NO: 53: Amino acid sequence of malic enzyme encoded by *E. coli* sfcA gene SEQ ID NO: 54: Nucleotide sequence of gene (b2463) encoding *E. coli* malic enzyme SEQ ID NO: 55: Amino acid sequence of malic enzyme encoded by *E. coli* b2463 gene

INDUSTRIAL APPLICABILITY

By using the microorganism of the present invention, an L-amino acid can be efficiently produced by fermentation. Moreover, according to a preferred embodiment of the method of the present invention, the method of the present invention is an environmentally-friendly method which can reduce carbon dioxide emission by suppressing decarboxylation and utilizing carbon dioxide fixation.

What is claimed is:

1. A method for producing an L-amino acid selected from the group consisting of L-lysine, L-tryptophan, L-phenylalanine, L-valine, L-leucine, L-isoleucine and L-serine comprising:
    A) culturing in a medium a microorganism which has an ability to produce the L-amino acid, and
    B) collecting the L-amino acid from the medium or the microorganism, wherein said microorganism has been modified to increase an activity of pyruvate synthase by a method selected from the group consisting of:
        i) increasing the copy number of a gene encoding pyruvate synthase,
        ii) modifying an expression control sequence of the gene, and
        iii) combinations thereof;
    and wherein pyruvate synthase is selected from the group consisting of:
        (a) a polypeptide comprising the amino acid sequence shown in SEQ ID NO: 2, and
        (b) a polypeptide comprising the amino acid sequence shown in SEQ ID NO: 2, but which includes between 1 and 20 substitutions, deletions, insertions, or additions, and has pyruvate synthase activity.

2. The method according to claim 1, wherein the medium contains ethanol or an aliphatic acid as the carbon source.

3. The method according to claim 1, wherein the gene encoding pyruvate synthase comprises a DNA selected from the group consisting of:
    (a) a DNA comprising the nucleotide sequence shown in SEQ ID NO: 1, and
    (b) a DNA which is able to hybridize with a sequence complementary to the nucleotide sequence shown in SEQ ID NO: 1 under stringent conditions comprising washing at 68° C., 0.1×SSC, 0.1% SDS and encoding a polypeptide having pyruvate synthase activity.

4. The method according to claim 1, wherein the microorganism has been further modified to increase the activity of ferredoxin-NADP$^+$reductase by a method selected from the group consisting of:
    a) increasing the copy number of a gene encoding ferrodoxin-NADP$^+$reductase,
    b) modifying an expression control sequence of the gene, and
    c) combinations thereof, wherein said ferredoxin-NADP⁺reductase is selected from the group consisting of:
- (a) a polypeptide comprising the amino acid sequence of SEQ ID NO: 8, and
- (b) a polypeptide comprising the amino acid sequence of SEQ ID NO: 8, but which includes between 1 and 20 substitutions, deletions, insertions or additions, and has ferredoxin-NADP⁺reductase activity.

5. The method according to claim 1, wherein the microorganism has been further modified to increase production of ferredoxin or flavodoxin by a method selected from the group consisting of:
  i) increasing the copy number of a gene encoding ferredoxin or flavodoxin,
  ii) modifying an expression control sequence of the gene, and
  iii) combinations thereof,
wherein said ferredoxin is selected from the group consisting of:
- (a) a polypeptide comprising the amino acid sequence of SEQ ID NO: 10,
- (b) a polypeptide comprising the amino acid sequence of SEQ ID NO: 10, but which includes between 1 and 20 substitutions, deletions, insertions or additions, and has ferredoxin activity,
- (c) a polypeptide comprising the amino acid sequence of SEQ ID NO: 12,
- (d) a polypeptide comprising the amino acid sequence of SEQ ID NO: 12, but which includes between 1 and 20 substitutions, deletions, insertions or additions, and has ferredoxin activity,
- (e) a polypeptide comprising the amino acid sequence of SEQ ID NO: 18,
- (f) a polypeptide comprising the amino acid sequence of SEQ ID NO: 18, but which includes between 1 and 20 substitutions, deletions, insertions or additions, and has ferredoxin activity,
- (g) a polypeptide comprising the amino acid sequence of SEQ ID NO: 20, and
- (h) a polypeptide comprising the amino acid sequence of SEQ ID NO: 20, but which includes between 1 and 20 substitutions, deletions, insertions or additions, and has ferredoxin activity; and wherein said flavodoxin is selected from the group consisting of:
- (i) a polypeptide comprising the amino acid sequence of SEQ ID NO: 14,
- (j) a polypeptide comprising the amino acid sequence of SEQ ID NO: 14, but which includes between 1 and 20 substitutions, deletions, insertions or additions, and has flavodoxin activity,
- (k) a polypeptide comprising the amino acid of SEQ NO: 16, and
- (l) a polypeptide comprising the amino acid sequence of SEQ ID NO: 16, but which includes between 1 and 20 substitutions, deletions, insertions or additions, and has flavodoxin activity.

6. The method according to claim 1, wherein the microorganism has been further modified to decrease pyruvate dehydrogenase activity by a method selected from the group consisting of:
  i) introducing a deletion or mutation into a gene encoding pyruvate dehydrogenase,
  ii) introducing a deletion or mutation into an expression control sequence of the gene, and
  iii) combinations thereof;

wherein said pyruvate dehydrogenase comprises an E1p subunit, E2p subunit and E3 subunit, and wherein said E1p subunit is selected from the group consisting of:
- (a) a polypeptide comprising the amino acid sequence of SEQ ID NO: 47, and
- (b) a polypeptide comprising the amino acid sequence of SEQ ID NO: 47, but which includes between 1 and 20 substitutions, deletions, insertions and additions, and has pyruvate dehydrogenase activity;

wherein said E2p subunit is selected from the group consisting of:
- (c) a polypeptide comprising the amino acid sequence of SEQ ID NO: 49, and
- (d) a polypeptide comprising the amino acid sequence of SEQ ID NO: 49, but which includes between 1 and 20 substitutions, deletions, insertions or additions, and dihydrolipoyl transacetylase activity; and wherein said E3 subunit is selected from the group consisting of:
- (e) a polypeptide comprising the amino acid sequence of SEQ ID NO: 51, and
- (f) a polypeptide comprising the amino acid sequence of SEQ ID NO: 51, but which includes between 1 and 20 substitutions, deletions, insertions or additions, and has dihydrolipoamide dehydrogenase activity.

7. The method according to claim 1, wherein the microorganism has been further modified so that it can aerobically assimilate ethanol by mutating the alcohol dehydrogenase derived from *Escherichia coli* so that the glutamic acid at position 569 is replaced with an amino acid other than glutamic acid and aspartic acid.

8. The method according to claim 1, wherein the microorganism is a bacterium belonging to a genus selected from the group consisting of *Escherichia, Enterobacter, Pantoea, Klebsiella*, and *Serratia*.

9. The method according to claim 1, wherein the microorganism is a coryneform bacterium.

10. The method according to claim 1, wherein the microorganism is *Escherichia coli*.

11. A method for producing an L-amino acid selected from the group consisting of L-lysine, L-tryptophan, L-phenylalanine, L-valine, L-leucine, L-isoleucine and L-serine comprising:
  A) culturing in a medium a microorganism which has an ability to produce the L-amino acid, and
  B) collecting the L-amino acid from the medium or the microorganism, wherein said microorganism has been modified to increase an activity of pyruvate synthase by a method selected from the group consisting of:
  i) increasing the copy number of a gene encoding pyruvate synthase,
  ii) modifying an expression control sequence of the gene, and
  iii) combinations thereof;
and wherein pyruvate synthase comprises the amino acid sequence shown in SEQ ID NO: 2.

12. A method for producing an L-amino acid selected from the group consisting of L-lysine, L-tryptophan, L-phenylalanine, L-valine, L-leucine, L-isoleucine and L-serine comprising:

A) culturing in a medium a microorganism which has an ability to produce the L-amino acid, and
B) collecting the L-amino acid from the medium or the microorganism, wherein said microorganism has been modified to increase an activity of pyruvate synthase by method selected from the group consisting of:
i) increasing the copy number of a gene encoding pyruvate synthase,
ii) modifying an expression control sequence of the gene, and
iii) combinations thereof;

and wherein the gene encoding pyruvate synthase is a DNA comprising the nucleotide sequence shown in SEQ ID NO: 1.

* * * * *

UNITED STATES PATENT AND TRADEMARK OFFICE
CERTIFICATE OF CORRECTION

| | | |
|---|---|---|
| PATENT NO. | : 7,833,761 B2 | Page 1 of 1 |
| APPLICATION NO. | : 12/202476 | |
| DATED | : November 16, 2010 | |
| INVENTOR(S) | : Masaru Terashita et al. | |

It is certified that error appears in the above-identified patent and that said Letters Patent is hereby corrected as shown below:

Claim 4 should be amended as follows:

4. The method according to claim 1, wherein the microorganism has been further modified to increase the activity of ferredoxin-NADP+ reductase by a method selected from the group consisting of:
a) increasing the copy number of a gene encoding ferredoxin-NADP+ reductase,
b) modifying an expression control sequence of the gene, and
c) combinations thereof,
wherein said ferredoxin-NADP+ reductase is selected from the group consisting of:
(a) a polypeptide comprising the amino acid sequence of SEQ ID NO: 8, and
(b) a polypeptide comprising the amino acid sequence of SEQ ID NO: 8, but which includes between 1 and 20 substitutions, deletions, insertions or additions, and has ferredoxin-NADP+ reductase activity.

Signed and Sealed this
Eighth Day of March, 2011

David J. Kappos
*Director of the United States Patent and Trademark Office*

UNITED STATES PATENT AND TRADEMARK OFFICE
CERTIFICATE OF CORRECTION

PATENT NO. : 7,833,761 B2
APPLICATION NO. : 12/202476
DATED : November 16, 2010
INVENTOR(S) : Masaru Terashita et al.

It is certified that error appears in the above-identified patent and that said Letters Patent is hereby corrected as shown below:

Column 162, line 57 - Column 163, line 8,
Claim 4 should be amended as follows:

4. The method according to claim 1, wherein the microorganism has been further modified to increase the activity of ferredoxin-NADP+ reductase by a method selected from the group consisting of:
a) increasing the copy number of a gene encoding ferredoxin-NADP+ reductase,
b) modifying an expression control sequence of the gene, and
c) combinations thereof,
wherein said ferredoxin-NADP+ reductase is selected from the group consisting of:
(a) a polypeptide comprising the amino acid sequence of SEQ ID NO: 8, and
(b) a polypeptide comprising the amino acid sequence of SEQ ID NO: 8, but which includes between 1 and 20 substitutions, deletions, insertions or additions, and has ferredoxin-NADP+ reductase activity.

This certificate supersedes the Certificate of Correction issued March 8, 2011.

Signed and Sealed this
Twenty-ninth Day of March, 2011

David J. Kappos
*Director of the United States Patent and Trademark Office*